(12) United States Patent
Yudin et al.

(10) Patent No.: US 8,143,375 B2
(45) Date of Patent: Mar. 27, 2012

(54) AZIRIDINE ALDEHYDES, AZIRIDINE-CONJUGATED AMINO DERIVATIVES, AZIRIDINE-CONJUGATED BIOMOLECULES AND PROCESSES FOR THEIR PREPARATION

(75) Inventors: Andrei K. Yudin, Toronto (CA); Ryan Hill, Toronto (CA)

(73) Assignee: The Governing Council of the University of Toronto, Toronto, Ontario (CA)

( * ) Notice: Subject to any disclaimer, the term of this patent is extended or adjusted under 35 U.S.C. 154(b) by 60 days.

(21) Appl. No.: 12/446,343

(22) PCT Filed: Oct. 22, 2007

(86) PCT No.: PCT/CA2007/001882
§ 371 (c)(1),
(2), (4) Date: Jul. 13, 2009

(87) PCT Pub. No.: WO2008/046232
PCT Pub. Date: Apr. 24, 2008

(65) Prior Publication Data
US 2010/0317832 A1    Dec. 16, 2010

Related U.S. Application Data

(60) Provisional application No. 60/852,980, filed on Oct. 20, 2006, provisional application No. 60/907,339, filed on Mar. 29, 2007.

(51) Int. Cl.
C07D 203/08 (2006.01)
C07D 498/04 (2006.01)
C07D 487/22 (2006.01)

(52) U.S. Cl. ........ 530/345; 548/217; 548/418; 548/966; 548/967

(58) Field of Classification Search .................. None
See application file for complete search history.

(56) References Cited

FOREIGN PATENT DOCUMENTS
CA      2427046 A1    11/2003

OTHER PUBLICATIONS

Tarburton et al., caplus an 1980:21603.*
Hili et al, 2006, caplus an 2006:1246888.*
F. J. Sardina et al., "Enantiospecific Synthesis of Heterocycles from alpha-Amino Acids", Chem. Rev., 96: 1825-1872 (1996).
S.V. Serafin et al., "Decomposition of Protonated Threonine, Its Stereoisomers, and Its Homologues in the Gas Phase: Evidence for Internal Backside Displacement", Org. Lett., 6: 1561-1564 (2004).
A. Solladie-Cavallo et al., "anti Ethyl beta-thienyl-Beta-amino-alpha-hydroxy propionate: a regio and stereoselective ring opening of trans ethyl 2-thienyl-glycidate", Tetrahedron Letters, 44: 5075-5078 (2003).
M. Szelke et al., "Potent new inhibitors of human renin", Nature, 299: 555-557 (1982).
P. Tarburton et al., "Stereostructural Investigations of trans- and cis-1-alkyl-2-aryl (alkyl)-3-carboaziridines by 1H and 13C NMR", Studies in Organic Chemistry (Amsterdam), 3 (New Trends Heterocycl. Chem.,), pp. 112-129 (1979).
L. Tietze, "Domino Reactions in Organic Synthesis", Chem. Rev. 96: 115-136 (1996).
B.M. Trost, "The Atom Economy—A Search for Synthetic Efficiency", Science, 254: 1471-1477 (1991).
M. Varoglu et al., "Mapping the Mitomycin Biosynthetic Pathway by Functional Analysis of the MitM Aziridine N-Methyltransferase", J. Am. Chem. Soc., 123: 6712-6713 (2001).
R. Vicik et al., "Inhibitors of Cysteine Proteases", Curr. Top. Med. Chem., 6: 331-353 (2006).
E. Kyburz et al., "Synthese und Eigenschaften von Aziridincarbonsaureestern", Hel. Chim. Acta, 49: 359-69 (1966).
Y.-M. Wang et al., "Substituent Effects on the Ring Opening of 2-aziridinylmethyl Radicals", J. Org. Chem., 70: 3633-3640 (2005).
H. Wasserman et al., "Transamidation Reactions Using B-Lactams. The Synthesis of Homaline", Tetrahedron Letters, 23(4): 465-468 (1982).
L. Weber et al., "Discovery of New Multi Component Reactions with Combinatorial Methods", Synlett, 3: 366-374 (1999).
P. Wender et al., "New reactions and step economy: the total synthesis of (+)-salsolene oxide based on the type II transition metal-catalyzed intramolecular [4+4] cycloaddition", Tetrahedron, 62: 7505-7511 (2006).
C. Whitman et al., "Synthesis, Chiroptical Properties and Absolute Configuration of Alpha-Phenylglycidic Acid", Tetrahedron, 41: 1183-1192 (1985).
A. Wlodawer, "Structure-Based Inhibitors of HIV-1 Protease", Annu. Rev. Biochem, 62: 543-85 (1993).

(Continued)

*Primary Examiner* — Sun Jae Loewe
(74) *Attorney, Agent, or Firm* — Patrick J. Hagen; Dann, Dorfman, Herrell and Skillman

(57) ABSTRACT

The present invention relates to unprotected amino aldehydes and applications for same. More particularly, the present invention relates to novel aziridine aldehydes and processes for preparing these novel compounds. The invention also relates to aziridine-conjugated amino derivatives, and processes for preparing the same. Pentacyclic compounds may be prepared using the aziridine aldehydes of the present invention, and the invention relates to these compounds and the processes by which they are made. The invention also relates to aziridine-conjugated bioactive molecules, such as amino acids and peptides, and processes for preparing such compounds.

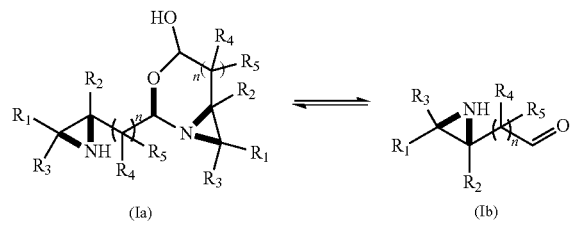

13 Claims, 8 Drawing Sheets

OTHER PUBLICATIONS

L. Yu et al., "Preparation and Reactivity of Versatile alpha-Amino Ketones", J. Org. Chem., 72: 1737-1741 (2007).
A. Yudin et al., "Overcoming the Demons of Protecting Groups with Amphoteric Molecules", Chem. Eur. J., 13: 6538-6542 (2007).
P. Zhou et al., "Asymmetric Syntheses with Aziridinecarboxylate and Aziridinephosphonate Building Blocks", Azindines and Epoxides in Organic Synthesis, Yudin, A.K.; John Wiley & Sons, New York, pp. 73-115 (2006).
Multicomponent Reactions, Ugi Reaction (Eds.: J. Zhu, H. Bienayme), pp. 319-324, Wiley, New York (2005).
IUPAC Compendium of Chemical Terminology, 2nd ed., pp. 71 (1997).
Zell's Popular Encyclopedia; a universal dictionary of English language, science, literature and art by L. Colage, Philadelhpia, T.E. Zell, p. 86 (1871).
P. Pelagatti et al., "Transfer Hydrogenation of Acetophenone Catalyzed by Half-Sandwich Ruthenium (II) Complexes Containing Amino Amide Ligands. Detection of the Catalytic Intermediates by Electrospray Ionization Mass Spectrometry", Organometallics, 24: 5836-5844 (2005).
Philip Tarburton et al., "Stereostructural Investigations of trans- and cis-1-alkyl-2-aryl (alkyl)-3-carboaziridines by 1H and 13C NMR", Studies in Organic Chemistry, 3: 112-29 (Amsterdam 1979).
A. Abdel-Magid et al., "Reductive Amination of Aldehydes and Ketones with Sodium Triacetoxyborohydride. Studies on Direct and Indirect Reductive Amination Procedures", J. Org. Chem., 61: 3849-3862 (1996).
E. Adams et al., "Synthesis and Properties of an Alpha-Amino Aldehyde, Histidinal", J. Biol. Chem., 217: 317-324 (1955).
B. Alcaide et al., "The Regio- and Stereocontrolled Ring Opening of Heteroarylglycidates with Nitrogen Nucleophiles", Tetrahedron Letters, 36: 5417-5420 (1995).
G. R. Ames et al., "cycloHexane-1: 3-diones. Part IV. The Synthesis of Further Terphenyl Derivatives", J. Chem. Soc., 1794-1798 (1958).
L. Aurelio et al., "Synthetic Preparation of N-Methyl-alpha-amino Acids", Chem. Rev., 104: 5823-5846 (2004).
R. Babine et al., "Molecular Recognition of Protein-Ligand Complexes: Applications to Drug Design", Chem. Rev., 97: 1359-1472 (1997).
P. Baran et al., "Total synthesis of marine natural products without using protecting groups", Nature, 446: 404-408 (2007).
R. Bartnik et al., "Sur la stereochimie de la reduction des aminocetones et des aziridinocetones par le borohydrure de zinc", Bull. Pol. Acad. Sci. Chem., 34: 27-33 (1986).
A. Breuning et al., "An improved synthesis of aziridine-2,3-dicarboxylates via azido alcohols—epimerization studies", Tetrahedron: Asymmetry, 14: 3301-3312 (2003).
G. Chen et al., "Strained Enamines as Versatile Intermediates for Stereocontrolled Construction of Nitrogen Heterocycles", J. Org. Chem., 71: 6067-6073 (2006).
I. I. Chervin et al., "Asymmetric Nitrogen, Investigation of the Stereochemistry of Aziridinecarboxylic Acid Derivatives by NMR", Inst. Khim. Fiz., Moscow, USSR. Izvestiya Akademii Nauk SSSR, Seriya Khimicheskaya, 5: 1110-1121 (1988).
D. Cobessi et al., "Crystal Structure at High Resolution of Ferric-pyochelin and its Membrane Receptor FptA from *Pseudomonas aeruginosa*", J. Mol. Biol., 352: 893-904 (2005).
E. Cox et al., "The Pictet-Spengler Condensation: A New Direction for an Old Reaction", Chem. Rev., 95: 1797-1842 (1995).
A. Domling et al., "Multicomponent Reactions with Isocyanides", Angew. Chem. Int. Ed., 39: 3168-3210 (2000).
A. Domling et al., "Multikomponentenreaktionen mit Isocyaniden", Angew. Chem., 112: 330-3344 (2000).
M. Evans et al., "Mechanism-Based Profiling of Enzyme Families", Chem. Rev., 106: 3279-3301 (2006).
E. Fischer et al., "Synthese des d-Glucosamins", Ber. Dtsch. Chem. Ges., 36: 24-29 (1902).
E. Fischer, "Reduktion ds Glykokollesters", Chem. Ber., 41: 1019-1023 (1908).
M. Fonovic et al., "Activity Based Probes for Proteases: Applications to Biomarker Discovery, Molecular Imaging and Drug Screening", Current Pharmaceutical Design, 13: 253-261 (2007).

D. Galonic et al., "Aziridine-2-carboxylic Acid-Containing Peptides: Application to Solution- and Solid-Phase Convergent Site-Selective Peptide Modification", J. Am. Chem. Soc., 127: 7359-7369 (2005).
A. Giannis et al., "Peptidomimetics for Receptor Ligands-Discovery, Development, and Medical Perspectives", Angew. Chem. Int. Ed. Engl., 32: 1244-1267 (1993).
B. Gigant et al., "Structural basis for the regulation of tubulin by vinblastine", Nature, 435: 519-522 (2005).
A. Goldstein et al., "An alternate preparation of thioester resin linkers for solid-phase synthesis of peptide C-terminal thioacids", Tetrahedron Letters: 41: 2797-2800 (2000).
D. Gryko et al., "Synthesis and Reactivity of N-Protected-alpha-Amino Aldehydes", Chirality, 15: 514-541 (2003).
R. Hili et al., "Readily Available Unprotected Amino Aldehydes", J. Am. Chem. Soc., 128: 14772-14773 (2006).
R. Hili et al., "Making carbon-nitrogen bonds in biological and chemical synthesis", Nature Chemical Biology, 2: 284-287 (2006).
R. R. Hill et al., "Enantioselection in peptide bond formation", Organic & Biomolecular Chemistry, 1: 965-972 (2003).
R. Hoffman et al., "Protecting-Group-Free Synthesis", Synthesis, 21: 3531-3541 (2006).
K. Jensen et al., "Backbone Amide Linker (BAL) Strategy for Solid-Phase Synthesis of C-Terminal-Modified and Cyclic Peptides", J. Am. Chem. Soc., 120: 5441-5452 (1998).
E. Johnson et al., "Insights into the Mechanism and Catalysis of the Native Chemical Ligation Reaction", J. Am. Chem. Soc. 128: 6640-6646 (2006).
J. Jurczak et al., Optically Active N-Protected alpha-Amino Aldehydes in Organic Synthesis, Chem. Rev., 89: 149-164 (1989).
A. Katritzky et al., "Stereoselective syntheses of 1H-imidazo[2,1-alpha]isoindole-2,5(3H,9bH)-diones", J. Chem. Soc. Perkin Trans., 1: 1767-1770 (2001).
S. Kuo et al., "Titanium Chloride Catalyzed Addition of Aziridine to Ketones. A Route to N-Aziridinylenamines", J. Org. Chem., 35: 1861-1866 (1970).
J. Legters et al., "A Convenient Synthesis of Optically Active 1H-Aziridine-2-Carboxylic Acids (Esters)", 30: 4881-4884 (1989).
G. Lelais et al., "Modern Strategies in Organic Catalysis: The Advent and Development of Iminium Activation", Aldrichimica Acta, 39: 79-87 (2006).
D. Leung et al., "Protease Inhibitors: Current Status and Future Prospects", J. Med. Chem., 43: 305-341 (2000).
H. Li et al., "Enantioselective Nitroaldol Reaction of alpha-Keotesters Catalyzed by Cinchona Alkaloids", J. Am. Chem. Soc., 128: 732-733 (2006).
W. Lieke, "Ueber das Cyanallyl". LIEBIGS, Justus, Ann. Chem., 112: 316-321 (1859).
B. List, "The ying and yang of asymmetric aminocatalysis", Chem. Commun., 819-824 (2006).
D. Maly et al., Combinatorial Strategies for Targeting Protein Families: Application to the Proteases, ChemBioChem, 3: 16-37 (2002).
J. McFarland et al., "Reductive Alkylation of Proteins Using Iridium Catalyzed Transfer Hydrogenation", J. Am. Chem. Soc., 127: 13490-13491 (2005).
G. Means, "Reductive Alkylation of Proteins", Journal of Protein Chemistry, 3(1): 121-130 (1984).
A. Myers et al., "Observations Concerning the Existence and Reactivity of Free alpha-Amino Aldehydes as Chemical Intermediates: Evidence for Epimerization-Free Adduct Formation with Various Nucleophiles", J. Am. Chem. Soc., 122: 3236-3237 (2000).
C. Neuberg, "Reduktion von Aminosauren zu Aminoaldehyden", Chem. Ber., 41: 956-963, 2008.
T. Ooi et al., "Asymmetric Skeletal Rearrangement of Symmetrically alpha,alpha-Disubstituted alpha-Amino Aldehydes: A New Entry to Optically Active alpha-Hydroxy Ketones", J. Am. Chem. Soc., 125: 3220-3221 (2003).
A. Pangborn et al., "Safe and Convenient Procedure for Solvent Purification", Organometallics, 15: 1518-1520 (1996).
M. Pennings et al., "Chemistry of Four-Membered Cyclic Nitrones. 4. Reaction with Electrophilic Reagents and Conversion into Beta-Lactam Derivatives", J. Org. Chem., 48: 486-491 (1983).

J.V. Potetinova et al., "Synthesis of Modified Peptides wit C-Terminal alpha-Amino Aldehydes", J. Bioorg. Chem., 27: 141-150 (2001).

M.T. Reetz, "Neue Wege zur Nutzung von Aminosauren als chirale Bausteine in der organischen Synthese", Angew. Chem., 103: 1559-1573 (1991).

M.T. Reetz, "New Approaches to the Use of Amino Acids as Chiral Building Blocks in Organic Synthesis", Angew. Chem. Int. Ed., 30: 1531-1546 (1991).

* cited by examiner (prior art)

Pentacycle-derived hybrid

Vinblastine

AZIRIDINE ALDEHYDES, AZIRIDINE-CONJUGATED AMINO DERIVATIVES, AZIRIDINE-CONJUGATED BIOMOLECULES AND PROCESSES FOR THEIR PREPARATION

CROSS-REFERENCE TO RELATED APPLICATIONS

This application is the U.S. National Stage of International Application No. PCT/CA2007/001882, filed Oct. 22, 2007, which claims priority from U.S. Provisional Application No. 60/852,980, filed Oct. 20, 2006 and U.S. Provisional Application No. 60/907,339, filed Mar. 29, 2007. The entire disclosure of each of the aforesaid applications is incorporated by reference in the present application.

FIELD OF THE INVENTION

The present invention relates to a new class of bench-stable compounds that contain seemingly incompatible functional groups: an aldehyde and an unprotected secondary amine. More particularly, the invention relates to unprotected amino aldehydes, processes for preparing such compounds, and applications for these novel compounds in complex synthesis and in the synthesis of bioactive molecules.

BACKGROUND

Despite a seemingly infinite amount of reactions that involve carbon-containing compounds, the vast majority can be divided into one of two large groups: reactions in which a carbon atom undergoes oxidation state change, and reactions in which its oxidation state remains unaffected. Each oxidation state of carbon has a set of reactions associated with it. A subset of reactions relevant to carbon-nitrogen bond formation illustrates this point (Scheme 1). For instance, primary alcohols can undergo nucleophilic displacement to generate amines, enolizable aldehydes can condense with amines giving enamines, whereas carboxylic acids can be converted into amides.

Chemical synthesis of targets of varied complexity is an exercise in interspersing non-redox reactions with the carbon oxidation state adjustments. Chemoselectivity, defined as the preferential reaction of a chemical reagent with one of two or more different functional groups, is one of the biggest challenges facing chemical synthesis (IUPAC Compendium of Chemical Terminology, 2nd ed., 1997). Avoiding the problems of chemoselectivity using protecting groups is commonplace, but comes at the expense of atom (B. M. Trost, *Science* 1991, 254, 1471) and step economy (P. A. Wender, M. P. Croatt, B. Witulski, *Tetrahedron* 2006, 62, 7505). In this regard, it is instructive to observe that biosynthesis avoids the chemoselectivity problems by molecular shape recognition (R. Hili, A. K. Yudin, *Nat. Chem. Biol.* 2006, 2, 284). The event of binding into an enzyme active site allows precise positioning of the functional group about to undergo transformation. In comparison, very few synthetic reagents obey the Michaelis—Menten kinetics. Instead, electronic and/or steric requirements of different functional groups present in a given reactant have to be taken into account in order to reach high levels of selectivity. Parameters such as pKa, redox potential, and A values, are common metrics used by organic chemists in order to compare and predict reactivity of different molecules. None of these parameters come close to describing the overall property of a given molecule. In contrast, enzymatic systems are holistic in their approach to chemical transformations.

In order to find general solutions to protecting group-free synthesis, one approach is to develop reagents and catalysts that emulate enzymatic efficiency with regard to chemoselectivity and practical turnover numbers (For recent discussions, see: R. W. Hoffman, *Synthesis* 2006, 3531; P. S. Baran, T. J. Maimone, J. M. Richter, *Nature* 2007, 446, 404). On the other hand, new ideas about interrelationships between functional groups are expected to play a significant role.

Scheme 1

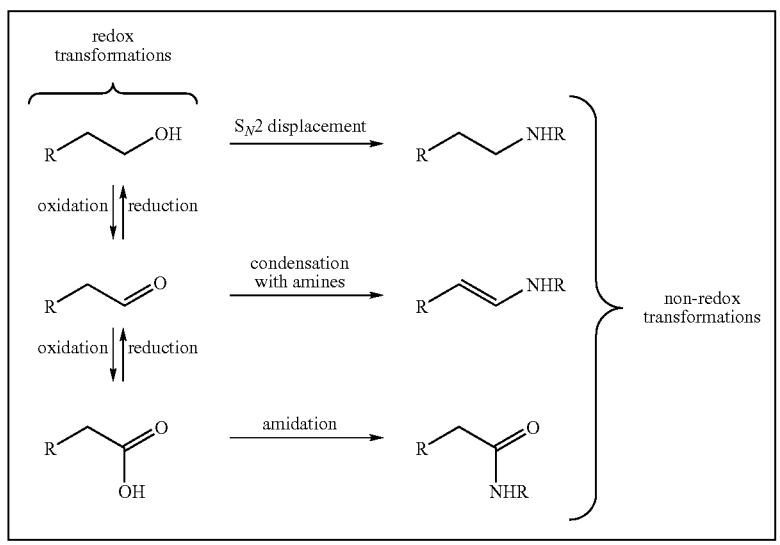

In an ideal world, one would have a capability to chemoselectively manipulate molecules equipped with mutually reactive functional groups. In the realm of acid/base chemistry, the so-called amphoteric molecules have been known for some time. The term amphoteric is of Greek origin: amphoteros literally means "both of two" (Zell's popular encyclopedia; a universal dictionary of English language, science, literature and art by L. Colage, Philadelphia, T. E. Zell, 1871). Although the origin of the word is not related to any particular chemical property, this term has been mainly used in order to refer to a molecule that can act as both acid and base.

For instance, amino acids are amphoteric compounds, characterized by an isoelectric point at which the molecule exists in its zwitterionic state (e.g. L-serine in FIG. 1). Depending on pH, the position of proton can change, affecting the chemical behaviour of the amino acid. Accordingly, amphoterism has belonged to the domain of thermodynamics since proton transfer is typically diffusion-limited. The thermodynamics of proton transfer can temporarily stabilize unstable molecules that contain nucleophilic and electrophilic centres. Fischer, who in 1908 prepared glycinal from the reduction of its ester, demonstrated that protection of the amine functional group by proton at acidic pH stabilized the amino aldehyde, albeit briefly (E. Fischer, Chem. Ber. 1908, 41, 1019). More recently, Myers and co-workers have used a similar method of amine protonation to establish the epimerization-free adduct formation between amino aldehydes with nucleophilic solvent molecules (A. G. Myers, D. W. Kung, B. Zhong, J. Am. Chem. Soc. 2000, 122, 3236). When the pH of the medium was increased to value greater than 5, the amino aldehydes decomposed through self-condensation reactions. The possibility of self-condensation can be suppressed, but it requires incorporation of a quaternary α-carbon (Ooi, T.; Saito, A.; Maruoka, J. J. Am. Chem. Soc. 2003, 125, 3220).

There are few examples of synthetically useful molecules one can consider amphoteric based on kinetic grounds. The most mechanistically instructive case is that of the isocyanide (FIG. 1), first synthesized in 1859 (W. Lieke, Justus Liebigs Ann. Chem. 1859, 112, 316). Two of the widely used multicomponent reactions owe their efficiency to the amphoteric nature of the isocyanide. The Passerini reaction involves a three component condensation between an isocyanide, an aldehyde, and a carboxylic acid to generate α-acyloxycarboxamides. By introducing another component—an amine—into the reaction, Ugi developed a four-component process, which is used to generate dipeptides and other valuable molecules (I. Ugi, A. Dömling, Angew. Chem. 2000, 112, 3300; Angew. Chem. Int. Ed. 2000, 39, 3168; Multicomponent Reactions (Eds.: J. Zhu, H. Bienaymé), Wiley, N.Y., 2005). The critical mechanistic point of this reaction is that the isocyanide carbon establishes a connection with both nucleophile (carboxylic acid) and electrophile (imine) (Scheme 2). The unique amphoteric nature of the isocyanide carbon centre facilitates the discovery of multicomponent processes using simple building blocks (L. Weber, K. Illgen, M. Almstetter, Synlett 1999, 161).

Scheme 2

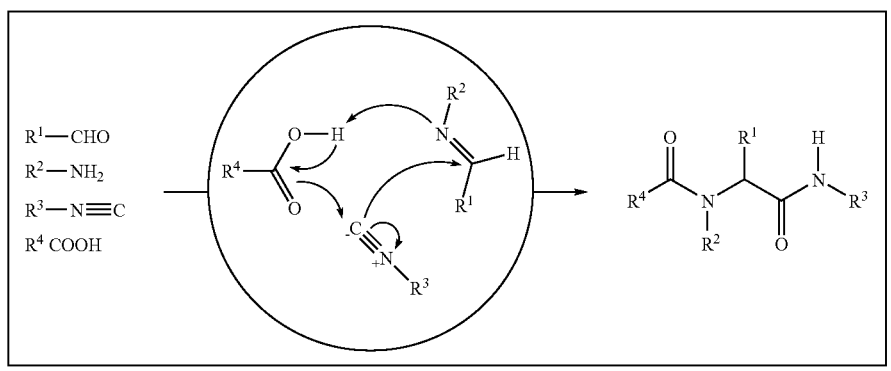

Continuing interest in stereochemically complex natural products and natural product-inspired synthetic molecules requires processes that minimize protection/deprotection sequences on incompatible functional groups. Identification of such reactions, especially in complex heterocycle synthesis, facilitates discovery of bioactive molecules.

Carbonyl groups are arguably the most synthetically useful oxidation state of carbon (Scheme 1) since condensations between amines and carbonyl groups give rise to enamines, some of the most widely used synthetic intermediates (The Chemistry of Enamines (Ed.: Z. Rappoport), New York, 1994). Besides their utility as building blocks in target-oriented synthesis, enamines have many other important applications. For instance, many developments in an active area of current research, organocatalysis, depend on enamine generation for catalytic turnover (B. List, Chem. Commun. 2006, 819; G. Lelais, D. W. C. Macmillan, Aldrichimica Acta 2006, 39, 79). Ironically, in the context of synthesis, enamine formation can be regarded as a limitation: due to their inherent reactivity, a secondary amine and an aldehyde or a ketone cannot be carried through a synthetic sequence in their unprotected forms. Unveiling a secondary amine in the presence of an aldehyde or a ketone is done when an instant condensation resulting in an iminium/enamine system is desired (Scheme 3). It is easy to see that if the unprotected derivatives were to have a kinetic barrier against condensation, they would afford a number of strategic as well as tactical advantages.

Scheme 3

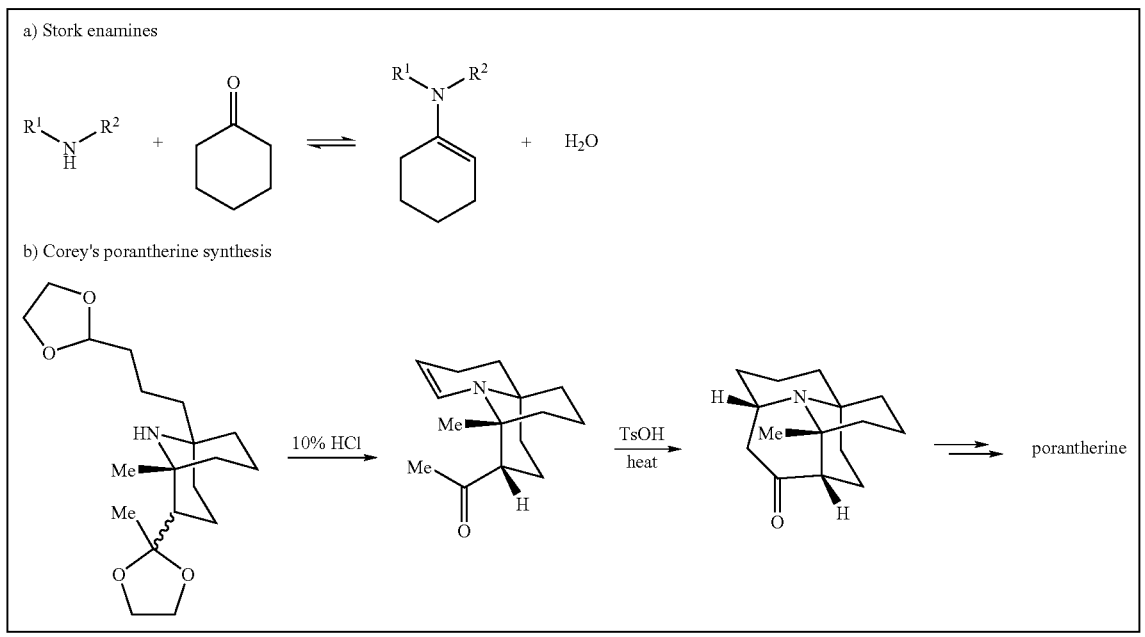

It is difficult to see how an unprotected secondary amine could coexist with an aldehyde in the same molecule for a prolonged period of time (for reviews on N-protected amino aldehydes see: Jurczak, J.; Golebiowski, A. *Chem. Rev.* 1989, 89, 149; Reetz, M. T. *Anew. Chem. Int Ed.* 1991, 30, 1531; Sardina, F. J.; Rapoport, H. *Chem. Rev.* 1996, 1825; $_D$-Glucosamine, a naturally occurring amino aldehyde, is stable as a cyclic aminal salt: Fischer, E.; Leuchs, H. *Ber. Dtsch. Chem. Ges.* 1902, 36, 24; glycinal was characterized through degradation studies: Fischer, E. *Ber.* 1908, 41, 956; Fischer, E. *Ber.* 1908, 41, 1019; for a preparation of histidinal dihydrochloride, see: Adams, E. *J. Biol. Chem.* 1955, 217, 317).

Rheinhoudt (Rheinhoudt et al. *Journal of Organic Chemistry* 1983, 48(4), 486) has previously reported an unprotected aziridine aldehyde (compound 9, see Scheme III from this paper and Scheme 4 shown below).

Scheme 4

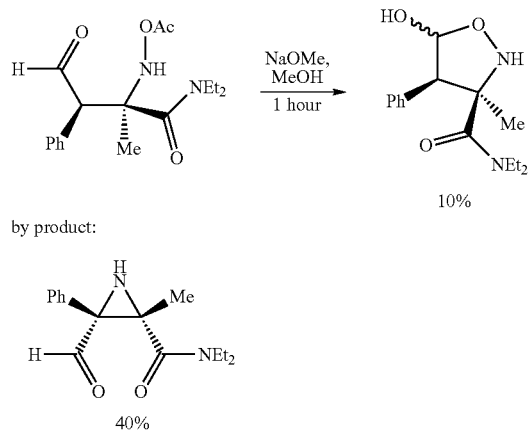

by product:

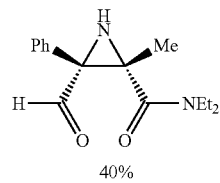

40%
- contaminated pale yellow oil
- decomposes during purification
- δ 9.56 (s, 1 H, CHO)

However, this aziridine aldehyde was isolated as a by-product during a low-yielding synthesis of target compound 14a, and could not be obtained in pure form due to its instability.

Thus, in view of the foregoing, there remains a need for the development of synthetic molecules for use in processes that minimize protection/deprotection sequences on incompatible functional groups, such as amines and aldehydes.

Reversible protease inhibitors feature prominently among modern therapeutic agents (Babine, R. E.; Bender, S. L. *Chem. Rev.* 1997, 97, 1359). The so-called reduced amide bond isosteres contain aminomethylene functional groups in place of the selected amide linkages (Scheme 5a below). This structural substitution is present in a wide range of aspartyl protease inhibitors (Maly, D. J., Huang, L., Ellman, J. A. *ChemBioChem.* 2002, 3, 17; Leung, D.; Abbenante, G.; Fairlie, D. P. *J. Med. Chem.* 2000, 43, 305). The aminomethylene fragment is isosteric with the tetrahedral transition state formed during amide hydrolysis. This ensures that the peptidomimetic inhibitor binds to the protease target tighter than the substrate. At the same time, the reduced amide bond analog is not cleaved by the protease and often displays better binding than its peptide prototype (Szelke, M.; Leckie, B.; Hallett, A.; Jones, D. M.; Sueiras, J.; Atrash, B.; Lever, A. F. Nature 1982, 299, 555). Many different modes of binding between proteases and their inhibitors have been observed by X-ray crystallography (Wlodawer, A.; Erickson, J. *Annu. Rev. Biochem.* 1993, 62, 543). The diversity of recognition mechanisms underscores the importance of optimizing the peptidomimetic inhibitor/protease interactions in the vicinity of the active site.

The most widely employed strategy towards reduced amide bond isosteres is based on N-protected amino aldehydes (Scheme 5b) (Gryko, D.; Chalko, J.; Jurczak, J. *Chirality* 2003, 15, 514). Typically, a peptide or a nitrogen-protected amino acid ("NHP") is converted into the corresponding aldehyde by first forming an ester or a Weinreb amide, which is subsequently reduced by a hydride transfer reagent. These steps are followed by reductive amination with an appropriate amine component.

Scheme 5

(a)
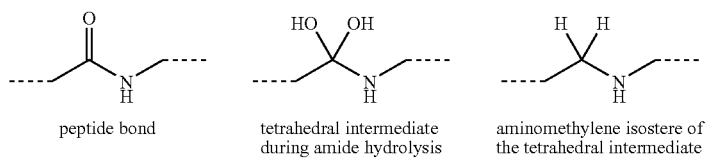

peptide bond | tetrahedral intermediate during amide hydrolysis | aminomethylene isostere of the tetrahedral intermediate (b)
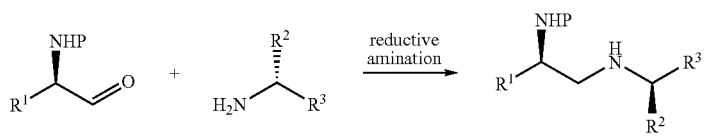

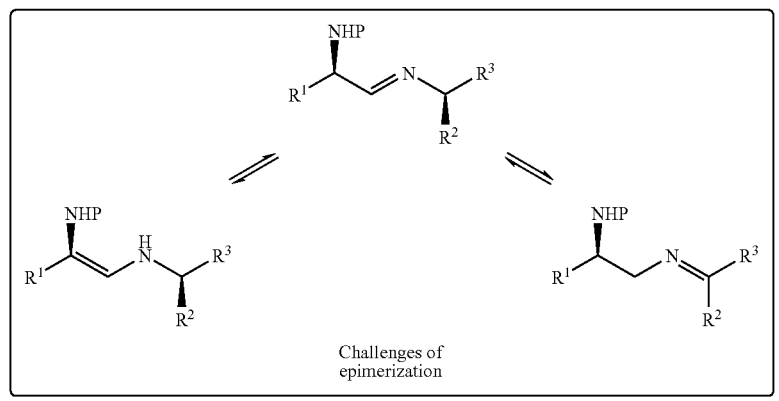

Challenges of epimerization

Although this valuable reaction sequence has been used in numerous academic and industrial applications, there are significant challenges that face this chemistry. The amino aldehydes as well as their immediate precursors are notoriously sensitive to epimerization (Potetinova, J. V.; Milgotina, E. I.; Makarov, V. A.; Voyushina, T. L. Russ. *J. Bioorg. Chem.* 2001, 27, 141). In addition, the imine/enamine equilibrium triggered during the reductive amination can lead to further epimerization on both the amine- and the aldehyde sides of the peptidomimetic fragment (Scheme 5b). Epimerizations on both the amine and the aldehyde sides during peptidomimetic synthesis have been documented (Aurelio, L.; Brownlee Robert, T. C.; Hughes Andrew, B. *Chem. Rev.* 2004, 104, 5823; Wasserman, H. H.; Berger, G. D.; Cho, K. R. *Tetrahedron Lett.* 1982, 23, 465; Jensen, K. J.; Alsina, J.; Songster, M. F.; Vagner, J.; Albericio, F.; Barany, G. *J. Am. Chem. Soc.* 1998, 120, 5441; Giannis, A.; Kolter, T. *Angew. Chem. Int. Ed.* 1993, 32, 1244; Ho, P. T.; Chang, D.; Zhong, J. W. X.; Musso, G. F. *Peptide Res.* 1993, 6, 10). Last but not least, reliance on protecting groups at nitrogen in amino aldehydes diminishes the synthetic efficiency of these operations.

Thus, there is a need for new strategies for developing peptidomimetics.

SUMMARY OF THE INVENTION

In one aspect, the present invention provides a previously unknown class of molecules, aziridine aldehydes.

More particularly, in one aspect, the invention provides a compound of formula (Ia) and/or (Ib):

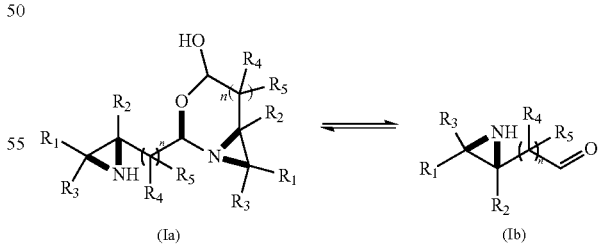

(Ia)      (Ib)

wherein n=0 or 1, and $R_1, R_2, R_3, R_4$ and $R_5$ are independently selected from H; lower alkyl; aryl; heteroaryl; alkenyl; cycloalkyl; heterocycle; esters of the formula —C(O)OR* wherein R* is selected from alkyl and aryl; amides of the formula —C(O)NRR*, wherein R and R* are independently selected from alkyl and aryl; —CH$_2$C(O)R, wherein R is selected from —OH, lower alkyl, aryl, -loweralkyl-aryl, or —NR$_a$R$_b$, where R$_a$ and R$_b$ are independently selected from H, lower alkyl, aryl or -loweralkyl-aryl; —C(O)R$_c$, wherein R$_c$ is selected from lower alkyl, aryl or -loweralkyl-aryl; or -lower alkyl-OR$_d$, wherein R$_d$ is a suitable protecting group;

all of which are optionally substituted at one or more substitutable positions with one or more suitable substituents, with the proviso that when R$_2$ is phenyl, R$_3$ is methyl, and n=0 then R$_1$ cannot be —C(O)NEt$_2$.

In another aspect, the invention provides a compound selected from the group consisting of:

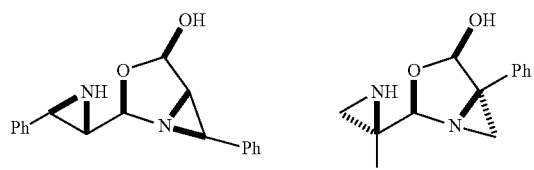

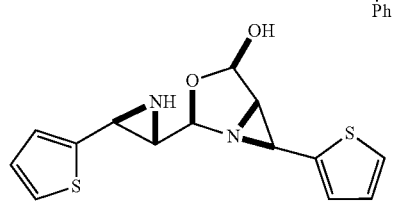

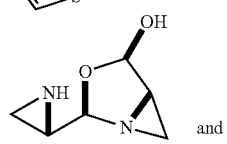

and

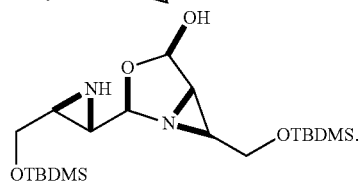

In another aspect, the invention provides a process for producing a compound of formula (Ia) and/or (Ib) as defined above wherein the process is selected from any one of the following processes on the basis of compatibility of groups R$_1$, R$_2$, R$_3$, R$_4$, and R$_5$ with said process:

(a) reacting a compound of the formula (IIa)

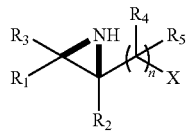
(IIa)

wherein n, R$_1$, R$_2$, R$_3$, R$_4$, and R$_5$ are as defined above and X is selected from

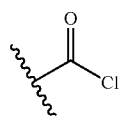 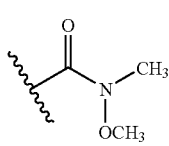 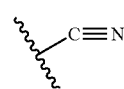

-continued

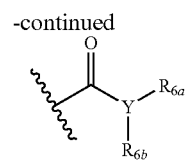 and wherein Y is oxygen or nitrogen, and
when Y is oxygen, R$_{6b}$ is absent, and R$_{6a}$ is selected from lower alkyl; aryl; and -loweralkyl-aryl, and
when Y is nitrogen, R$_{6a}$ and R$_{6b}$ are independently selected from hydrogen, lower alkyl; alkoxy; aryl; and -loweralkyl-aryl;
with a hydride transfer reagent to form the compound of formula (Ia) and/or (Ib) as defined above;
(b) reducing a compound of formula (IIb)

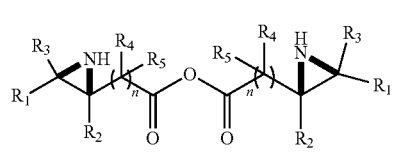
(IIb)

wherein n, R$_1$, R$_2$, R$_3$, R$_4$, and R$_5$ are as defined above to produce the compound of formula (Ia) and/or (Ib) as defined above;
(c) Fukuyama reduction of a compound of formula (IIc)

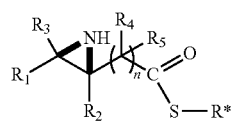
(IIc)

wherein n, R$_1$, R$_2$, R$_3$, R$_4$, and R$_5$ are as defined above and R* is selected from aryl; alkyl; heteroaryl; and heteroalkyl;
to produce the compound of formula (Ia) and/or (Ib) as defined above;
(d) oxidative cleavage of a compound of formula (IId)

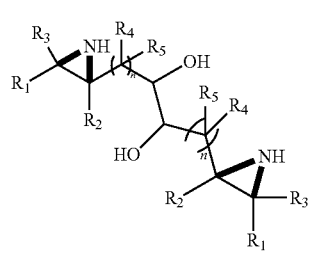
(IId)

wherein n, R$_1$, R$_2$, R$_3$, R$_4$, and R$_5$ are as defined above to produce the compound of formula (Ia) and/or (Ib) as defined above;
(e) oxidation of a compound of formula (IIe)

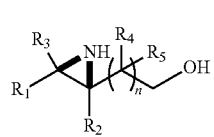
(IIe)

wherein n, $R_1$, $R_2$, $R_3$, $R_4$, and $R_5$ are as defined above to produce the compound of formula (Ia) and/or (Ib) as defined above; and (f) oxidative cleavage of a compound of formula (IIf)

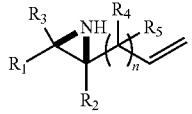

(IIf)

wherein n, $R_1$, $R_2$, $R_3$, $R_4$, and $R_5$ are as defined above to produce the compound of formula (Ia) and/or (Ib) as defined above.

In one aspect, process (a) is selected and X is

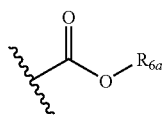

wherein $R_{6a}$ is selected from lower alkyl; aryl; and -loweralkyl-aryl.

In another aspect, the invention provides a novel aziridine ester compound selected from the group consisting of:

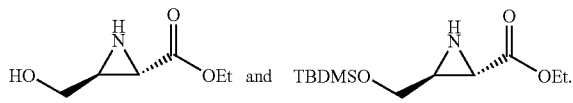

In another aspect, the invention provides a process for the preparation of an aziridine compound of formula (III):

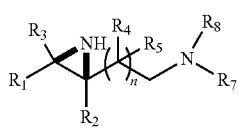

(III)

wherein n=0 or 1, and $R_1$, $R_2$, $R_3$, $R_4$ and $R_5$ are independently selected from H; lower alkyl; aryl; heteroaryl; alkenyl; cycloalkyl; heterocycle; esters of the formula —C(O)OR* wherein R* is selected from alkyl and aryl; amides of the formula —C(O)NRR*, wherein R and R* are independently selected from alkyl and aryl; —CH$_2$C(O)R, wherein R is selected from —OH, lower alkyl, aryl, -loweralkyl-aryl, or —NR$_a$R$_b$, where R$_a$ and R$_b$ are independently selected from H, lower alkyl, aryl or -loweralkyl-aryl; —C(O)R$_c$, wherein R$_c$ is selected from lower alkyl, aryl or -loweralkyl-aryl; or -lower alkyl-OR$_d$, wherein R$_d$ is a suitable protecting group;

and $R_7$ and $R_8$ are independently selected from H; lower alkyl; aryl; heteroaryl; cycloalkyl; -lower alkyl-alkenyl; and heterocycle;

all of which are optionally substituted at one or more substitutable positions with one or more suitable substituents, the process comprising coupling an aziridine aldehyde of formula (Ia) and/or (Ib):

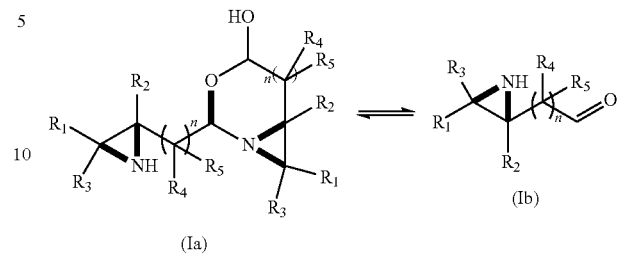

wherein n, $R_1$, $R_2$, $R_3$, $R_4$ and $R_5$ are as defined above, with an amine of formula (IV):

(IV)

wherein $R_7$ and $R_8$ are as defined above,
via reductive amination to yield the aziridine compound of formula (III).

In still another aspect, the invention provides a compound of formula (V)

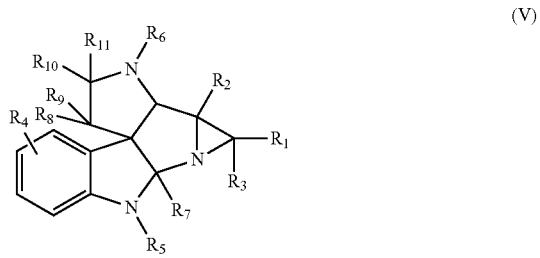

(V)

wherein $R_1$, $R_2$, and $R_3$ are independently selected from H; lower alkyl; aryl; heteroaryl; alkenyl; cycloalkyl; heterocycle; esters of the formula —C(O)OR* wherein R* is selected from alkyl and aryl; amides of the formula —C(O)NRR*, wherein R and R* are independently selected from alkyl and aryl; —CH$_2$C(O)R, wherein R is selected from —OH, lower alkyl, aryl, -loweralkyl-aryl, or —NR$_a$R$_b$, where R$_a$ and R$_b$ are independently selected from H, lower alkyl, aryl or -loweralkyl-aryl; —C(O)R$_c$, wherein R$_c$ is selected from lower alkyl, aryl or -loweralkyl-aryl; or -lower alkyl-OR$_d$ wherein R$_d$ is a suitable protecting group; each of the one or more $R_4$ substituents is independently selected from an electron neutral or electron donating group;

$R_5$ is selected from H; alkyl; hydroxyl; amino; -loweralkyl-aryl; and aryl;

$R_6$ is selected from alkyl; -loweralkyl-aryl; aryl; and hydroxyl;

$R_7$ is selected from H; alkyl; -loweralkyl-aryl; aryl; esters of the formula —C(O)OR* wherein R* is selected from alkyl and aryl; amides of the formula —C(O)NRR*, wherein R and R* are independently selected from alkyl and aryl; and —COOH;

$R_8$, $R_9$, $R_{10}$, and $R_{11}$ are independently selected from H; alkyl; hydroxyl; tertiary amino; acyl-amino; esters of the formula —C(O)OR* wherein R* is selected from alkyl and aryl; amides of the formula —C(O)NRR*, wherein R and R* are independently selected from alkyl and aryl; —COOH; thio; and aryl, all of which are optionally substituted at one or more substitutable positions with one or more suitable substituents.

In another aspect, the invention provides a compound selected from the group consisting of:

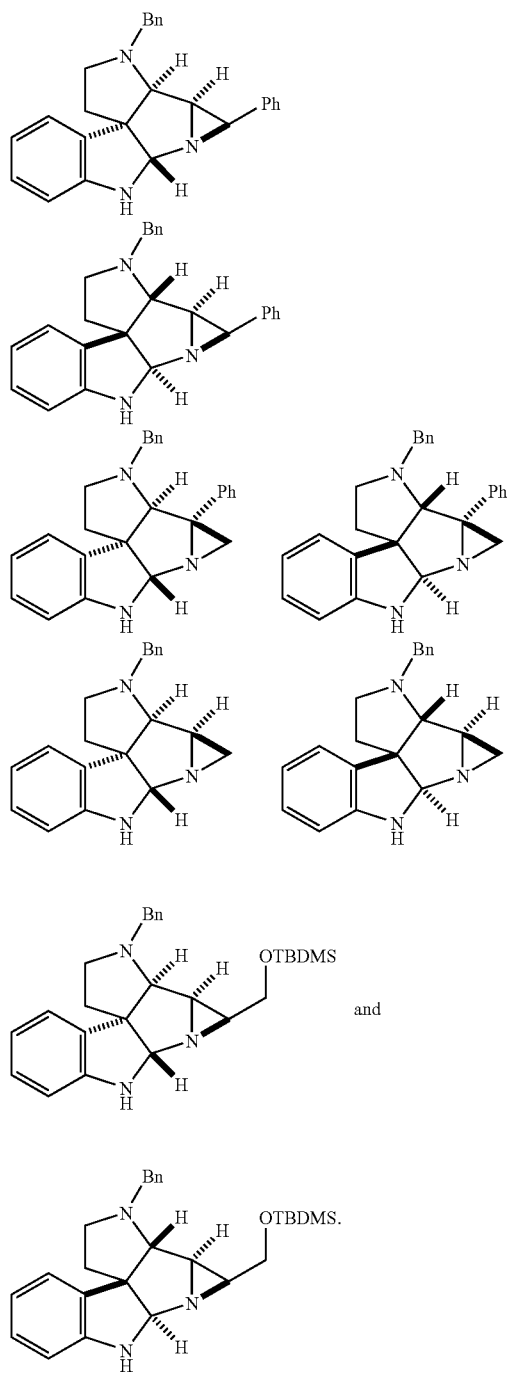

and

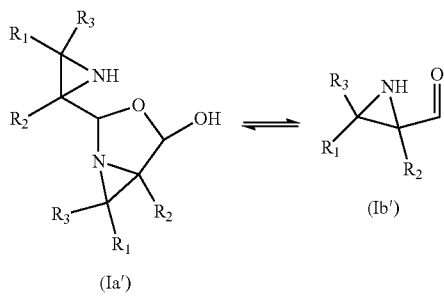

wherein $R_1$, $R_2$, and $R_3$ are independently selected from H; lower alkyl; aryl; heteroaryl; alkenyl; cycloalkyl; heterocycle; esters of the formula —C(O)OR* wherein R* is selected from alkyl and aryl; amides of the formula —C(O)NRR*, wherein R and R* are independently selected from alkyl and aryl; —CH$_2$C(O)R, wherein R is selected from —OH, lower alkyl, aryl, -loweralkyl-aryl, or —NR$_a$R$_b$, where R$_a$ and R$_b$ are independently selected from H, lower alkyl, aryl or -loweralkyl-aryl; —C(O)R$_c$, wherein R$_c$ is selected from lower alkyl, aryl or -loweralkyl-aryl; or -lower alkyl-OR$_d$, wherein R$_d$ is a suitable protecting group; all of which are optionally substituted at one or more substitutable positions with one or more suitable substituents, with a compound of formula (VI)

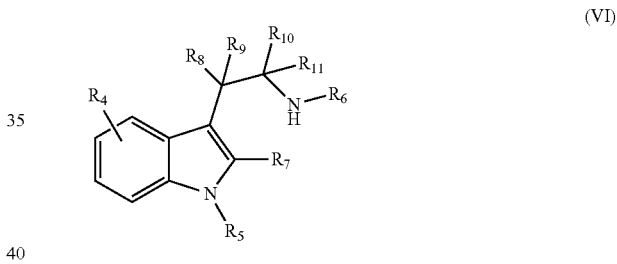

each of the one or more $R_4$ substituents is independently selected from an electron neutral or electron donating group;

$R_5$ is selected from H; alkyl; hydroxyl; amino; -loweralkyl-aryl; and aryl;

$R_6$ is selected from alkyl; -loweralkyl-aryl; aryl; and hydroxyl;

$R_7$ is selected from H; alkyl; -loweralkyl-aryl; aryl; esters of the formula —C(O)OR* wherein R* is selected from alkyl and aryl; amides of the formula —C(O)NRR*, wherein R and R* are independently selected from alkyl and aryl; and —COOH;

$R_8$, $R_9$, $R_{10}$, and $R_{11}$ are independently selected from H; alkyl; hydroxyl; tertiary amino; acyl-amino; esters of the formula —C(O)OR* wherein R* is selected from alkyl and aryl; amides of the formula —C(O)NRR*, wherein R and R* are independently selected from alkyl and aryl; —COOH; thio; and aryl, all of which are optionally substituted at one or more substitutable positions with one or more suitable substituents, to form the compound of formula (V).

In still another aspect, the invention provides a process for preparing a compound of formula (V) as defined above comprising reacting a compound of formula (Ia') and/or (Ib'):

In still another aspect, the invention provides a method for preparing an aziridine-conjugated bioactive molecule selected from an amino acid and peptide comprising coupling a suitably protected amino acid or peptide having a free amino group to a compound of formula (Ia) and/or (Ib) as defined above via reductive amination to form the aziridine-conjugated amino acid or peptide. In another aspect, the invention provides an aziridine-conjugated bioactive molecule prepared by this process.

In yet another aspect, the invention provides a process for preparing an aziridine-conjugated amino acid of formula (VII)

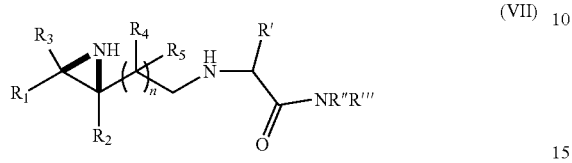

(VII)

wherein n=0 or 1, and $R_1$, $R_2$, $R_3$, $R_4$ and $R_5$ are independently selected from H; lower alkyl; aryl; heteroaryl; alkenyl; cycloalkyl; heterocycle; esters of the formula —C(O)OR* wherein R* is selected from alkyl and aryl; amides of the formula —C(O)NRR*, wherein R and R* are independently selected from alkyl and aryl; —CH$_2$C(O)R, wherein R is selected from —OH, lower alkyl, aryl, -loweralkyl-aryl, or —NR$_a$R$_b$, where R$_a$ and R$_b$ are independently selected from H, lower alkyl, aryl or -loweralkyl-aryl; —C(O)R$_c$, wherein R$_c$ is selected from lower alkyl, aryl or -loweralkyl-aryl; or -lower alkyl-OR$_d$, wherein R$_d$ is a suitable protecting group;

R' is selected from H; lower alkyl; aryl; heteroaryl; alkenyl; cycloalkyl; heterocycle; and -loweralkyl-aryl;

R" and R'" are selected from H; lower alkyl; aryl; heteroaryl; -lower alkyl-alkenyl; cycloalkyl; and heterocycle;

all of which are optionally substituted at one or more substitutable positions with one or more suitable substituents, the process comprising coupling an amino acid of formula (VIII)

(VIII)

wherein R', R", and R'" are as defined above with a compound of formula (Ia) and/or (Ib) as defined above via reductive amination to form the aziridine-conjugated amino acid of formula (VII). In another aspect, the invention provides an aziridine-conjugated amino acid prepared by this process.

In another aspect, the invention provides an aziridine-conjugated amino acid selected from the group consisting of:

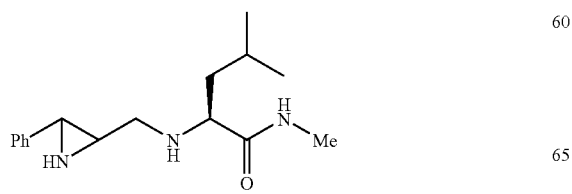

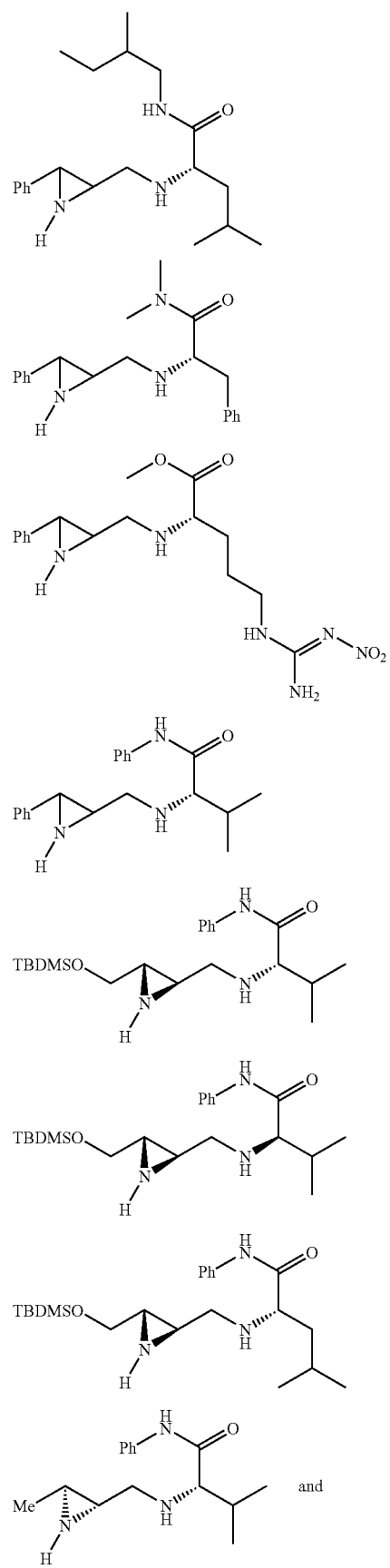

-continued

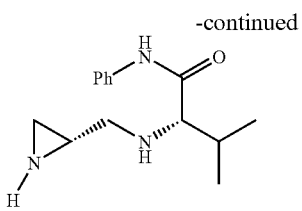

BRIEF DESCRIPTION OF THE FIGURES

FIGS. 2a and 2b illustrate the X-ray structure of aziridine aldehyde dimer 2a.

FIG. 4a illustrates the $^{13}$C NMR spectrum for of aziridine aldehyde dimer 2a.

DETAILED DESCRIPTION

As used in the context of the present invention, the various chemical terms are to be given their ordinary meaning as would be understood by persons skilled in the art, unless provided otherwise.

The following chemical terms presently described apply to all compounds and processes disclosed herein, unless provided otherwise.

Figure 3:
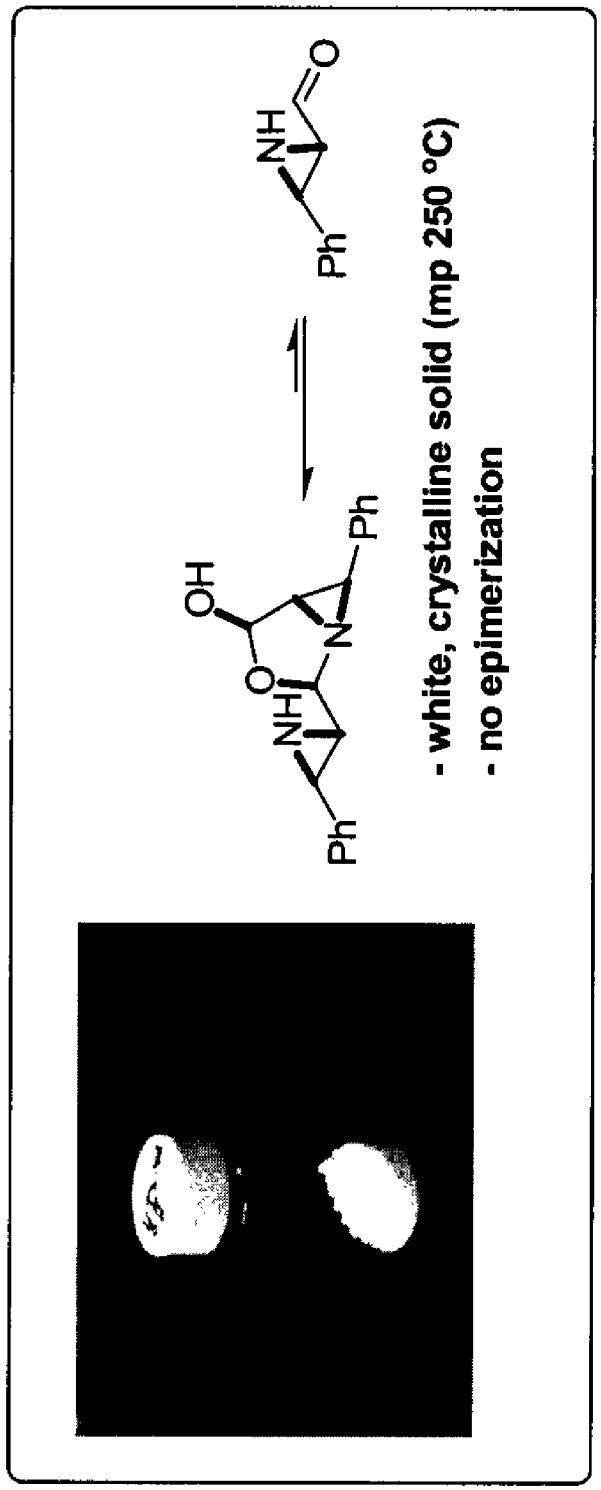
FIG. 3 illustrates the equilibrium between the dimer and monomer states of an aziridine aldehyde, and shows the aziridine aldehyde product as a white, crystalline solid.

The terms "aziridine aldehyde" and "amino aldehyde" are used interchangeably herein. These terms refer to both the dimers and monomers of these molecules, as an equilibrium exists between the dimer and monomer states (as shown in FIG. 3).

The term "suitable substituent" as used in the context of the present invention is meant to include independently H; hydroxyl; cyano; alkyl, such as lower alkyl, such as methyl, ethyl, propyl, n-butyl, t-butyl, hexyl and the like; alkoxy, such as lower alkoxy such as methoxy, ethoxy, and the like; aryloxy, such as phenoxy and the like; vinyl; alkenyl, such as hexenyl and the like; alkynyl; formyl; haloalkyl, such as lower haloalkyl which includes $CF_3$, $CCl_3$ and the like; halide; aryl, such as phenyl and napthyl; heteroaryl, such as thienyl and furanyl and the like; amide such as $C(O)NR_aR_b$, where $R_a$ and $R_b$ are independently selected from lower alkyl, aryl or benzyl, and the like; acyl, such as $C(O)—C_6H_5$, and the like; ester such as $—C(O)OCH_3$ the like; ethers and thio-ethers, such as O-Bn and the like; thioalkoxy; phosphino; and $—NR_aR_b$, where $R_a$ and $R_b$ are independently selected from lower alkyl, aryl or benzyl, and the like. It is to be understood that a suitable substituent as used in the context of the present invention is meant to denote a substituent that does not interfere with the formation of the desired product by the processes of the present invention.

As used in the context of the present invention, the term "lower alkyl" as used herein either alone or in combination with another substituent means acyclic, straight or branched chain alkyl substituent containing from one to six carbons and includes for example, methyl, ethyl, 1-methylethyl, 1-methylpropyl, 2-methylpropyl, and the like. A similar use of the term is to be understood for "lower alkoxy", "lower thioalkyl", "lower alkenyl" and the like in respect of the number of carbon atoms. For example, "lower alkoxy" as used herein includes methoxy, ethoxy, t-butoxy.

The term "alkyl" encompasses lower alkyl, and also includes alkyl groups having more than six carbon atoms, such as, for example, acyclic, straight or branched chain alkyl substituents having seven to ten carbon atoms.

The term "aryl" as used herein, either alone or in combination with another substituent, means an aromatic monocyclic system or an aromatic polycyclic system. For example, the term "aryl" includes a phenyl or a napthyl ring, and may also include larger aromatic polycyclic systems, such as fluorescent (e.g. anthracene) or radioactive labels and their derivatives.

The term "heteroaryl" as used herein, either alone or in combination with another substituent means a 5, 6, or 7-membered unsaturated heterocycle containing from one to 4 heteroatoms selected from nitrogen, oxygen, and sulphur and which form an aromatic system. The term "heteroaryl" also includes a polycyclic aromatic system comprising a 5, 6, or 7-membered unsaturated heterocycle containing from one to 4 heteroatoms selected from nitrogen, oxygen, and sulphur.

The term "cycloalkyl" as used herein, either alone or in combination with another substituent, means a cycloalkyl substituent that includes for example, but is not limited to, cyclopropyl, cyclobutyl, cyclopentyl, cyclohexyl and cycloheptyl.

The term "cycloalkyl-alkyl-" as used herein means an alkyl radical to which a cycloalkyl radical is directly linked; and includes, but is not limited to, cyclopropylmethyl, cyclobutylmethyl, cyclopentylmethyl, 1-cyclopentylethyl, 2-cyclopentylethyl, cyclohexylmethyl, 1-cyclohexylethyl and 2-cyclohexylethyl. A similar use of the "alkyl" or "lower alkyl" terms is to be understood for aryl-alkyl-, aryl-loweralkyl- (e.g. benzyl), -lower alkyl-alkenyl (e.g. allyl), heteroarylalkyl-, and the like as used herein. For example, the term "aryl-alkyl-" means an alkyl radical, to which an aryl is bonded. Examples of aryl-alkyl- include, but are not limited to, benzyl(phenylmethyl), 1-phenylethyl, 2-phenylethyl and phenylpropyl.

As used herein, the term "heterocycle", either alone or in combination with another radical, means a monovalent radical derived by removal of a hydrogen from a three- to seven-membered saturated or unsaturated (including aromatic) heterocycle containing from one to four heteroatoms selected from nitrogen, oxygen and sulfur. Examples of such heterocycles include, but are not limited to, aziridine, epoxide, azetidine, pyrrolidine, tetrahydrofuran, thiazolidine, pyrrole, thiophene, hydantoin, diazepine, imidazole, isoxazole, thiazole, tetrazole, piperidine, piperazine, homopiperidine, homo-piperazine, 1,4-dioxane, 4-morpholine, 4-thiomorpholine, pyridine, pyridine-N-oxide or pyrimidine, and the like.

The term "alkenyl", as used herein, either alone or in combination with another radical, is intended to mean an unsaturated, acyclic straight chain radical containing two or more carbon atoms, at least two of which are bonded to each other by a double bond. Examples of such radicals include, but are not limited to, ethenyl (vinyl), 1-propenyl, 2-propenyl, and 1-butenyl.

The term "alkynyl", as used herein is intended to mean an unsaturated, acyclic straight chain radical containing two or more carbon atoms, at least two of which are bonded to each other by a triple bond. Examples of such radicals include, but are not limited to, ethynyl, 1-propynyl, 2-propynyl, and 1-butynyl.

The term "alkoxy" as used herein, either alone or in combination with another radical, means the radical —O—($C_{1-n}$)alkyl wherein alkyl is as defined above containing 1 or more carbon atoms, and includes for example methoxy, ethoxy, propoxy, 1-methylethoxy, butoxy and 1,1-dimethylethoxy. Where n is 1 to 6, the term "lower alkoxy" applies, as noted above, whereas the term "alkoxy" encompasses "lower alkoxy" as well as alkoxy groups where n is greater than 6 (for example, n=7 to 10). The term "aryloxy" as used herein alone or in combination with another radical means —O-aryl, wherein aryl is defined as noted above.

As used herein the term "heteroatom" means O, S, P or N.

In one embodiment, the invention provides a compound of formula (Ia) and/or (Ib):

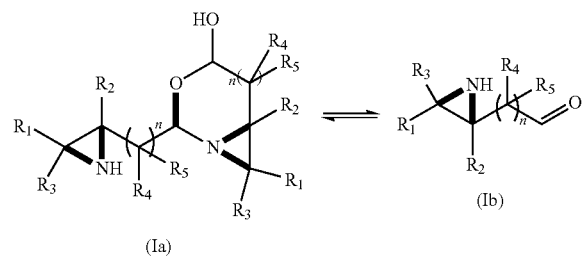

(Ia)

(Ib)

wherein n=0 or 1, and $R_1$, $R_2$, $R_3$, $R_4$ and $R_5$ are independently selected from H; lower alkyl; aryl; heteroaryl; alkenyl; cycloalkyl; heterocycle; esters of the formula —C(O)OR* wherein R* is selected from alkyl and aryl; amides of the formula —C(O)NRR*, wherein R and R* are independently selected from alkyl and aryl; —$CH_2$C(O)R, wherein R is selected from —OH, lower alkyl, aryl, -loweralkyl-aryl, or $NR_aR_b$, where $R_a$ and $R_b$ are independently selected from H, lower alkyl, aryl or -loweralkyl-aryl; —C(O)$R_c$, wherein $R_c$ is selected from lower alkyl, aryl or -loweralkyl-aryl; or -lower alkyl-$OR_d$, wherein $R_d$ is a suitable protecting group;

all of which are optionally substituted at one or more substitutable positions with one or more suitable substituents, with the proviso that when $R_2$ is phenyl, $R_3$ is methyl, and n=0 then $R_1$ cannot be —C(O)$NEt_2$. In another embodiment, n=0, $R_1$ and $R_3$ are independently selected from H; aryl; heteroaryl; and -lower alkyl-$OR_d$, wherein $R_d$ is a suitable protecting group, and $R_2$ is selected from H and aryl.

In yet another embodiment, the invention provides a compound selected from the group consisting of:

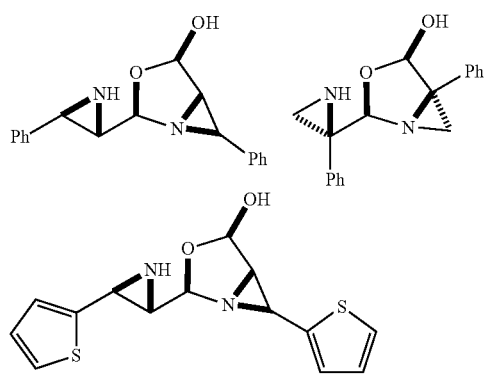

-continued

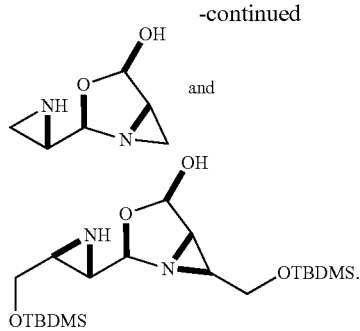

Suitable hydroxyl protecting groups ("$R_d$" as noted above, and throughout this text) are known to those of skill in the art. Such protecting groups are selected to be compatible with the reaction conditions, and include silyl based protecting groups such as TBDMS, ethers such as benzyl ether, hemiacetal such as THP, etc. Suitable protecting groups are set forth in *Greene's Protective Groups in Organic Synthesis, Fourth Edition* (Peter G. M. Wuts and Theodora W. Greene Copyright 2007 John Wiley & Sons, Inc.), the contents of which are incorporated herein by reference in this regard.

The compounds of formula (Ia) and/or (Ib) as defined above may be prepared by a variety of processes. Those of skill in the art will readily understand that the choice of process and the choice of process conditions (temperature, reagents, etc.) are dependent on the nature of the $R_1$-$R_5$ groups, and that certain substituents will not tolerate certain reaction conditions. Appropriate process conditions are set forth in Larock, R. C. "Comprehensive Organic Transformations: A Guide to Functional Group Preparations" 1989, VCH Publishers Inc. New York, the contents of which are incorporated herein by reference in this regard.

In one embodiment, the invention provides a process for producing a compound of formula (Ia) and/or (Ib) as defined above wherein the process is selected from any one of the following processes on the basis of compatibility of groups $R_1$, $R_2$, $R_3$, $R_4$, and $R_5$ with said process:

Process (a): reacting a compound of the formula (IIa)

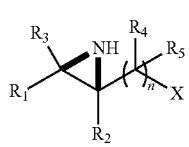

(IIa)

wherein n, $R_1$, $R_2$, $R_3$, $R_4$, and $R_5$ are as defined above and X is selected from

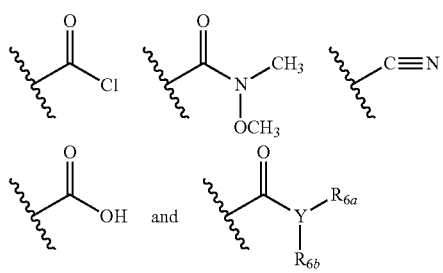

wherein Y is oxygen or nitrogen, and
when Y is oxygen, $R_{6b}$ is absent, and $R_{6a}$ is selected from lower alkyl; aryl; and -loweralkyl-aryl, and
when Y is nitrogen, $R_{6a}$ and $R_{6b}$ are independently selected from hydrogen, lower alkyl; alkoxy; aryl; and -loweralkyl-aryl;
with a hydride transfer reagent to form the compound of formula (Ia) and/or (Ib) as defined above.

When X is —C(O)Cl, diisobutylaluminum hydride (DIBAL) may be used as the hydride transfer reagent. Under these conditions, $R_1$-$R_5$ cannot be an ester group.

When X is

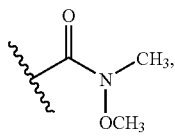

LiAlH$_4$ may be used as the hydride transfer reagent. Under these conditions, $R_1$-$R_5$ cannot be an ester group.

When X is —C≡N, DIBAL may be used as the hydride transfer reagent. Under these conditions, $R_1$-$R_5$ cannot be an ester group.

When X is —C(O)OH, borohydride reagents or LiAlH$_4$ may be used as the hydride transfer reagent. Under these conditions, $R_1$-$R_5$ cannot be an ester group or —CH$_2$C(O)R, wherein R is selected from —OH.

When X is

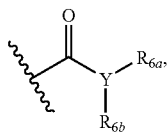

DIBAL may be used as the hydride transfer reagent.

Process (b): reducing a compound of formula (IIb)

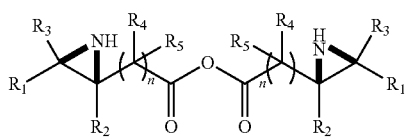

(IIb)

wherein n, $R_1$, $R_2$, $R_3$, $R_4$, and $R_5$ are as defined above to produce the compound of formula (Ia) and/or (Ib) as defined above;

In the case of process (b), typical reaction conditions are −78° C. to −30° C. in nonpolar solvents such as toluene for 1-10 hours, with dropwise addition of a reducing agent over one hour. Conditions used for the reduction of aziridine anhydrides are not compatible with ester groups, thus, $R_1$-$R_5$ cannot be an ester group.

Process (c): Fukuyama reduction of a compound of formula (IIc)

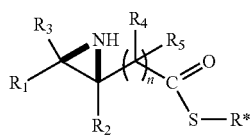

(IIc)

wherein n, $R_1$, $R_2$, $R_3$, $R_4$, and $R_5$ are as defined above and R* is selected from aryl; alkyl; heteroaryl; and heteroalkyl; to produce the compound of formula (Ia) and/or (Ib) as defined above;

Process (d): oxidative cleavage of a compound of formula (IId)

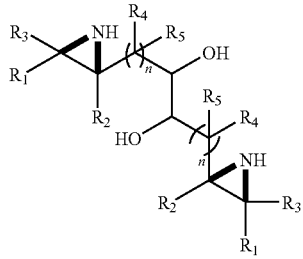

(IId)

wherein n, $R_1$, $R_2$, $R_3$, $R_4$, and $R_5$ are as defined above to produce the compound of formula (Ia) and/or (Ib) as defined above;

In the case of process (d), substituents containing diols should obviously be avoided. In one embodiment o-iodoxybenzoic acid (IBX) is used to effect oxidative cleavage of the compounds of formula (IId) to produce the compounds of formula (Ia) and/or (Ib).

Process (e): oxidation of a compound of formula (IIe)

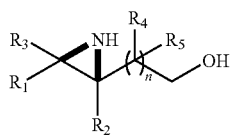

(IIe)

wherein n, $R_1$, $R_2$, $R_3$, $R_4$, and $R_5$ are as defined above to produce the compound of formula (Ia) and/or (Ib) as defined above;

In the case of process (e), alcohol substituents should obviously be avoided.

Process (f): oxidative cleavage of a compound of formula (IIf)

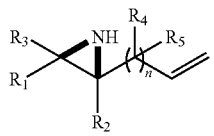

(IIf)

wherein n, $R_1$, $R_2$, $R_3$, $R_4$, and $R_5$ are as defined above to produce the compound of formula (Ia) and/or (Ib) as defined above.

In the case of process (f), oxidative cleavage of vinyl aziridines may be effected using conditions set forth in Gang Chen, Mikio Sasaki, Xinghan Li, and Andrei K. Yudin* *J. Org. Chem.*, 71 (16), 6067-6073, 2006 (Scheme 6):

Scheme 6

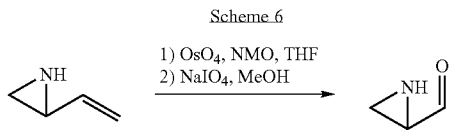

As would be apparent to a person of skill in the art, when process (f) is used, $R_1$-$R_5$ cannot be alkenyl.

In one embodiment, the compounds of formula (Ia) and/or (Ib) are prepared using process (a), and the compounds of formula (IIa) are corresponding aziridine esters wherein X is —C(O)OR$_{6a}$, i.e.:

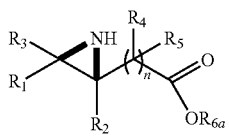

wherein R$_{6a}$ is selected from lower alkyl; aryl; and -lower-alkyl-aryl.

The following description of the processes for preparing the aziridine aldehydes of formula (Ia) and/or (Ib) relates to the preparation of these compounds from corresponding aziridine esters of the formula

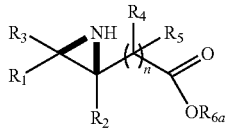

wherein $R_1$, $R_2$, $R_3$, $R_4$, $R_5$, and $R_{6a}$ are as defined above.

A person of skill in the art would readily understand that where any of $R_1$ to $R_5$ are selected from esters of the formula —C(O)OR* wherein R* is selected from alkyl and aryl or amides of the formula —C(O)NRR*, wherein R and R* are independently selected from alkyl and aryl, a variety of ester and amide groups are compatible with the reaction conditions used to produce the aziridine aldehydes of formula (Ia) and/or (Ib) from their corresponding aziridine esters. Such groups may be selected on the basis of their relative rates of reduction as compared to the rate of reduction of the moiety —C(O)OR$_a$.

Suitable solvents for use in process (a) for the preparation of aziridine aldehydes from their corresponding aziridine esters are aprotic solvents including, but not limited to, toluene, benzene, and ethers. Any solvent may be used provided that it does not interfere with the formation of the desired product. Typically, the hydride transfer reagent is added in small portions to a cooled solution of an aziridine ester starting material. Air can be removed from the reaction vessel during the course of the reaction and the solvent and reaction mixtures can be sparged with a non-reactive gas.

Hydride transfer reagents for use in the processes for preparing aziridine aldehydes from their corresponding aziridine esters include but are not limited to DIBAL (diisobutylaluminum hydride), sodium diethylpiperidinohydroaluminate (SDPA), lithium diisobutylpiperidinohydroaluminate (LDBPA), sodium bis(2-methoxyethoxy)aluminum hydride (SBMEA), and sodium aluminum hydride. In one embodiment, the hydride transfer reagent is DIBAL.

The process conditions for the preparation of aziridine aldehydes from their corresponding aziridine esters can be any operable conditions which yield the desired product. A preferred temperature for the processes for the production of the aziridine aldehydes from their corresponding aziridine esters is about −78° C., although it is envisioned that temperatures ranging from about −35° C. to −78° C. could be used. Temperatures can be higher or lower depending upon the reagents, reaction conditions and the solvent used. Typical reaction times are generally between about 1 and 7 hours, although longer or shorter times may be used if necessary.

The aziridine aldehyde products of formula (Ia) and/or (Ib), regardless of the process by which they are made, can be recovered by conventional methods known to those skilled in the art, for example crystallization and silica gel chromatography, unless otherwise stated. The yield of the aziridine aldehyde product will vary depending upon the starting materials and process conditions used. Typically, the desired aziridine aldehydes are provided in a yield greater than 70%, preferably in a yield of greater than 80%. In some cases, a yield greater than 90% is obtained.

In another embodiment, the invention provides a novel aziridine ester compound selected from the group consisting of:

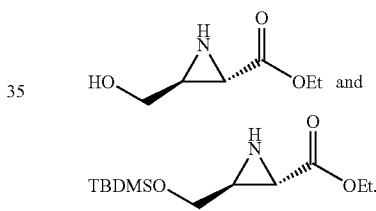

In another embodiment, the invention provides a process for the preparation of an aziridine compound of formula (III):

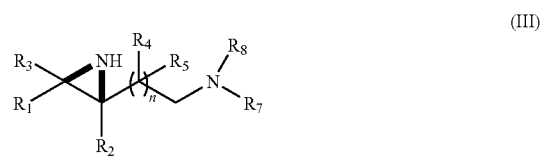

(III)

wherein n=0 or 1, and $R_1$, $R_2$, $R_3$, $R_4$ and $R_5$ are independently selected from H; lower alkyl; aryl; heteroaryl; alkenyl; cycloalkyl; heterocycle; esters of the formula —C(O)OR* wherein R* is selected from alkyl and aryl; amides of the formula —C(O)NRR*, wherein R and R* are independently selected from alkyl and aryl; —CH$_2$C(O)R, wherein R is selected from —OH, lower alkyl, aryl, -lower-alkyl-aryl, or NR$_a$R$_b$, where R$_a$ and R$_b$ are independently selected from H, lower alkyl, aryl or -loweralkyl-aryl; —C(O)R$_c$, wherein R$_c$ is selected from lower alkyl, aryl or -lower-alkyl-aryl; or -lower alkyl-OR$_d$, wherein R$_d$ is a suitable protecting group;

and R$_7$ and R$_8$ are independently selected from H; lower alkyl; aryl; heteroaryl; cycloalkyl; -lower alkyl-alkenyl; and heterocycle;

all of which are optionally substituted at one or more substitutable positions with one or more suitable substituents,
the process comprising coupling an aziridine aldehyde of formula (Ia) and/or (Ib):

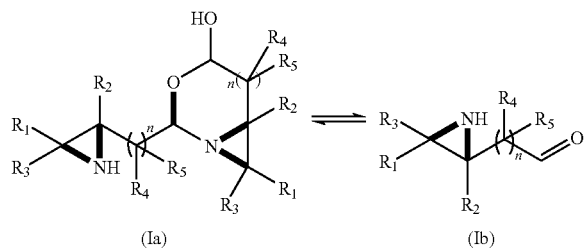

wherein n, $R_1$, $R_2$, $R_3$, $R_4$ and $R_5$ are as defined above, with an amine of formula (IV):

wherein $R_7$ and $R_8$ are as defined above,
via reductive amination to yield the aziridine compound of formula (III).

In another embodiment, the invention provides a compound of formula (V)

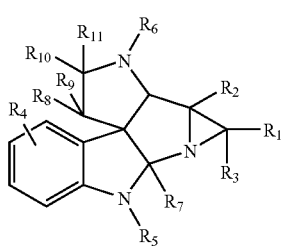

wherein $R_1$, $R_2$, and $R_3$ are independently selected from H; lower alkyl; aryl; heteroaryl; alkenyl; cycloalkyl; heterocycle; esters of the formula —C(O)OR* wherein R* is selected from alkyl and aryl; amides of the formula —C(O)NRR*, wherein R and R* are independently selected from alkyl and aryl; —CH$_2$C(O)R, wherein R is selected from —OH, lower alkyl, aryl, -loweralkyl-aryl, or —NR$_a$R$_b$, where R$_a$ and R$_b$ are independently selected from H, lower alkyl, aryl or -loweralkyl-aryl; —C(O)R$_c$, wherein R$_c$ is selected from lower alkyl, aryl or -loweralkyl-aryl; or -lower alkyl-OR$_d$, wherein R$_d$ is a suitable protecting group; each of the one or more $R_4$ substituents is independently selected from an electron neutral or electron donating group;
$R_5$ is selected from H; alkyl; hydroxyl; amino; -loweralkyl-aryl; and aryl;
$R_6$ is selected from alkyl; -loweralkyl-aryl; aryl; and hydroxyl;
$R_7$ is selected from H; alkyl; -loweralkyl-aryl; aryl; esters of the formula —C(O)OR* wherein R* is selected from alkyl and aryl; amides of the formula —C(O)NRR*, wherein R and R* are independently selected from alkyl and aryl; and —COOH;

$R_8$, $R_9$, $R_{10}$, and $R_{11}$ are independently selected from H; alkyl; hydroxyl; tertiary amino; acyl-amino; esters of the formula —C(O)OR* wherein R* is selected from alkyl and aryl; amides of the formula —C(O)NRR*, wherein R and R* are independently selected from alkyl and aryl; —COOH; thio; and aryl,
all of which are optionally substituted at one or more substitutable positions with one or more suitable substituents.

Examples of suitable $R_4$ groups for the compounds of formula (V) include but are not limited to H, alkyl, aryl, hydroxyl, amino, thio, etc. and there can be up to four $R_4$ groups independently selected from such electron neutral or electron donating groups. Thus, in certain embodiments a compound of formula (V) may have two or more $R_4$ substituents that are the same or different from one another.

In another embodiment, the invention provides a compound of formula (V) wherein $R_1$ and $R_3$ are independently selected from H; aryl; and -lower alkyl-OR$_d$, wherein R$_d$ is a suitable protecting group; $R_2$ is selected from H and aryl; $R_6$ is -loweralkyl-aryl; and $R_4$, $R_5$, $R_7$, $R_8$, $R_9$, $R_{10}$, and $R_{11}$ are H.

In another embodiment, the invention provides a compound selected from the group consisting of:

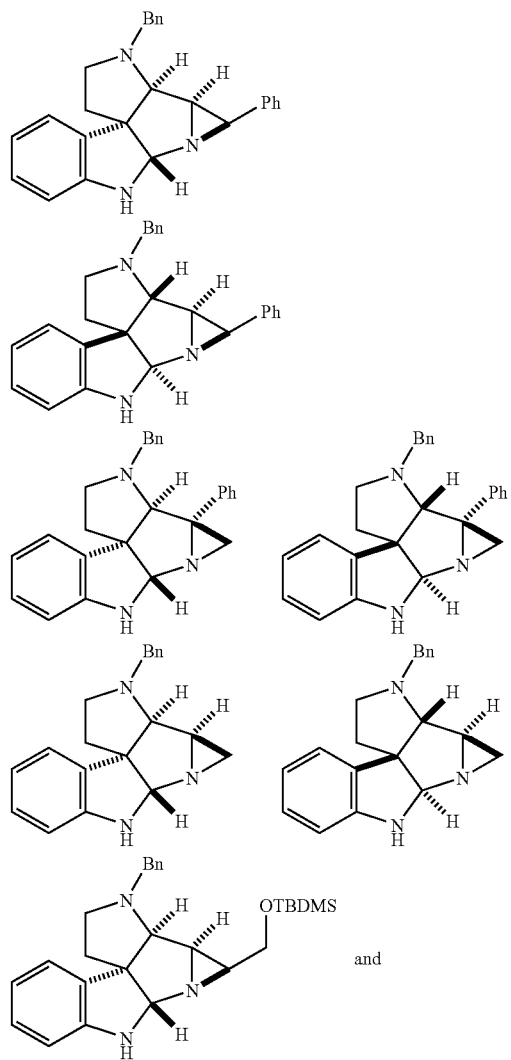

-continued

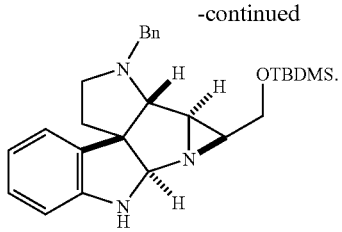

In another embodiment, the invention provides a process for preparing a compound of formula (V) as defined above comprising reacting a compound of formula (Ia') and/or (Ib'):

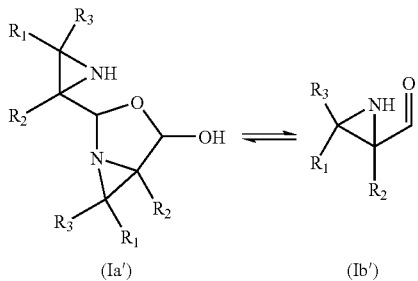

wherein $R_1$, $R_2$, and $R_3$ are independently selected from H; lower alkyl; aryl; heteroaryl; alkenyl; cycloalkyl; heterocycle; esters of the formula —C(O)OR* wherein R* is selected from alkyl and aryl; amides of the formula —C(O)NRR*, wherein R and R* are independently selected from alkyl and aryl; —CH$_2$C(O)R, wherein R is selected from —OH, lower alkyl, aryl, -loweralkyl-aryl, or —NR$_a$R$_b$, where R$_a$ and R$_b$ are independently selected from H, lower alkyl, aryl or -loweralkyl-aryl; —C(O)R$_c$, wherein R$_c$ is selected from lower alkyl, aryl or -loweralkyl-aryl; or -lower alkyl-OR$_d$, wherein R$_d$ is a suitable protecting group; all of which are optionally substituted at one or more substitutable positions with one or more suitable substituents, with a compound of formula (VI)

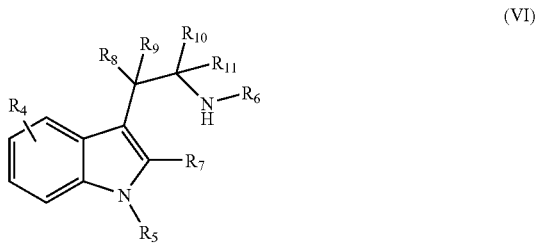

each of the one or more $R_4$ substituents is independently selected from an electron neutral or electron donating group;

$R_5$ is selected from H; alkyl; hydroxyl; amino; -loweralkyl-aryl; and aryl;

$R_6$ is selected from alkyl; -loweralkyl-aryl; aryl; and hydroxyl;

$R_7$ is selected from H; alkyl; -loweralkyl-aryl; aryl; esters of the formula —C(O)OR* wherein R* is selected from alkyl and aryl; amides of the formula —C(O)NRR*, wherein R and R* are independently selected from alkyl and aryl; and —COOH;

$R_8$, $R_9$, $R_{10}$, and $R_{11}$ are independently selected from H; alkyl; hydroxyl; tertiary amino; acyl-amino; esters of the formula —C(O)OR* wherein R* is selected from alkyl and aryl; amides of the formula —C(O)NRR*, wherein R and R* are independently selected from alkyl and aryl; —COOH; thio; and aryl, all of which are optionally substituted at one or more substitutable positions with one or more suitable substituents, to form the compound of formula (V).

Any solvent may be used in the processes of the present invention for the preparation of pentacycles of formula (V) from aziridine aldehydes of formula (Ia') and/or (Ib') and tryptamine derivatives of formula (VI), provided that it does not interfere with the formation of the desired product. A suitable solvent includes but is not limited to trifluoroethanol if reactions are carried out at room temperature. Toluene may also be used as a solvent, although elevated temperatures may be required.

The tryptamine derivative may be added in small portions to a solution of the aziridine aldehyde or vice versa. Air can be removed from the reaction vessel during the course of the reaction and the solvent and reaction mixtures can be sparged with a non-reactive gas.

The process conditions for the preparation of pentacycles derived from aziridine aldehydes and tryptamine derivatives can be any operable conditions which yield the desired product. In certain embodiments, temperatures for the processes for the production of the pentacycles of the present invention range from about −20° C. to 40° C., although these temperatures can be higher or lower depending upon the reagents, reaction conditions and the solvent used. Typical reaction times are between 3 and 8 hours, although longer or shorter times may be used if necessary.

The pentacycles derived from aziridine aldehydes and tryptamine derivatives can be recovered by conventional methods known to those skilled in the art, for example crystallization and silica gel chromatography, unless otherwise stated. The yield of the pentacycle products will vary depending upon the starting materials and process conditions used. The desired pentacycles are generally provided in a yield greater than 70%. In some cases, a yield greater than 90% is obtained.

In still another embodiment, the invention provides a method for preparing an aziridine-conjugated bioactive molecule selected from an amino acid and peptide comprising coupling a suitably protected amino acid or peptide having a free amino group to a compound of formula (Ia) and/or (Ib) as defined above via reductive amination to form the aziridine-conjugated amino acid or peptide.

In one embodiment, the reductive amination conditions are selected from the following based on the solubility and stability of the bioactive molecule under said conditions:

NaCNBH$_3$, methanol, acetic acid (1% in methanol);

NaCNBH$_3$, methanol;

NaCNBH$_3$/Ce(SO$_4$)$_2$, methanol/dichloromethane (1/1);

NaCNBH$_3$/PbBr$_2$, methanol/dichloromethane (1/1);

NaCNBH$_3$/ZnCl$_2$, methanol/dichloromethane (1/1);

NaCNBH$_3$/ZnCl$_2$, methanol/tetrahydrofuran (1/1);

NaCNBH$_3$/ZnCl$_2$, methanol/diethyl ether (1/1); and

NaCNBH$_3$/ZnCl$_2$, methanol/toluene (1/1).

In another embodiment, the bioactive molecule is a suitably protected amino acid and the reductive amination conditions are NaCNBH$_3$/ZnCl$_2$, methanol/tetrahydrofuran (1/1).

In another embodiment, the invention provides an aziridine-conjugated amino acid or peptide prepared by the above process.

In yet another embodiment, the invention provides a process for preparing an aziridine-conjugated amino acid of formula (VII)

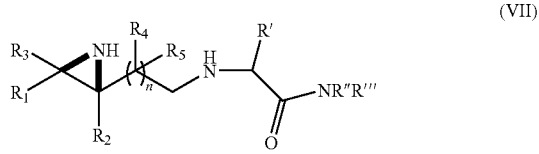

(VII)

wherein n=0 or 1, and R$_1$, R$_2$, R$_3$, R$_4$ and R$_5$ are independently selected from H; lower alkyl; aryl; heteroaryl; alkenyl; cycloalkyl; heterocycle; esters of the formula —C(O)OR* wherein R* is selected from alkyl and aryl; amides of the formula —C(O)NRR*, wherein R and R* are independently selected from alkyl and aryl; —CH$_2$C(O)R, wherein R is selected from —OH, lower alkyl, aryl, -loweralkyl-aryl, or —NR$_a$R$_b$, where R$_a$ and R$_b$ are independently selected from H, lower alkyl, aryl or -loweralkyl-aryl; —C(O)R$_c$, wherein R$_c$ is selected from lower alkyl, aryl or -loweralkyl-aryl; or -lower alkyl-OR$_d$, wherein R$_d$ is a suitable protecting group;

R' is selected from H; lower alkyl; aryl; heteroaryl; alkenyl; cycloalkyl; heterocycle; and -loweralkyl-aryl;

R" and R'" are selected from H; lower alkyl; aryl; heteroaryl; -lower alkyl-alkenyl; cycloalkyl; and heterocycle; all of which are optionally substituted at one or more substitutable positions with one or more suitable substituents, the process comprising coupling an amino acid of formula (VIII)

(VIII)

wherein R', R", and R'" are as defined above
with a compound of formula (Ia) and/or (Ib) as defined above via reductive amination to form the aziridine-conjugated amino acid of formula (VII).

In one embodiment, the reductive amination conditions are selected from the following:

NaCNBH$_3$, methanol, acetic acid (1% in methanol);

NaCNBH$_3$, methanol;

NaCNBH$_3$/Ce(SO$_4$)$_2$, methanol/dichloromethane (1/1);

NaCNBH$_3$/PbBr$_2$, methanol/dichloromethane (1/1);

NaCNBH$_3$/ZnCl$_2$, methanol/dichloromethane (1/1);

NaCNBH$_3$/ZnCl$_2$, methanol/tetrahydrofuran (1/1);

NaCNBH$_3$/ZnCl$_2$, methanol/diethyl ether (1/1); and

NaCNBH$_3$/ZnCl$_2$, methanol/toluene (1/1).

In still another embodiment, the reductive amination conditions are NaCNBH$_3$/ZnCl$_2$, methanol/tetrahydrofuran (1/1).

In another embodiment, the invention provides an aziridine-conjugated amino acid prepared by the above process.

In yet another embodiment, the invention provides an aziridine-conjugated amino acid selected from the group consisting of:

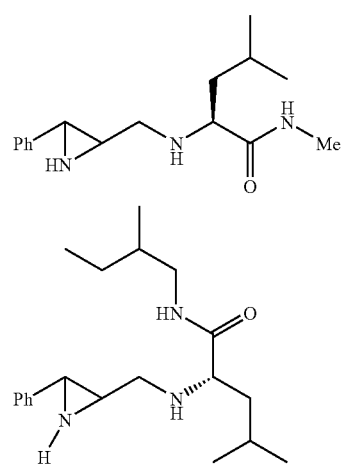

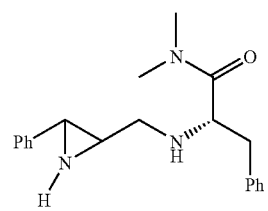

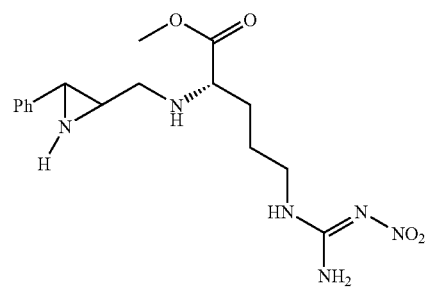

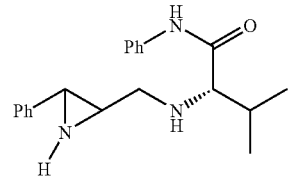

-continued

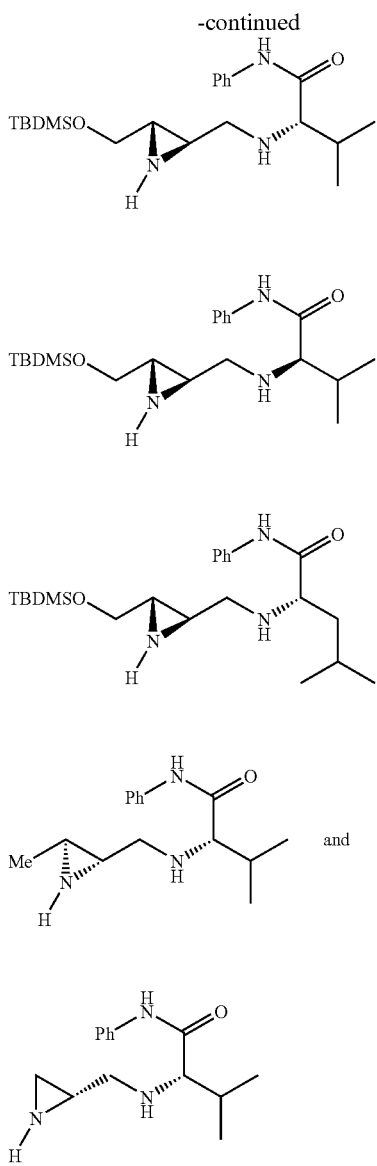

and

In still another embodiment, the invention provides for the use of aziridine-conjugated amino acids and peptides prepared by the above processes for peptidomimetic ligation.

The term "amino acid" is meant to include not only the twenty amino acids commonly found in proteins but also non-standard amino acids and unnatural amino acid derivatives known to those of skill in the art. Peptides of the present invention may include standard, non-standard, and unnatural amino acids. Any amino acids containing a free amino group corresponding to a primary (alkyl-NH$_2$) or secondary ((alkyl)$_2$NH) amino group may be used in the processes of the present invention. Any peptide may be used as well, but for optimal selectivity there should only be one free primary or secondary amino group. It will be understood by a person of skill in the art that free amino groups of side chains of amino acid such as lysine should be protected using protecting groups that are compatible with reductive amination conditions, such as Cbz, and Boc.

Peptides of interest can be purchased from known suppliers or prepared by standard synthetic procedures. Amino acid and peptides may be modified or purchased with suitable protecting groups known to those of skill in the art, and such protecting groups may be removed according to standard chemical procedures known to those of skill in the art.

Any solvent may be used in the processes of the present invention for the preparation of aziridine-conjugated amino acids and peptides, provided that it does not interfere with the formation of the desired product. Suitable solvents include, but are not limited to, THF/MeOH, MeOH, 2-methyl THF, and the like. Those skilled in the art will recognize that the choice of solvent will depend on the amino acid or peptide used in the reaction.

Typically, in the processes for the preparation of aziridine-conjugated amino acids and peptides via reductive amination, the reducing agents are added to a solution of the aziridine aldehyde and amino acid or peptide starting materials. In one embodiment, the reducing agent may be NaCNBH$_3$ in combination with Ce(SO$_4$)$_2$, PbBr$_2$, or ZnCl$_2$, and the like. Air can be removed from the reaction vessel during the course of the reaction and the solvent and reaction mixtures can be sparged with a non-reactive gas.

The process conditions for the preparation of aziridine-conjugated amino acids and peptides can be any operable conditions which yield the desired product. A preferred temperature for the processes for the production of the aziridine-conjugated amino acids and peptides of the present invention is room temperature, although this temperature can be higher or lower depending upon the reagents, reaction conditions and the solvent used. Typical reaction times are between 12-16 hours, although longer or shorter times may be used if necessary.

The aziridine-conjugated amino acids and peptides can be recovered by conventional methods known to those skilled in the art, for example crystallization and silica gel chromatography, unless otherwise stated. The yield of the aziridine-conjugated products will vary depending upon the starting materials and process conditions used. The desired aziridine-conjugated products are generally provided in a yield greater than 50%, preferably in a yield of greater than 75%. In some cases, a yield greater than 90% is obtained.

In other embodiments, the invention provides a process for the preparation of an aziridine-conjugated bioactive molecule, wherein the bioactive molecule comprises a primary or secondary amino group, or a carbamoyl group, or the bioactive molecule comprises a covalent linkage to a linker containing said primary or secondary amino group or carbamoyl group, said process comprising coupling the bioactive molecule with an aziridine aldehyde of formula (Ia) and/or (Ib):

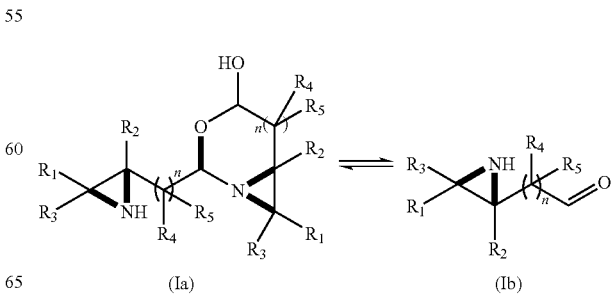

(Ia)           (Ib)

wherein n, $R_1$, $R_2$, $R_3$, $R_4$ and $R_5$ are as defined above, via reductive amination to yield the aziridine-conjugated bioactive molecule.

In one embodiment, the bioactive molecule is selected from the group comprising natural and un-natural amino acids, peptides, proteins and enzymes; natural and non-natural nucleotide/side base, DNA, RNA and aptamers; co-factors; antibodies; sugars, wherein the sugars are unable to undergo mutarotation; steroids, terpenoids, and polyketides; and FDA-approved pharmaceuticals containing amine functionalities or functional groups capable of covalent linkage to the linker as defined above.

In another embodiment, the invention provides an aziridine-conjugated bioactive molecule obtained by the above processes.

In still another embodiment, the invention provides a process for preparing an aziridine-conjugated bioactive molecule, wherein the bioactive molecule comprises an electrophile or said bioactive molecule comprises a covalent linkage to a linker containing said electrophile, said process comprising coupling the bioactive molecule with an aziridine aldehyde of formula (Ia) and/or (Ib):

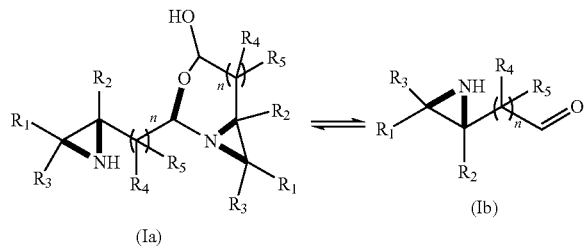

(Ia)       (Ib)

wherein n, $R_1$, $R_2$, $R_3$, $R_4$ and $R_5$ are as defined above, under conditions suitable to effect reaction between the aziridine ring nitrogen and the electrophile.

In still another embodiment, the invention provides a process for preparing a bioactive molecule comprising reacting a precursor molecule containing a nucleophilic group with an aziridine aldehyde of formula (Ia) and/or (Ib):

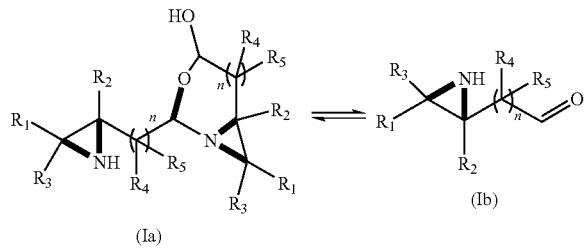

(Ia)       (Ib)

wherein n, $R_1$, $R_2$, $R_3$, $R_4$ and $R_5$ are as defined above, under conditions suitable to effect reaction between the nucleophilic group and the aziridine ring of formula (Ia) and/or (Ib) to yield the bioactive molecule.

Using an unprotected aziridine as a secondary amine, it was considered possible that a thermodynamic driving force to undergo condensation could be offset by a high barrier imposed on this process by the aziridine ring strain. Strained iminium ions derived from aziridines can be formed under forcing conditions (Daly, J. *J. Org. Chem.* 1970, 35, 1861). The effect of ring strain on reversible formation of iminium ions from secondary amines and aldehydes is illustrated in Scheme 7. As a result, a previously unknown class of molecules, aziridine aldehydes, has been identified. These valuable intermediates may be applied to generating complex pentacyclic frameworks in one simple operation, which will be outlined below.

Scheme 7

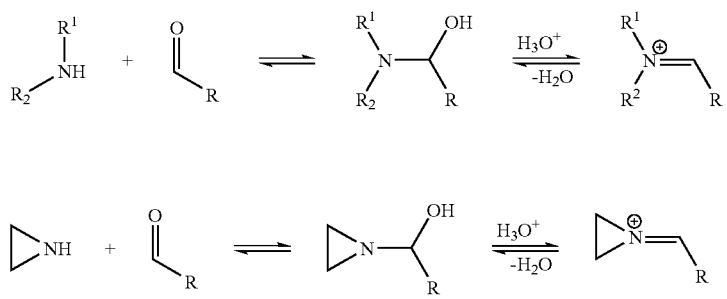

The aziridine aldehydes were prepared from aziridine esters (Davis, F. A in *Aziridines and Epoxides in Organic Synthesis*; Yudin, A. K., Ed.; John Wiley & Sons, New York, 2006; L. Yu, A. Kokai, A. K. Yudin, *J. Org. Chem.* 2007, 72, 1737), which were in turn made from readily available epoxy esters by treatment with sodium azide followed by triphenylphosphine (Legters, J.; Thijs, L.; Zwanenburg, B. *Tetrahedron Lett.* 1989, 30, 4881; Serafin, S. V.; Zhang, K.; Aurelio, L.; Hughes, A. B.; Morton, T. H. *Org. Lett.* 2004, 6, 1561). Aziridine esters may also be prepared from serine esters via an intramolecular Mitsunobu reaction (Chervin, I. I.; Fomichev, A. A.; Moskalenko, A. S.; Zaichenko, N. L.; Aliev, A. E.; Prosyanik, A. V.; Voznesenskii, V. N.; Kostyanovskii, R. G. Inst. Khim. Fiz., Moscow, USSR. Izvestiya Akademii Nauk SSSR, Seriya Khimicheskaya 1988, 5, 1110).

Figure 2A:
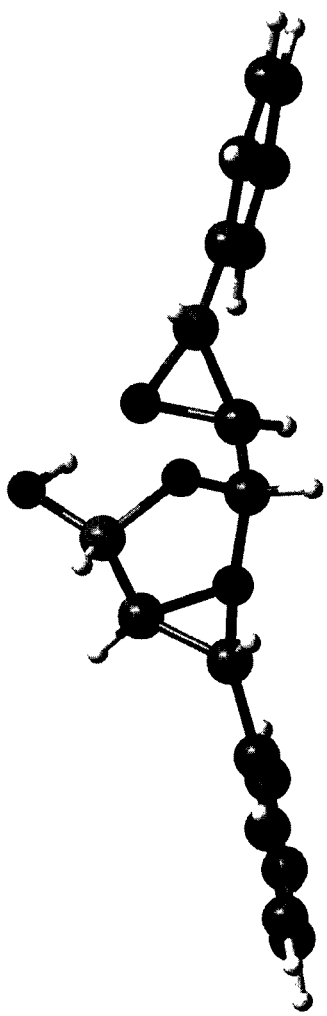
Figure 2B:
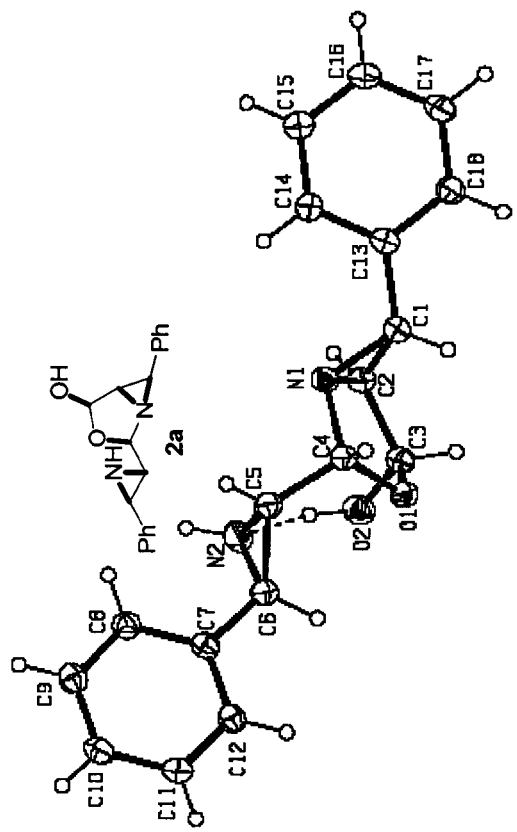

The reduction of the aziridine ester 1a with DIBAL furnished a bench-stable white solid in 83% yield (Table 1, entry 1). Gratifyingly, its X-ray crystallographic analysis (FIGS. 2a and 2b) revealed that the aziridine aldehyde was formed and had undergone a diastereoselective homodimerization, rather than giving products of premature condensation via iminium ion formation, confirming the hypothesis that the aziridine and aldehyde functionalities can co-exist.

Scheme 8 generally illustrates the synthesis of aziridine aldehyde dimers from aziridine esters.

Scheme 8

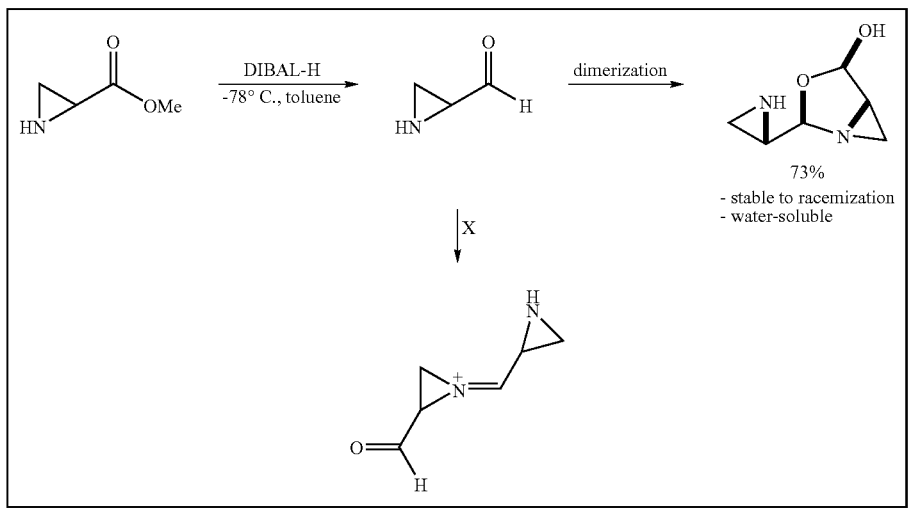

Several aziridine aldehydes with different substitution patterns were prepared using this method (Table 1). The products were off-white solids that were purified by recrystallization, with the exception of 2e and the parent aziridine aldehyde 2d, which was a water-soluble, colourless liquid. In order to establish the synthetic utility of aziridine aldehydes, the nature of equilibrium between their dimer and monomer states was evaluated (Scheme 9).

TABLE 1

Aziridine aldehyde dimers obtained through DIBAL reduction of aziridine esters.[a]

| entry | aziridine ester | product | yield[b] |
|---|---|---|---|
| 1 | 1a | 2a | 83% |
| 2 | 1b | 2b | 81% |
| 3 | 1c | 2c | 92% |
| 4 | 1d | 2d | 76% |

TABLE 1-continued

Aziridine aldehyde dimers obtained through DIBAL reduction of aziridine esters.[a]

| entry | aziridine ester | product | yield[b] |
|---|---|---|---|
| 5 | 1e (OTBDMS, NH, CO₂Et) | 2e | 94% |

[a]Reactions were carried out using 1 equiv. of ester and 2 equiv. of DIBAL in toluene at -78° C.
[b]Isolated yields.

Scheme 9.
Equilibrium between homodimer 2a and free aziridine aldehyde with subsequent reductive transformations.

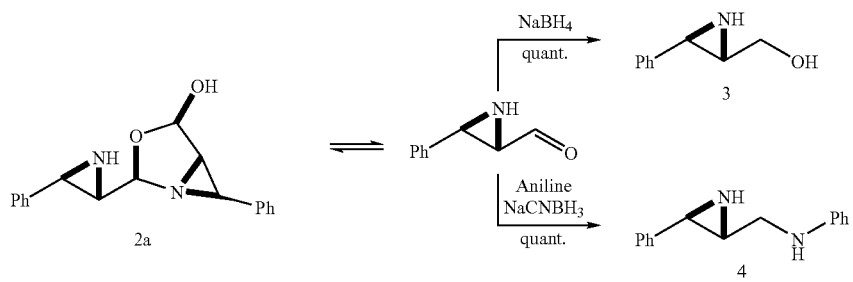

The monomeric aldehydes were obtained in MeOH/THF and were cleanly reduced with sodium borohydride to give the aziridine alcohols (e.g. 3). Furthermore, reductive amination of 2a with aniline furnished the diamine 4 in quantitative yield. This result demonstrates that the aziridine functional group is orthogonal to the aldehyde in *the course of the reaction*, allowing selective reactivity with an external secondary amine at the aldehyde carbon.

Which pattern of reactivity can be expected of a kinetically amphoteric molecule? Under the conditions where the orthogonal nodes of reactivity (indicated as Nu and E in Scheme 10) behave independently, attack by an external nucleophile (Nu¹ in Scheme 10-a) should lead to a nascent electrophile that should undergo cyclization. The overall process can also be initiated at the other end of the molecule if the external party is of electrophilic character. The ensuing relay will then be driven by a nascent nucleophile. Importantly, upon reaction with an amphoteric molecule, all subsequent nucleophile/electrophile interactions are no longer orthogonal and should proceed with favourable kinetics. Each of these processes can incorporate non-trivial steps, such as skeletal rearrangements. It is therefore possible to imagine that many complex reactions can be designed using this simple principle.

Scheme 10

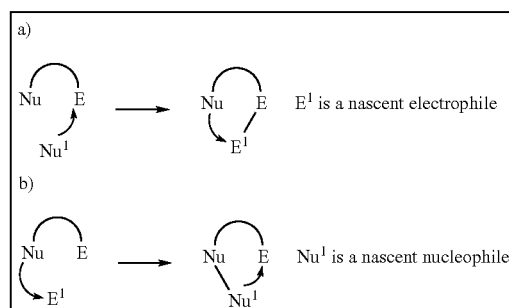

Motivated by ongoing interest in efficient construction of complex alkaloid scaffolds (Hesse, M. *Alkaloids: Nature's Curse or Blessing?*; John Wiley & Sons: New York, 2002) and encouraged by the chemoselective iminium ion chemistry in the presence of an unprotected NH aziridine moiety (Scheme 9), the orthogonal relationship between the aziridine and aldehyde groups was further investigated by reacting 2a with N-benzyltryptamine (6), a bifunctional nucleophile capable of iminium ion formation (for application of tryptamine derivatives in the Pictet-Spengler reaction, see: Cox, E. D.; Cook, J. M. *Chem. Rev.* 1995, 95, 1797). When aziridine aldehyde 2a was reacted with 6 in toluene at 80° C. for 16 hours, a 2:1 diastereomeric mixture of pentacycles 5a and 5b was isolated in 74% yield as an off-yellow solid (Scheme 11). The diastereomeric structures were assigned using 2D-NMR and verified using X-ray analysis of 5b.

Scheme 11.
Preparation of pentacycles from aziridine aldehydes and N-benzyl tryptamine.

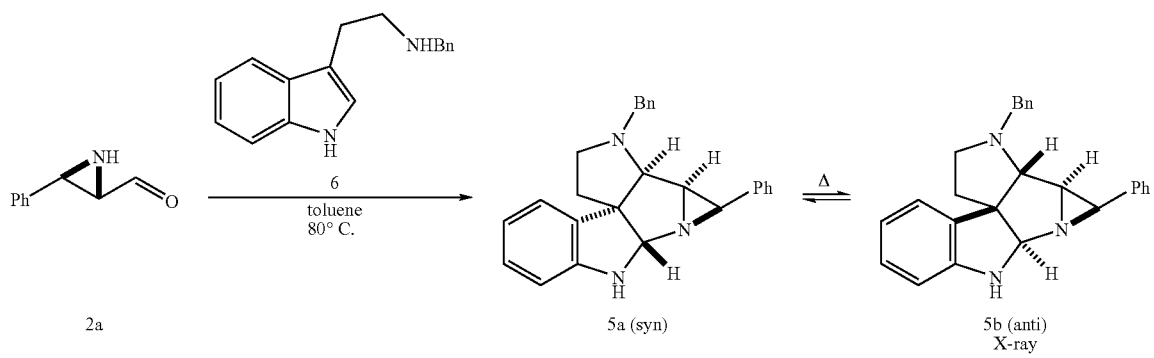

The aziridine ring of 5b can be readily opened by benzenethiol in the presence of 5 mol % Zn(OTf)$_2$ resulting in a stable aminal product (Scheme 12). The reaction is completed within one hour with >99% regioselectivity.

Scheme 12.
Regioselective ring opening of 5b with benzenethiol.

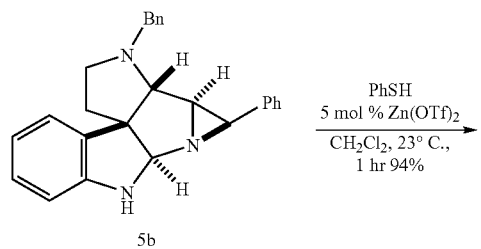

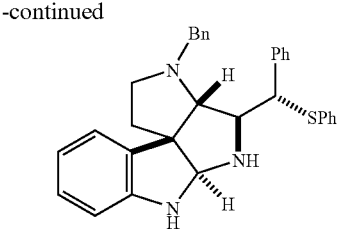

The diastereoselectivity of polycyclization was explored using a variety of protic and aprotic solvents. When 5a was heated in toluene with a catalytic (5 mol %) amount of water, a 10:1 mixture of 5b and 5a was obtained. Since the thermodynamic product was accessible under thermal conditions, a diastereoselective route to 5a was pursued. Polyfluorinated alcohols proved to be the optimal media. Scheme 13 illustrates the one-step synthesis of pentacycles from amphoteric aziridine aldehydes, and the mechanism for same.

Scheme 13

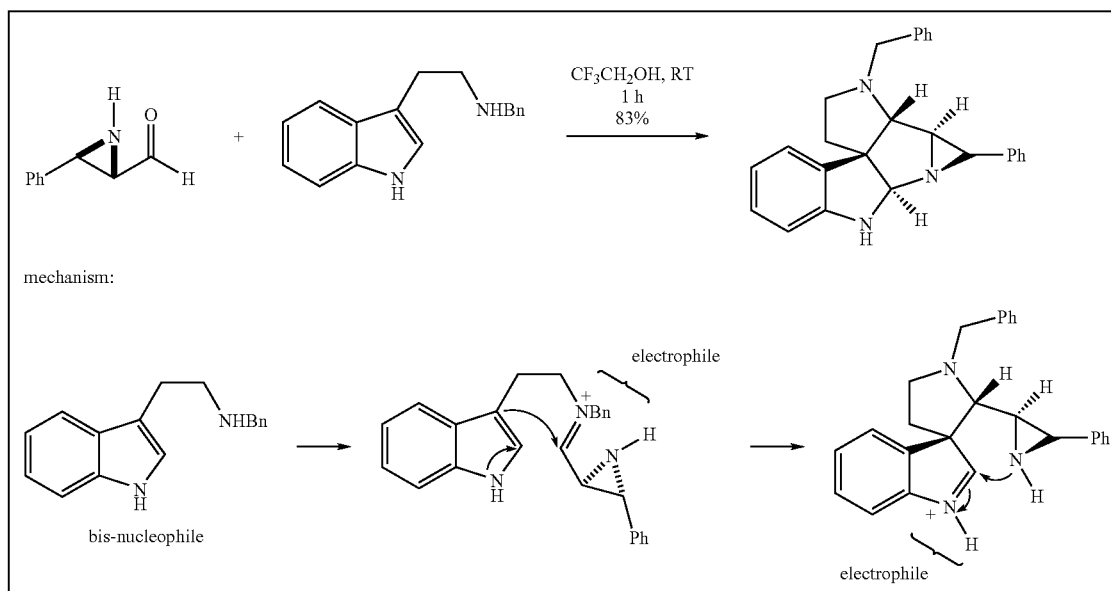

In the course of the reaction, iminium ion formation is followed by intramolecular attack of the indole to generate a spirocyclic intermediate. Subsequently, the aziridine nitrogen adds to the iminium ion to generate the final product. As a result, the bis-nucleophilic N-benzyltryptamine acts as a precursor to a bis-electrophile through the action of an amphoteric aziridine aldehyde.

When 2a and 6 were reacted in trifluoroethanol (TFE) at 0° C. for three hours, selective formation of the pentacyclic adduct 5a took place in 97% yield. Gratifyingly, when the reaction temperature was decreased to −20° C., a >20:1 ratio of 5a/5b was obtained. The heteroaromatic aziridine aldehyde 2c exhibited poor reactivity as it was only moderately soluble in trifluoroethanol at room temperature. Importantly, the parent aziridine aldehyde 2d, which along with 2e is the most synthetically versatile compound of this series, gave high yield of the pentacyclic product.

It should be noted that the amino aldehydes of the present invention possess several properties which contribute to their synthetic utility. Among these are the following:

a. The novel aziridine aldehydes contain both a secondary amine functionality and an aldehyde functionality and are stable with regard to inter- and intramolecular condensation and iminium ion formation. These molecules are stable in non-protonated form as opposed to certain rare cases of amine containing aldehydes that are known (e.g. glucosamine).

b. There is no epimerization at the alpha carbon.

c. Regarding the formation of pentacycles, the novel aziridine aldehydes demonstrate a unique reactivity. Based on what is known in the art, for an aldehyde with OH or SH alpha substituent, one would reasonably expect a different product (as shown below in Scheme 14):

TABLE 2

Pentacycles derived from aziridine aldehydes and N-benzyl tryptamine.[a]

| entry | dimer | T (° C.) | time | pentacycle[b] | yield[c] | syn/anti[d] |
|---|---|---|---|---|---|---|
| 1 | 2a | 0 | 3 h | | 97% 94% | 8:1 20:1[e] |
| 2 | 2b | 40[f] | 8 h | | 81% | 2:1 |
| 3 | 2d | 0 | 3 h | | 74% | 1.5:1 |
| 4 | 2e | 0 | 3 h | | 94% | 3:1 |

[a]Unless stated otherwise, the reactions were carried out using 1 mmol of the dimer (2 mmol of aldehyde) and 2 mmol of N-benzyl tryptamine in 2 ml of TFE at 0° C. for 3 hours.
[b]Major diastereoisomer shown.
[c]Isolated yield.
[d]Based on crude $^1$H NMR.
[e]Reaction was run at -20° C.
[f]Elevated temperature was required for reaction to occur.

Scheme 14:

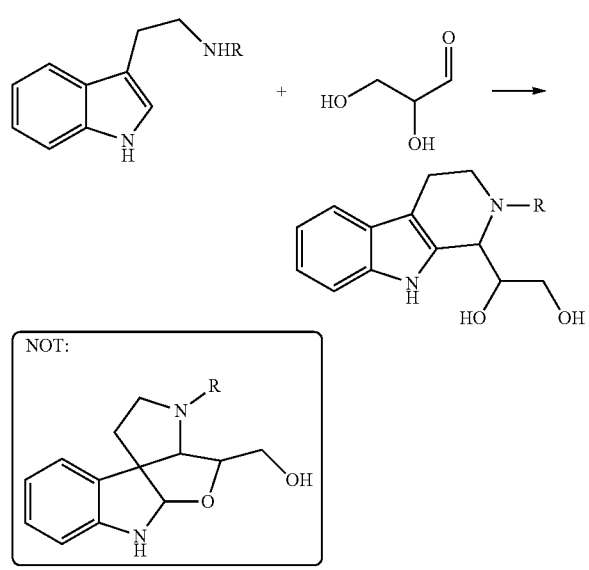

d. The novel amino aldehydes of the present invention allow for selective reductive amination employing the novel aziridine aldehydes as the aldehyde partner and external amines as the amine partner without having to protect either amine functionality.
e. It is envisioned that utilizing the novel aziridine aldehydes in synthetic processes will decrease the number of steps leading to various nitrogen-containing target molecules in a synthetic sequence. Because aziridine ring can be regarded as a stepping stone towards a wide variety of amines via well documented ring-opening chemistry (*Aziridines and Epoxides in Organic Synthesis* (Ed.: A. K. Yudin), Wiley, N.Y., 2006), these unprotected building blocks provide a solution to broad challenges faced by protected amino aldehydes in complex amine transformations (J. Jurczak, A. Golebiowski, *Chem. Rev.* 1989, 89, 149; M. T. Reetz, *Angew. Chem.* 1991, 103, 1559; *Angew. Chem. Int. Ed. Engl.* 1991, 30, 1531; F. J. Sardina, H. Rapoport, *Chem. Rev.* 1996, 96, 1825).
f. The formation of an unsymmetrical dimer by the aziridine aldehydes of the present invention is unique, and would not be expected based on what is known in the art (Scheme 15). It is thought that the formation of this dimer contributes to the stability of the compounds of the present invention. The aziridine aldehyde compound previously prepared by Rheinhoudt (compound 9 in Rheinhoudt et al., supra) was isolated in monomeric form, as evidenced by an aldehyde peak in the NMR spectrum of compound 9. As previously mentioned, this compound was found to be unstable and could not be isolated in pure form.

Scheme 15:

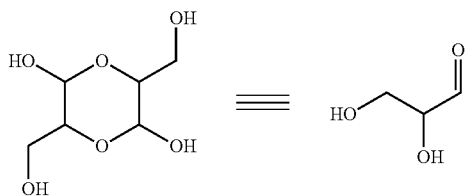

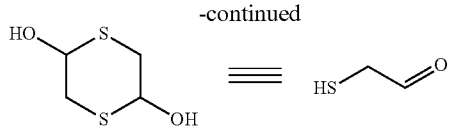

The novel aziridine aldehydes of the present invention are expected to find utility in a broad range of synthetic applications. If one does retrosynthetic analysis of a given molecule and arrives at an amino aldehyde synthon, the synthetic equivalent will necessarily be a protected amino aldehyde. The novel aziridine aldehydes of the present invention provide a strategic alternative which is preferred due to superior atom economy (Trost *Science* 1991, 254, 1471) as well as step economy (Wender *Tetrahedron* 2006, 62, 7505).

The novel aziridine aldehydes can also be used for the incorporation of aziridines into both simple and complex molecules. There is no more straightforward way to incorporate this ring into a molecule having functional groups with potential chemoselectivity issues because the so-called aziridination reactions require olefin or imine starting materials and there is no one-step olefin or imine aziridination that gives NH aziridine as a product.

Figure 1:
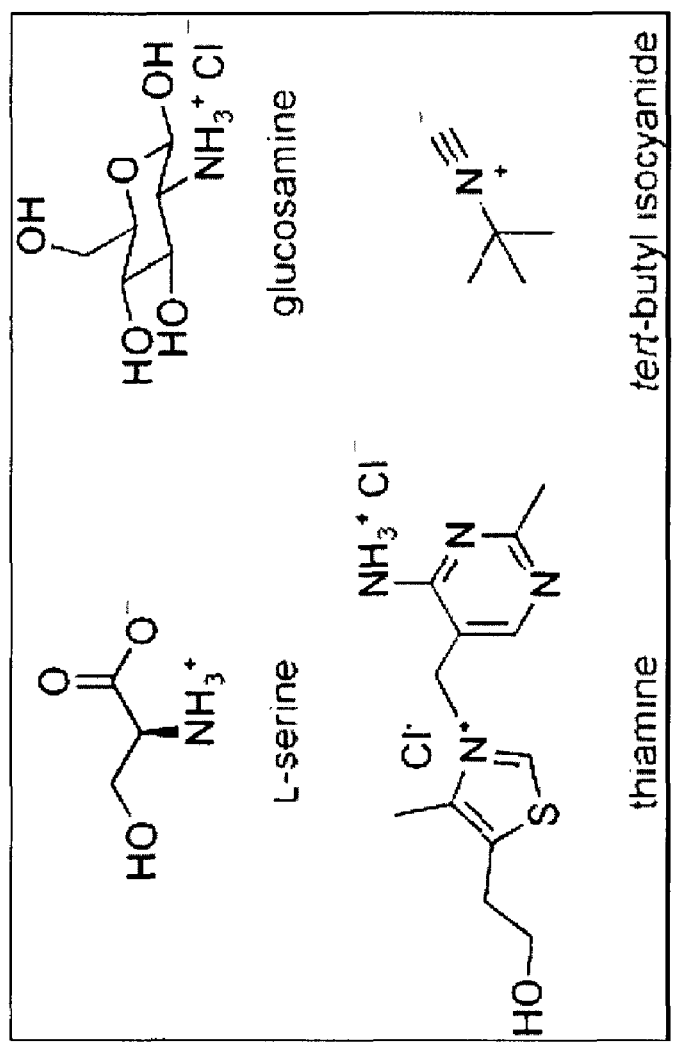
FIG. 1 illustrates selected examples of amphoteric molecules.

In effort to discover new reactivity, organic chemists strive to separate kinetic and thermodynamic factors. It has been demonstrated herein that imposing kinetic barriers on functional groups that are known to engage in irreversible and thermodynamically favourable processes can lead to stable molecules in which reactive functional groups remain orthogonal to each other. This concept was demonstrated on a specific example of an aziridine/aldehyde system that does not display iminium ion chemistry on the basis of excess strain in the intermediate iminium ion. Other combinations of functional groups that satisfy the criteria of amphoterism on kinetic grounds are likely to be identified. In fact, many of them already exist (FIG. 1), but their utility in the context of chemoselective synthetic operations has been under-appreciated. Upon identification of the amphoteric pair of functional groups, one can also anticipate creating a myriad of homologous molecules in which additional functional groups separate the opposing nodes of reactivity. The amphoteric nature of these compounds can lead to high bond-forming efficiency indexes (L. F. Tietze, *Chem. Rev.* 1996, 96, 115) and rapid generation of complex molecular skeletons. Thereby, the amphoteric molecules will provide a seamless bridge to atom and step economy and may contribute to the development of useful waste-free technologies.

Vinblastine Analogs

Vinblastine is used in the treatment of various cancers such as Hodgkin's disease, lymphoblastic leukemia, breast, lung, and testicular cancer. However, vinblastine also affects healthy bone marrow cells, leukocytes and granulocytes. This can bring about a number of side effects including decreased white blood cells, hair loss, kidney disease, nausea, and vomiting. The commercial production of vinblastine is expensive, since only natural sources with low vinblastine concentration are available. Although catharanthine can be produced in cell cultures of *Catharanthus roseus*, the biosynthesis of vindoline in these cell systems is interrupted at the stage of tabersonine. Therefore, vinblastine cannot be obtained biosynthetically from such in vitro systems.

Regarding the utility of the pentacycles of formula (V) disclosed herein and prepared using the aziridine aldehydes of the present invention, it is envisioned that conjugation of these molecules with nucleophiles such as thiols with linking to catharanthine (commercially available) using well known chemistry (Polonovsky) will yield new vinblastine analogs which will have utility as anticancer drugs.

Figure 6:
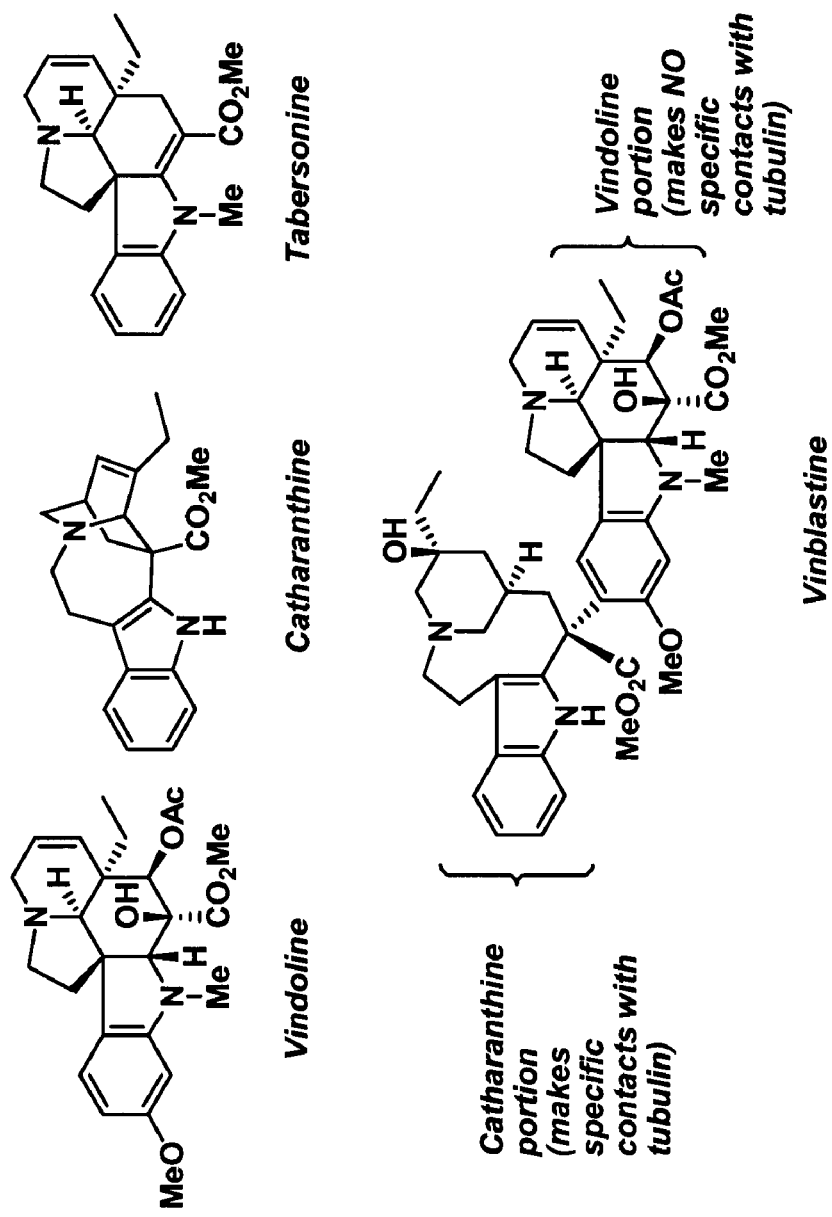
FIG. 6 illustrates selected vinca alkaloids.
Figure 7:
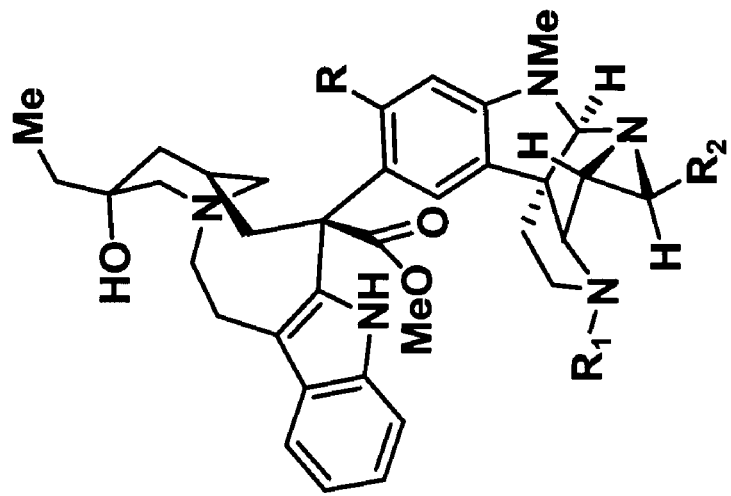
FIG. 7 illustrates common features between vinblastine and pentacycle-derived hybrids.
Figure 7:
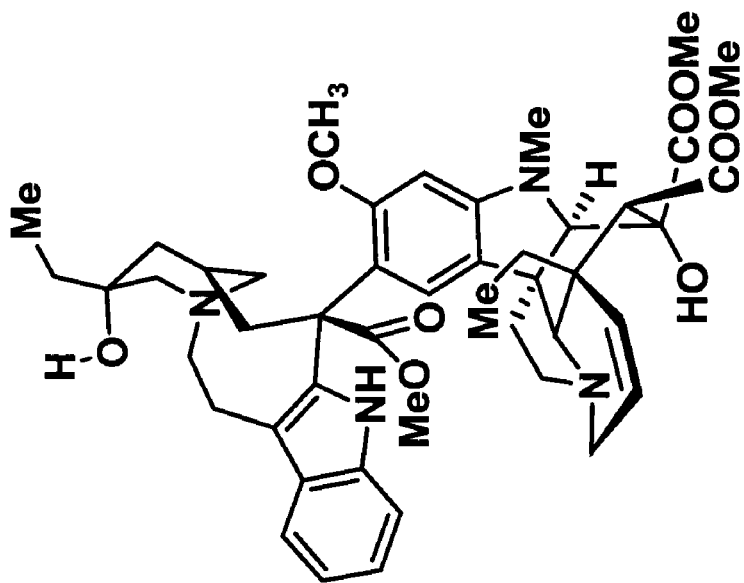

Recently, Knossow and co-workers (Knossow et al *Nature* 2005, 435, 519-22) solved a crystal structure of the vinblastine-tubulin complex at 4.1 Å resolution. According to this study, vinblastine introduces a wedge at the interface of two tubulin molecules which interferes with tubulin assembly. Ultimately, this leads to tubulin self-association into spiral aggregates which arrests microtubule growth. A molecular level analysis of this structure reveals an interesting feature: the southern (vindoline) portion of vinblastine makes no hydrogen bond contacts with the nearby amino acid residues. The only tubulin residues that are found within 6 Å sphere around vinblastine are P220 and N329. They interact with the northern (catharanthine) portion of vinblastine. This paucity of contacts is the underlying reason for the vindoline portion contributing only 25% to overall binding energy between vinblastine and tubulin. Catharanthine accounts for the remaining 75%. Our recent molecular modeling studies suggest significant shape similarity between vindoline and a series of molecules that are now readily available in one step using the amino aldehyde chemistry. Conjugation of the pentacycles with commercially available catharanthine using Polonovsky reaction can be used to make vinblastine analogs. The Polonovsky protocol is a well established process that has been used in order to couple vindoline and catharanthine fragments en route to vinblastine. The rationale for using this chemistry in order to arrive at a superior antitumor molecule is indicated in FIGS. 6 and 7 and in Schemes 16 and 17 below.

Scheme 16: The Polonovsky protocol for pentacycle-derived hybrid synthesis

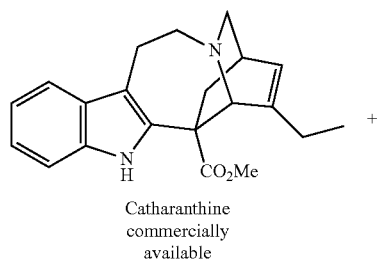

Catharanthine commercially available

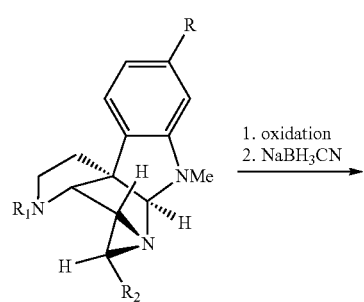

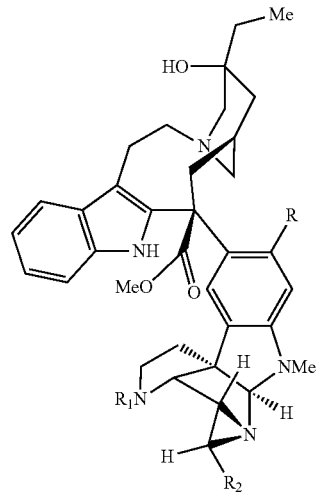

Scheme 17: Use of thiols in order to incorporate substituents that are expected to make specific contacts in the vindoline area (vinblastine does not make contacts in the vindoline area)

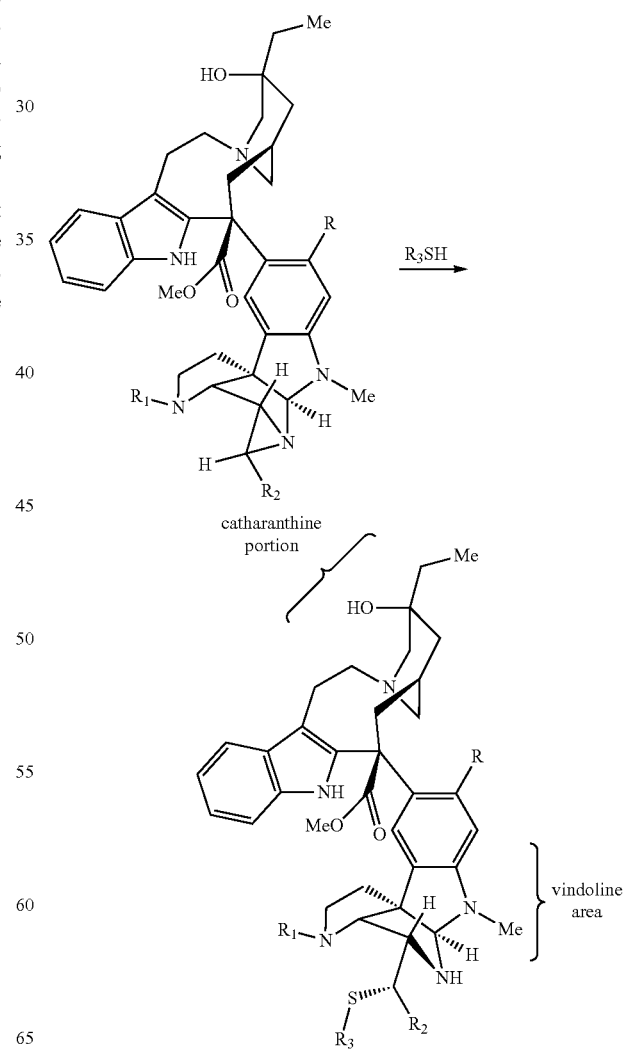

Siderophore Chemistry

Amino aldehydes can be used in order to form derivative of siderophores such as pyochelin. Pyochelin is a siderophore and virulence factor common to *Burkholderia cepacia* and several *Pseudomonas* strains. The broad range of utilization makes this siderophore an attractive candidate for the design of new anti-microbial drugs that would use the Pch uptake pathway.

Cobessi et al. have described the crystal structure of the pyochelin outer membrane receptor FptA bound to the iron-pyochelin isolated from *Pseudomonas aeruginosa* (Cobessi, D. et al. *J. Mol. Biol.* (2005) 352: 893-904). A hydrophobic pocket has been identified within this receptor, and it is believed that the presence of additional hydrophobic substituents on the thiazolin portion of this molecule will lead to better binding activity with this receptor. Pyochelin itself is derived from cysteine. With the methodology set out below, one can make completely unnatural derivatives which cannot be made even by induced biosynthesis.

The route disclosed herein is the fastest to date and highlights an important attribute of amino aldehydes, namely that selective chemistry can be performed on the aldehyde portion of the molecule without prematurely affecting the aziridine portion. Thus, the aldehyde has been reacted with the cysteine ethyl ester which was followed by a ring opening/ring closure sequence using an aromatic thioacid. Thereby, novel derivatives containing various substituents capable of interacting with the hydrophobic pocket of its outer membrane receptor (the target of pyochelin), have been constructed in a record few steps (Scheme 18).

Scheme 18

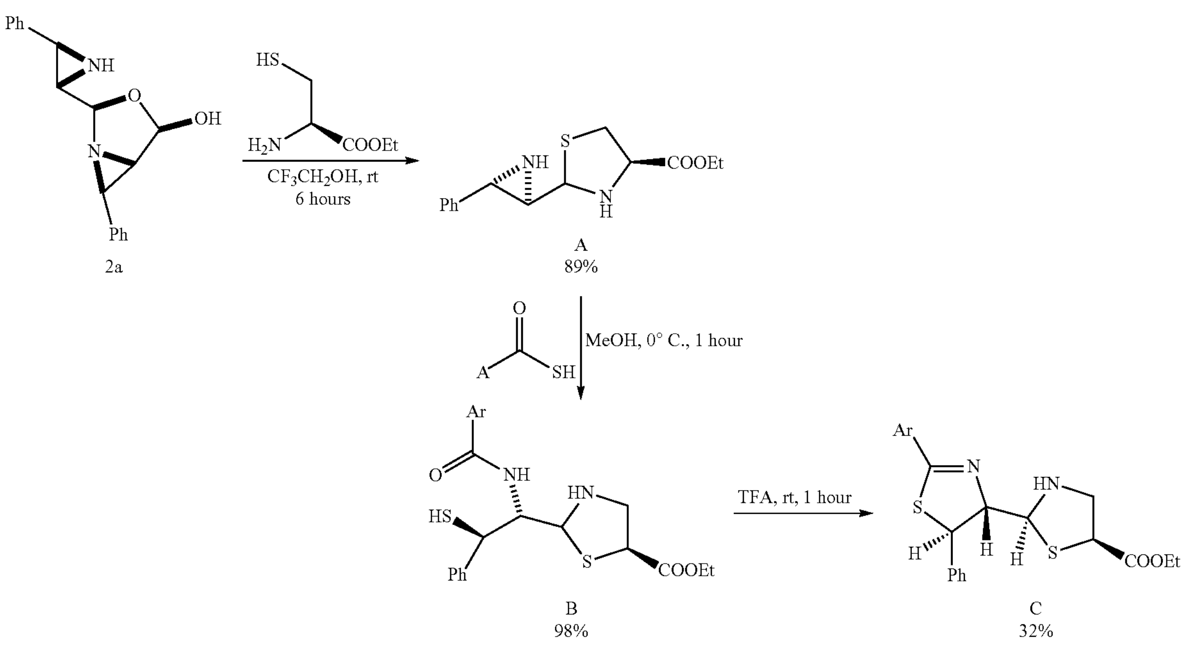

Wittig Chemistry

Amino aldehydes can be easily transformed into a wide range of alkenyl aziridines using Wittig and Horner-Wadsworth-Emmons chemistry (Scheme 19). This transformation opens a door at a class of molecules that is difficult to synthesize by alternate means.

Scheme 19

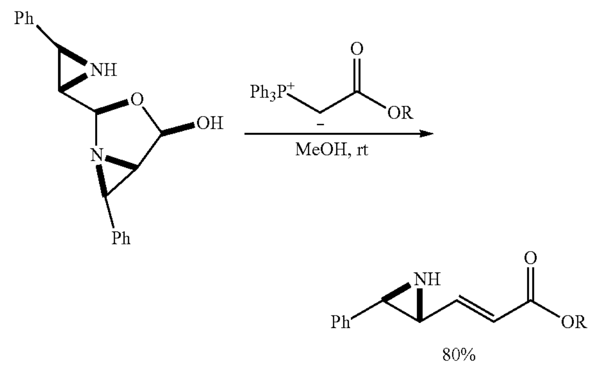

Preparation of Bioactive Molecules

The aziridine aldehydes of the present invention may also be used to prepare bioactive compounds from various precursors which may or may not be bioactive in and of themselves, but possess functionalities capable of reacting with aziridine aldehyde to form novel bioactive conjugates. Such a bioactive compound may also be a prodrug that is conjugated with aziridine aldehyde upon reductive amination. Once the aziridine ring is opened, the drug is generated. Unopened aziridine can also be preserved in a product if desired, and such compounds may be beneficial for certain applications (e.g. mitomycin C is an anticancer drug with NH aziridine—see for example Sherman, D. H. et al. *JACS,* 2001, 123, 6712).

The novel aziridine aldehydes of the present invention may also be used in the preparation of irreversible inhibitors. In the context of the present application, an inhibitor refers to a molecule which prevents or impedes another molecule from engaging in a reaction and/or occupying a binding site. For example, a bioactive compound, such as a drug, may be covalently linked to an aziridine aldehyde using reductive amination (as noted above) or other procedures, and the activated conjugate may then be used to assess the binding location of the drug at an active site. Allosteric sites can be identified and/or new competitive inhibitors may be discovered on the basis of structural information.

The aziridine aldehydes of the present invention may be conjugated to other molecules via reductive amination, as described herein. Reductive amination is well-tolerated by bioactive molecules, and is a well-known method for modifying such molecules (McFarland, J. M and Francis, M. B. *Reductive Alkylation of Proteins Using Iridium Catalyzed Transfer Hydrogenation,* 2005, 127, 13490, and Means, G. E. *Reductive Alkylation of Proteins,* 1984, 3(1), 121, the contents of which are herein incorporated by reference in their entireties). Other methods suitable for conjugating aziridine aldehydes to other molecules include reaction with other nucleophiles (for ring opening of aziridine or addition to aldehyde—with carbon-, oxygen, nitrogen nucleophiles), and reaction of the aziridines with other electrophiles at nitrogen. Such electrophiles include alpha, beta unsaturated carbonyls such as acrylic acid methyl ester and aldehyde etc; carboxylic acids; acyl chlorides; allylic halides and allylic acetates; imines and iminium ions.

Nucleophiles which are capable of reacting with the aziridine aldehydes through nucleophilic attack include the following: hydride; deuteride; amines, including azides, ammonia, primary and secondary amines; alcohols; halides; carbanions including metal cyanides, isocyanides, organolithiates, organozincates, Gringard reagents, metal acetylides, enololates such as malonates etc., enol ethers such as metal enolates, silyl enolates etc., enamines such as indoles, aromatics capable of participating in Electrophilic aromatic substitutions, stabilized and unstabilized phosphorous and sulfur ylids, etc.; thiols including benzenethiol etc., and carboxylic acids.

Conjugation with Amino Acids and Peptides

Amino aldehydes can be used in order to reductively aminate the N-terminal position of an amino acid or a peptide. No racemization of the amino acid stereocenter was observed during this process. Thereby, novel enzyme inhibitors such as cysteine protease inhibitors can be assembled in one simple operation from a wide range of peptides.

Scheme 20

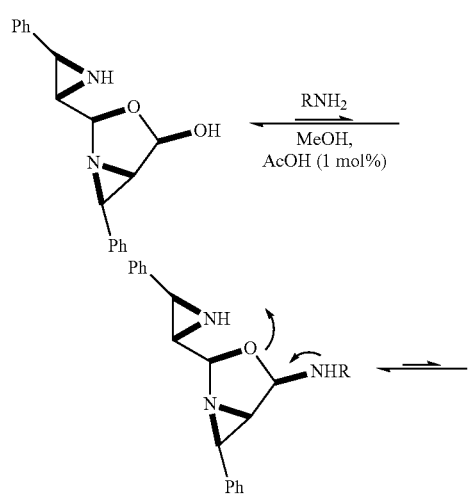

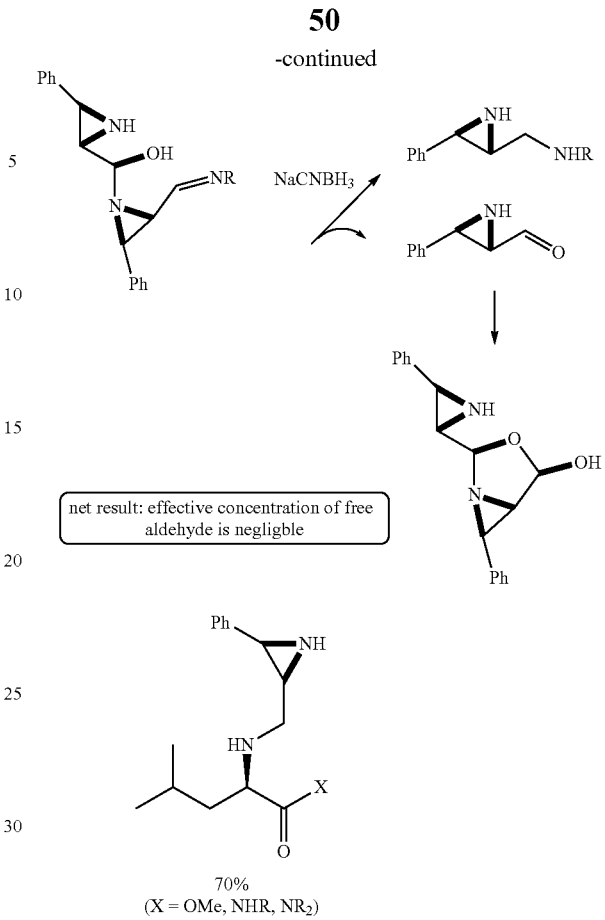

Many cysteine protease inhibitors are known, some of which possess aziridine functionalities (Schirmeister et al. *Current Topics in Medicinal Chemistry* 2006, 6, 331), and thus appropriately functionalized aziridine compounds may have a good chance of being cysteine protease inhibitors. For example, the compound 2e can undergo reductive amination followed by oxidation of the alcohol functionality by known procedures to generate aziridine acid, a well-known motif present in cysteine protease inhibitors (see Schirmeister et al., supra).

Unprotected amino aldehydes have potential in constructing peptidomimetic conjugates. A general strategy that addresses three critical issues in methodology directed towards peptidomimetic protease inhibitors has been developed: (1) the reaction sequence can be used in order to selectively attach an unprotected aziridine electrophile to an amino acid-containing molecule; (2) it delivers a peptidomimetic connection without epimerization on either side of the reduced amide bond; and (3) it allows for a late-stage peptidomimetic ligation.

The kinetic amphoterism has been coined in order to describe the co-existence of an unprotected aziridine and aldehyde groups in the aziridine aldehydes of the present invention (Hili, R.; Yudin, A. K. *Chem. Eur. J.* 2007, 13, 6538). Attachment of an unprotected aziridine unit to an amino acid residue via a non-peptide bond not only gains access to an electrophilic peptidomimetic conjugate, but also facilitates synthesis of both natural and unnatural amino acid-based peptidomimetics via aziridine ring-opening chemistry. For recent applications of aziridine carboxylic acids, see: (a) Vicik, R.; Busemann, M.; Baumann, K.; Schrimeister, T.

Curr. Top. Med. Chem. 2006, 6, 331; (b) Galonić, D. P.; Ide, N. D.; van der Donk, W. A.; Gin, D. Y. *J. Am. Chem. Soc.* 2005, 127, 7359.

Standard reductive amination conditions (NaBH₃CN, MeOH, 1% HOAc) on aziridine aldehyde dimers and amino acid derivatives delivered poor conversions and yields. Extensive experimentation revealed that ZnCl₂/NaBH₃CN combination delivers optimal selectivity. Most importantly, the reductive amination was not accompanied by either overalkylation or epimerization on either side of the peptidomimetic connection. A mechanistic investigation uncovered the salient features of this process (Scheme 21).

Without being bound by theory, the data in hand suggest that the monomeric amino aldehyde-derived imine formation is not taking place during the reaction. Instead, the adduct iii, formed upon condensation between the amino aldehyde dimer i and amine ii, participates in an unfavorable equilibrium with its "half-opened" form iv which is rapidly reduced by the hydride transfer agent. The short lifetime of iv ensures that the rates of tautomerization and, therefore, epimerization, are negligible. Using this protocol, a variety of unprotected amino aldehydes can be cleanly conjugated with α-amino acid derivatives (Table 3).

Scheme 21

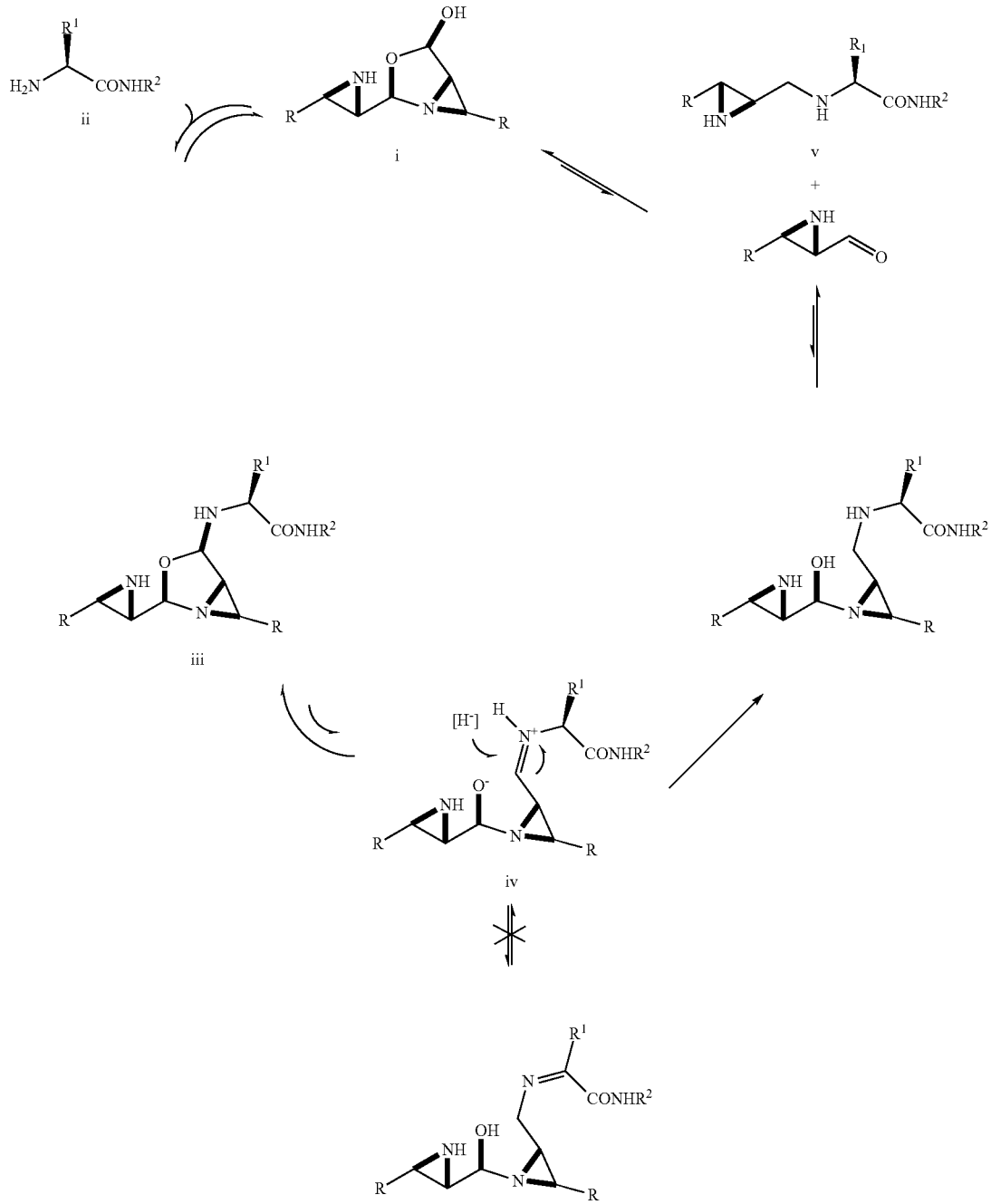

TABLE 3

The scope of peptidomimetic conjugation chemistry.[a]

| entry | aziridine aldehyde[b] | amino acid derivative | yield[c] |
|---|---|---|---|
| 1 | i-a | ii-a | 85% |
| 2 | i-a | ii-b | 75% |
| 3 | i-a | ii-c | 86% |
| 4 | i-a | ii-d | 81% |
| 5 | i-b | ii-e | 92% |
| 6 | i-b | ii-f | 84% |

TABLE 3-continued

The scope of peptidomimetic conjugation chemistry.[a]

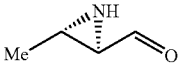

| entry | aziridine aldehyde[b] | amino acid derivative | yield[c] |
|---|---|---|---|
| 7 | i-c | ii-d | 60% |
| 8 | i-d | ii-d | 51% |

[a]Unless stated otherwise, the reactions were carried out using 0.5 eq. of the dimer (1 eq. aldehyde), 1.2 eq. amine, 1.5 eq. NaBH$_3$CN, and 1 eq. ZnCl$_2$ in THF and MeOH (1/1) at room temperature;
[b]The corresponding monomer;
[c]Isolated yield.

The absence of epimerization on the aldehyde side of the aminomethylene linkage is secured through energetically uphill enolization of the strained aziridine aldehyde. Another key feature of this process is that the equilibrium concentration of the free aldehyde is unobservably low, resulting in no over-alkylation (overalkylation during reductive amination is a recognized problem: Abdel-Magid, A. F.; Carson, K. G.; Harris, B. D.; Maryanoff, C. A.; Shah, R. D. *J. Org. Chem.* 1996, 61, 3849). A presently unexplained fidelity with regard to homochiral dimer reformation during the reaction must be responsible for the low concentration of the free aldehyde. The crossover between two different amino aldehyde dimers has been detected by ESI MS only in trifluoroethanol (pKa 12.4), definitively suggesting appreciable concentration of the free aldehyde species in that solvent. Importantly, the reductive amination is not occurring in trifluoroethanol. Instead, the reaction leads to preferential aldehyde reduction, providing further evidence for the dimer-driven mechanism depicted in Scheme 21.

The utility of amino acid conjugates is demonstrated by a thioacid-triggered process (Scheme 22). This sequence offers a possibility for a *peptidomimetic ligation* of two fragments such that a reduced amide bond isostere is specifically introduced next to a cysteine residue with complete stereocontrol of the nearby stereocenters (for native chemical ligation, see: Johnson, E. C. B.; Kent, S. B. H. *J. Am. Chem. Soc.* 2006, 128, 6640).

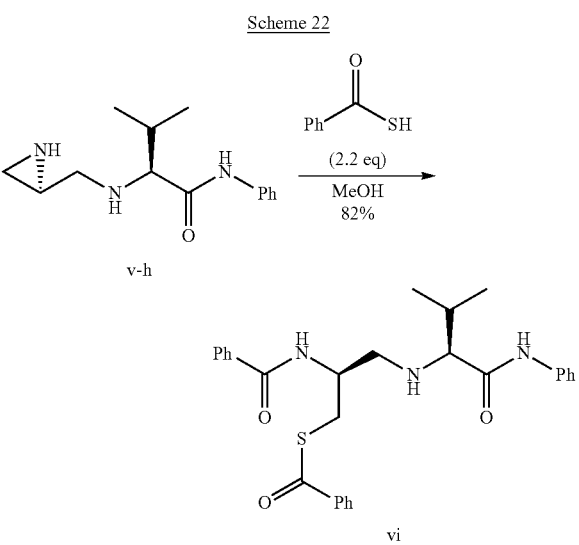

Scheme 22

Thus, a protecting group-free strategy for replacing amide bonds with versatile aziridine-containing templates for the synthesis of peptidomimetics has been developed. To this end, a peptide conjugated with aziridine aldehyde via reductive amination can be subjected to ring opening with thio amino acid using the procedure noted in Scheme 22 in order to produce peptidomimetics. Thio amino acids may be prepared by procedures outlined Goldstein et al. (Goldstein, Alex S.; Gelb, Michael H. An alternate preparation of thioester resin linkers for solid-phase synthesis of peptide C-terminal thioacids. *Tetrahedron Letters* (2000), 41(16), 2797-2800) and references cited therein.

Aziridine-conjugated peptides may be prepared using the same procedures as those used to prepare aziridine-conjugated amino acids. As noted above, any peptide may be used, but for optimal selectivity there should only be one free primary or secondary amino group. It will be understood by a person of skill in the art that free amino groups of side chains of amino acid such as lysine should be protected using protecting groups that are compatible with reductive amination condtions, such as Cbz, and Boc. Peptides of interest can be purchased from known suppliers or prepared by standard synthetic procedures. Amino acid and peptides may be modified or purchased with suitable protecting groups known to those of skill in the art, and such protecting groups may be removed according to standard chemical procedures known to those of skill in the art.

A high degree of stereocontrol achieved during reductive amination hinges upon unusual preferences of the amphoteric amino aldehydes. The advantages of this process are set forth in Scheme 23:

Scheme 23

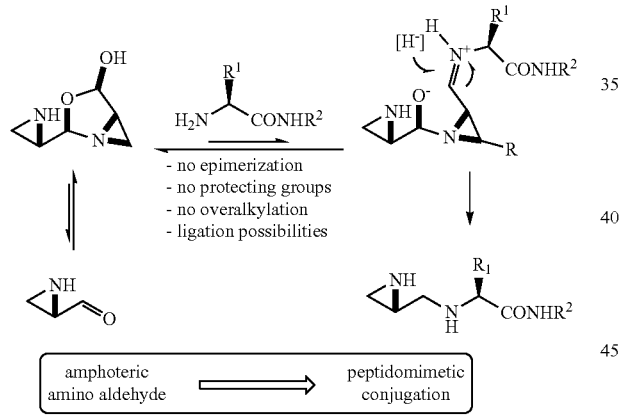

The resulting conjugates contain requisite elements for irreversible protease inhibition as well as the reduced amide bonds at defined positions. One can anticipate straightforward construction of structurally diverse affinity probes using this chemistry (Evans, M. J.; Cravatt, B. F. *Chem. Rev.* 2006, 106, 3279; Fonović, M., Bogyo, M. *Curr. Pharm. Design* 2007, 13, 253). On the other hand, selective ring opening of aziridine rings with nucleophiles can lead to reversible protease inhibitors. The resulting conjugates also offer a possibility for peptidomimetic ligation. Taken together, these findings should allow access to templates for introducing both natural and unnatural amino acid residues in close proximity to the reduced amide bond isosteres, providing SAR-rich synthetic platforms for interrogating protease function and for the synthesis of peptidomimetics.

Nucleoside Conjugates

Amino aldehydes have been conjugated with amino-functionalized nucleoside derivatives using a highly selective reductive amination protocol. This chemistry allows for a straightforward formation of bisubstrate inhibitors useful as precursors to enzyme inhibitors that employ nucleoside cofactors (Scheme 24).

Scheme 24

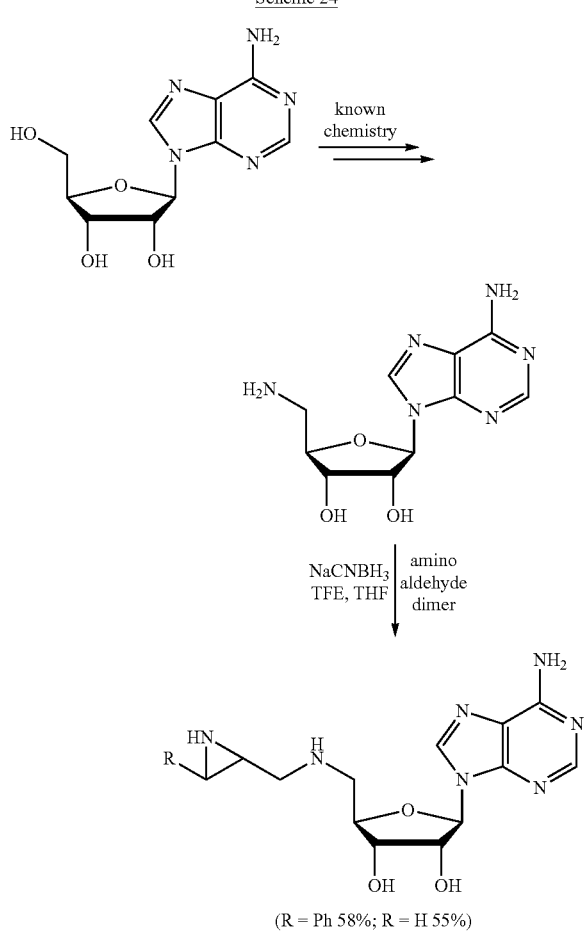

(R = Ph 58%; R = H 55%)

Amino aldehydes have also been conjugated with amino-functionalized nucleoside derivatives in the following manner:

Scheme 25

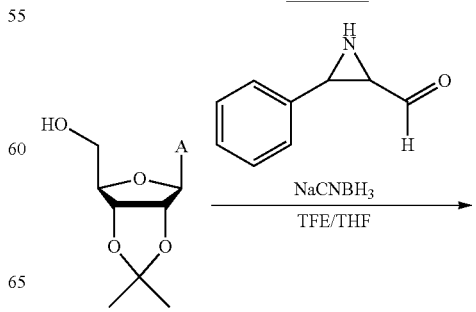

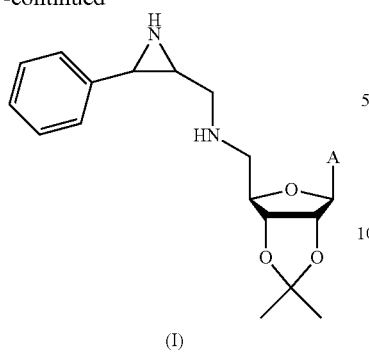

(I)

wherein "A" = adenine.

The acetal protecting group is commonly known to be removed by addition of acid. It is proposed that conditions utilizing light and a catalytic amount of carbontetrabromide may be suitable.

In summary, an efficient synthesis of bench-stable amino aldehydes has been developed and their synthetic utility has been demonstrated. These novel molecules exist as dimers and contain two orthogonal reaction centres, namely an amine/aziridine and an aldehyde, over the span of only three atoms. Their ability to act as linchpins has been evaluated in complex heterocycle synthesis. The amphoteric nature of aziridine aldehydes facilitates invention of new transformations as well as efficient generation of complex molecular skeletons with minimal use of protecting group manipulations.

EXPERIMENTAL

Experimental Procedures

General Information: Anhydrous methylene chloride (dichloromethane; DCM) was obtained using the method described by Grubbs (Pangborn, A. B.; Giardello, M. A.; Grubbs, R. H.; Rosen, R. K.; Timmers, F. J. *Organometallics* 1996, 15, 1518). Anhydrous toluene was purchased and used as received. Tetrahydrofuran (THF) was distilled from sodium benzophenone ketyl under argon. All other solvents were of reagent grade quality. Melting points were obtained on a MelTemp melting-point apparatus and are uncorrected.

Chromatography: Flash column chromatography was carried out using Silicycle 230-400 mesh silica gel and thin-layer chromatography (TLC) was performed on Macherey Nagel pre-coated glass backed TLC plates (SIL G/UV$_{254}$, 0.25 mm) and visualized using a UV lamp (254 nm) or by using either KMnO$_4$ or p-anisaldehyde stains in case of no UV activity.

Nuclear magnetic resonance spectra: $^1$H NMR and $^{13}$C NMR spectra were recorded on Varian Mercury 200, 300, or 400 MHz spectrometers. $^1$H NMR spectra were referenced to TMS (0 ppm) and $^{13}$C NMR spectra were referenced to CDCl$_3$ (77.2 ppm). Peak multiplicities are designated by the following abbreviations: s, singlet; bs, broad singlet; d, doublet; t, triplet; q, quartet; m, multiplet; ds, doublet of singlets; dd, doublet of doublets; ddd, doublet of doublet of doublets; bt, broad triplet; td, triplet of doublets.

Mass Spectroscopy: High resolution mass spectra were obtained on a VG 70-250S (double focusing) mass spectrometer at 70 eV or on an ABI/Sciex Qstar mass spectrometer with ESI source, MS/MS and accurate mass capabilities.

Trans-3-Phenylaziridine-2-carboxylic Acid Ethyl Ester (1a)

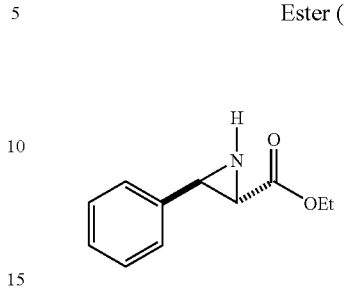

The title compound was synthesized using a literature method (Legters, J.; Thijs, L.; Zwanenburg, B. *Tetrahedron Lett.* 1989, 30, 4881). To a mixture of 3-phenyloxirane-2-carboxylic acid ethyl ester (9.6 ml, 55 mmol) and 183 ml of EtOH in a flame-dried two-necked flask equipped with a water condenser and magnetic stirring rod was added NaN$_3$ (10.73 g, 165 mmol) and ammonium chloride (8.83 g, 165 mmol). The reaction mixture was brought to 65° C. and stirred for 5 hours at which point GC analysis showed that the reaction was complete. The mixture was filtered and concentrated under reduced pressure. The crude $^1$H NMR showed that the product of nucleophilic opening of the epoxide by azide was pure enough to carry over to the next step. In a flame-dried two-neck flask fitted with a water condenser and equipped with a magnetic stirring bar was added the product from above (12.93 g, 55 mmol) dissolved in 183 ml of acetonitrile. The reaction mixture was brought to 40° C., at which point PPh$_3$ (16 g, 61 mmol) was added slow enough to avoid rapid evolution of N$_2$. The reaction was then brought to 83° C. and stirred for 5 hours. The reaction mixture was then cooled and concentrated under reduced pressure. The crude mixture was then dissolved in 5% EtOAc in pentane and filtered. The filtrate was concentrated and subsequently dissolved in pentane and placed in the freezer overnight (−15° C.). Any resulting precipitate that formed was filtered off and the filtrate was concentrated under reduced pressure and subjected to silica gel column chromatography (eluent 20% EtOAc in hexanes) to yield a pale yellow oil in 61% over two steps. $^1$H NMR (200 MHz. CDCl$_3$) (δ: 7.36-7.25 (m, 5H), 4.25 (qd, J=7 Hz, 1.2 Hz, 2H), 3.25 (s, 1H), 2.58 (s, 1H), 1.89 (bs, 1H), 1.31 (t, J=7 Hz, 3H) ppm. $^{13}$C NMR (75 MHz. CDCl$_3$) δ: 171.6, 137.8, 128.3, 127.6, 126.1, 61.6, 40.2, 39.3, 14.0 ppm.

6-Phenyl-2-(3-phenylaziridin-2-yl)-3-oxa-1-azabicyclo[3.1.0]hexan-4-ol (2a)

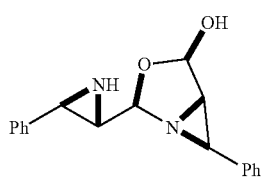

In a flame dried 100 ml Schlenk tube equipped with a magnetic stirring bar was placed 1a (4.78 g, 25 mmol) in 10 ml of toluene. The solution was cooled to −78° C. and a 1.5M solution of DIBAL in toluene (33.3 ml, 50 mmol) was added dropwise along the wall of the vessel. Once the addition was complete, the reaction was allowed to stir at −78° C. for another hour at which point ESI MS showed the disappearance of starting material. MeOH was slowly added along the wall of the vessel at −78° C. The reaction mixture was then allowed to stir for 30 minutes while warming to room temperature. Saturated $Na_2SO_4$ was then added and the solution was allowed to stir for another 15 minutes. The reaction was then filtered and water and ether was added. The organic later was extracted from the partition three times, washed with brine, dried over $Na_2SO_4$ and concentrated under reduced pressure. The resulting white solid may be recrystallized from EtOAc or MeOH to afford the title compound in 83% yield (3.05 g) as a white solid. $^1$H NMR ($CDCl_3$, 200 MHz) δ: 7.83 (d, J=11.6 Hz, 1H), 7.40-7.10 (m, 10H), 4.51 (d, J=11.8 Hz, 1H), 5.27 (s, 1H), 3.08 (dd, J=7.4 Hz, 3.6 Hz, 1H), 2.90-2.80 (m, 2H), 2.49 (d, J=3 Hz, 1H), 1.25 (bt, J=7 Hz, 1H) ppm. $^{13}$C NMR ($CDCl_3$, 100 MHz) δ: 137.4, 137.3, 128.9, 128.4, 127.9, 127.4, 126.3, 125.6, 96.8, 94.7, 53.1, 40.8, 36.3 ppm. HRMS (ESI) [M+H]$^+$ calcd. For $C_{18}H_{19}N_2O_2$ 294.1441 found 294.1444.

Figure 4A:
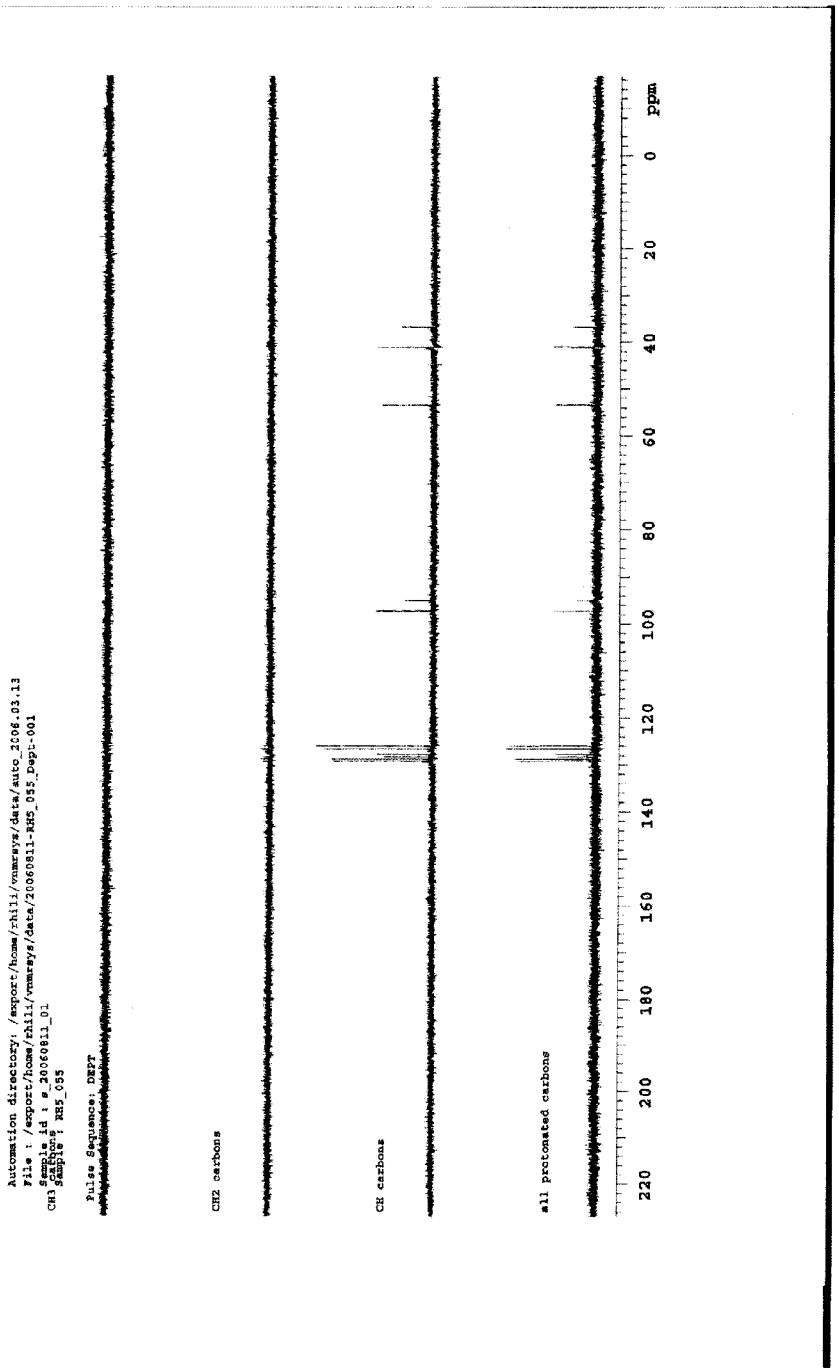
Figure 4B:
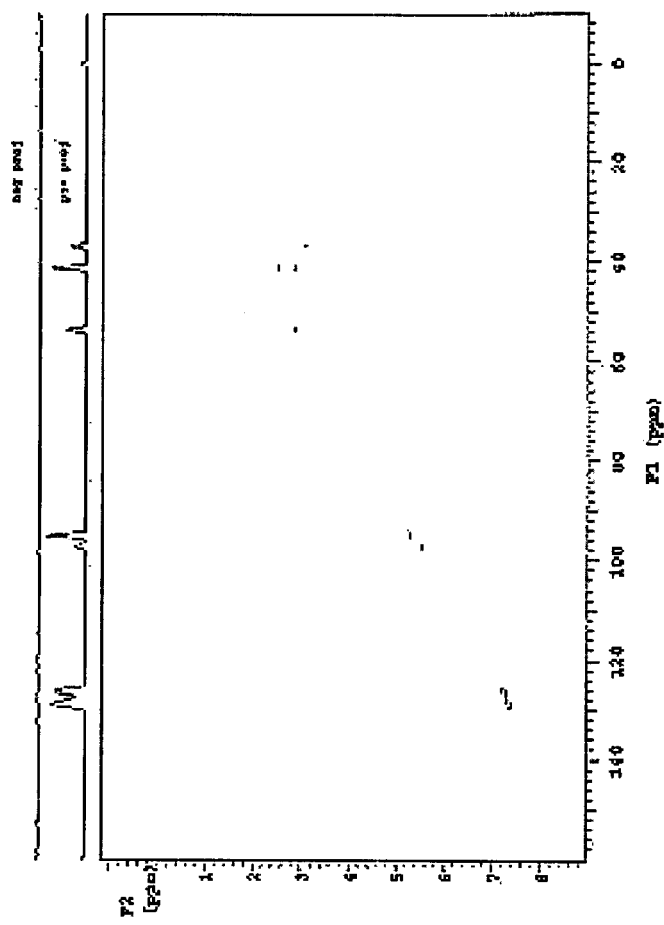
FIG. 4b illustrates the DEPT spectrum of 2a FIG. 5 illustrates the X-ray structure of anti-Pentacycle (5b).
Figure 5:
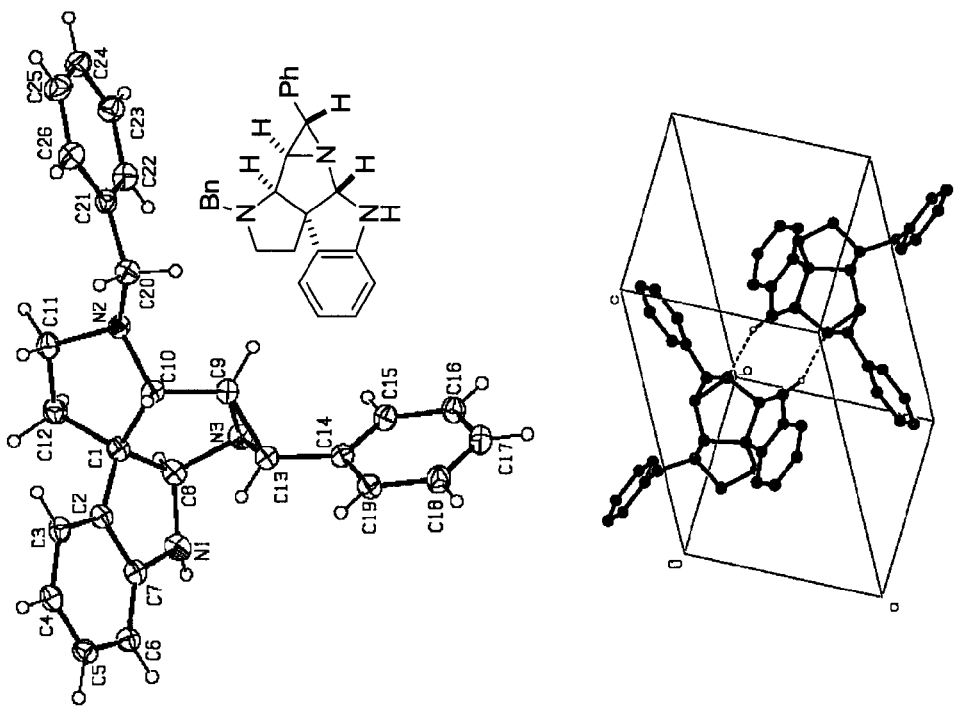

The $^{13}$C NMR spectrum exhibits only 3 aliphatic signals rather than the 4 expected for 2a (see FIG. 4a). However, the signal at 40.8 ppm is in fact 2 unique carbons exhibiting $^{13}$C NMR shifts that are indistinguishable at 100 MHz field strength. This was resolved by correlating results obtained by DEPT and hmqc NMR (see FIG. 4b). The DEPT spectrum of 2a renders the peak at 40.8 ppm as a CH-type carbon; however, hmqc clearly shows two hydrogens associated with the peak at 40.8 ppm. This structure has been verified using X-ray crystallography (FIG. 5).

Crystallization conditions: In a 2 ml vial, 10 mg of purified 2a was dissolved at saturation in toluene. The vial was placed in a 15 ml scintillation vial containing a small amount of pentane, capped tight and placed in the dark. After 48 hours, crystal formation was observed, and a suitable crystal was selected for X-ray crystallographic analysis.

Pentacycle Formation from 2a (Table 2, Entry 1)

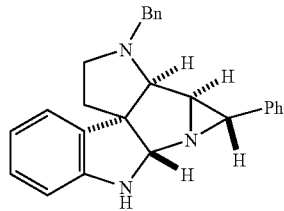

To a fully dissolved mixture of 2a (29.4 mg, 0.1 mmol) in 2 ml of trifluoroethanol at −20° C. was added N-benzyl tryptamine (33.6 mg, 0.21 mmol). The reaction was stirred at 0° C. until completion as determined by TLC and ESI MS. The mixture was then concentrated under reduced pressure and subjected to column chromatography eluting with hexanes/EtOAc (9:1) to afford the title compound in 92% yield (68.3 mg) as a 20:1 syn/anti diastereomeric mixture, both of which were yellow solids with Mp=53-55° C.

syn-pentacycle (5a) $^1$H NMR ($C_7D_8$, 400 MHz) δ: 7.28-6.99 (m, 12H), 6.78 (dt, J=7.2 Hz, 0.8 Hz, 1H), 6.40 (d, J=7.2 Hz, 1H), 4.43 (s, 1H), 4.40 (bs, 1H), 3.50 (d, 12.8 Hz, 1H), 3.33-3.28 (m, 2H), 3.01 (t, J=8.0 Hz, 1H), 2.55 (ddd, J=11.6 Hz, 8.8 Hz, 6.4 Hz, 1H), 2.01 (dd, J=4.8 Hz, 2.8 Hz, 1H), 1.84 (td, J=12.8 Hz, 7.2 Hz, 1H), 1.65 (ddd, 13.2 Hz, 6.8 Hz, 1.2 Hz, 1H) ppm. $^{13}$C NMR ($CDCl_3$, 50 MHz) δ: 148.2, 139.5, 138.7, 134.4, 128.83, 128.3, 128.1, 128.1, 126.9, 126.7, 126.0, 123.3, 118.9, 108.9, 92.8, 80.9, 71.4, 59.3, 57.9, 55.4, 44.2, 39.4 ppm. $R_f$=0.53 (7:3 hexanes/EtOAc).

anti-pentacycle (5b) $^1$H NMR ($CDCl_3$, 300 MHz) δ: 7.43-7.04 (m, 12H), 6.75 (td, J=7.8 Hz, 1.2 Hz, 1H), 6.56 (dd, J=8.1 Hz, 1.2 Hz, 1H), 5.18 (d, J=1.8 Hz, 1H), 4.64 (d, J=1.5 Hz, 1H), 4.08 (d, J=12.9 Hz, 1H), 3.62 (s, 1H), 3.61 (d, J=13.2 Hz, 1H), 3.12 (ddd, J=9.6 Hz, 6.6 Hz, 3.6 Hz, 1H), 2.81 (d, J=3.3 Hz, 1H), 2.70 (td, J=9.3 Hz, 6.9 Hz, 1H), 2.42 (d, J=3.0 Hz, 1H), 2.18 (ddd, J=12.9 Hz, 9.0 Hz, 6.6 Hz, 1H), 2.03 (ddd, J=12.9 Hz, 6.6 Hz, 3.9 Hz, 1H) ppm. $^{13}$C NMR ($CDCl_3$, 50 MHz) δ: 149.5, 139.7, 138.8, 134.2, 128.8, 128.3, 128.2, 128.1 127.0, 126.8, 126.1, 122.9, 118.9, 108.2, 90.8, 78.7, 67.1, 58.9, 56.4, 55.0, 41.4, 38.0 ppm. HRMS (ESI) [M+H]$^+$ calcd. For $C_{26}H_{26}N_3$ 380.2121 found 380.2126. $R_f$=0.30 (EtOAc).

Crystallization conditions: In a 2 ml vial, 10 mg of purified anti-pentacycle was dissolved at saturation in toluene. The vial was placed in a 15 ml scintillation vial containing a small amount of pentane, capped tight and placed in the dark. After 48 hours, crystal formation was observed, and a suitable crystal was selected for X-ray crystallographic analysis.

Compound 7 Via Ring-Opening of Pentacycle 5b (Scheme 12)

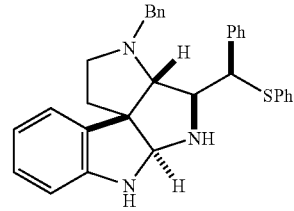

In a flame-dried reaction tube equipped with a stirring bar and a rubber septum connected to a $N_2$ inlet was placed 5b (56.85 mg, 0.15 mmol) dissolved into 1 ml of $CH_2Cl_2$. Benzenethiol (17 ul, 0.16 mmol) was added followed by $Zn(OTf)_2$ (3 mg, 0.008 mmol). The reaction was stirred at room temperature under a nitrogen atmosphere for 1 hour, at which point TLC showed the disappearance of starting material. Water was then added to the reaction mixture, and $CH_2Cl_2$ was used three times to extract the product from the reaction mixture. The combined organic layers were washed with saturated aqueous $NaHCO_3$, water, and brine. The organic layer was dried over $Na_2SO_4$, filtered and concentrated under reduced pressure. The resulting crude solid was subjected to flash column chromatography (silica gel; 5% MeOH in $CH_2Cl_2$, $R_f$=0.29) to afford pure thiol-opened product in 94% yield as a brown solid Mp=64-65° C. $^1$H NMR (400 MHz. $CDCl_3$) δ: 7.46-6.90 (m, 15H), 6.80 (td, J=7.6 Hz, 1.2 Hz, 1H), 6.75 (d, J=6.8 Hz, 2H), 6.58 (d, J=7.6 Hz, 1H), 5.03 (s, 1H), 4.36 (d, J=13.2 Hz, 1H), 3.87 (d, J=12 Hz, 1H), 3.77 (d, J=12 Hz, 1H), 3.65 (s, 1H), 3.53 (d, J=13.2 Hz, 1H), 3.20-2.60 (bs, 2H), 3.15 (td, J=7.6 Hz, 1.2 Hz, 1H), 2.62 (m, 1H), 2.26 (dd, J=12.8 Hz, 6.8 Hz, 1H), 2.14 (ddd, J=13.2 Hz, 10.8 Hz, 7.6 Hz, 1H) ppm $^{13}$C NMR (50 MHz. $CDCl_3$) 3: 149.1, 142.3, 135.1, 131.7, 129.4, 128.9, 128.60, 128.6, 128.5, 127.4, 127.1, 126.8, 124.1, 119.3, 108.9, 88.1, 83.1, 68.4, 64.6, 59.3, 57.7, 55.6, 31.9 ppm. HRMS (ESI) [M+H]$^+$ calcd. For $C_{32}H_{32}N_3S$ 490.2311 found 490.2323.

The stereochemistry of 7 produced by $S_N2$ ring-opening of 5b was verified through the 1D and 2D NMR analysis of the following derivative:

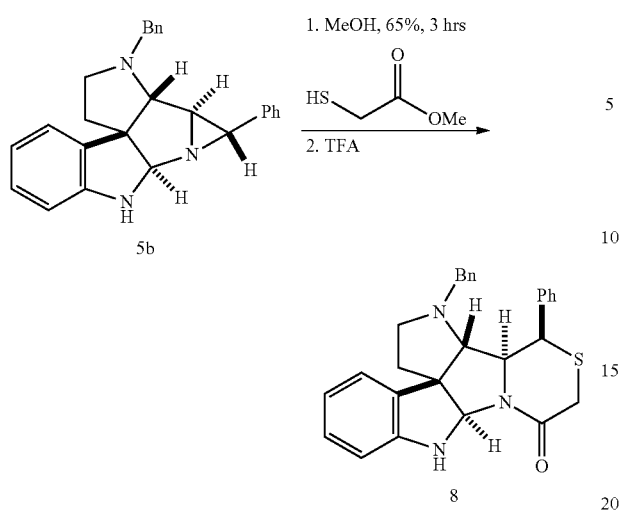

To a flame dried flask equipped with a magnetic stirring bar and a rubber septum with nitrogen gas inlet was added 5b (113.7 mg, 0.3 mmol) and mercaptomethylacetate (36 ul, 0.33 mmol) to 2 ml of dry methanol. The reaction was then heated to 65° C. for 3 hours then cooled to room temperature. The mixture was then poured into an aqueous solution of NaOH (10%) and extracted with ether 3 times. The aqueous layer was then adjusted to pH 7 and extracted 5 times with methylene chloride. The combined organic layered were dried over $Na_2SO_4$ and then concentrated under reduced pressure. The off white powder was then dissolved into 2 ml of TFA and stirred for 16 hours. The residue was then diluted with 10 ml of phosphate buffer pH 7.4 and extracted 5 times with methylene chloride. The organic layers were then dried over $Na_2SO_4$ and concentrated over reduced pressure. The brown foam was then subjected to flash column chromatography (silica; 5% MeOH in $CH_2Cl_2$) to afford pure 8 ($R_f$=0.26, 5% MeOH in $CH_2Cl_2$) as a greyish brown foam in 47% yield. $^1$H NMR (400 MHz. $CDCl_3$) δ: 7.42-7.28 (m, 5H), 6.91 (td, J=7.6 Hz, 1.2 Hz, 1H), 6.87-6.82 (m, 1H), 6.80-6.72 (m, 4H), 6.54 (dd, J=8.8 Hz, 0.8 Hz, 1H), 6.45 (dd, J=7.6 Hz, 1.2 Hz, 1H), 6.41 (d, J=7.6 Hz, 1H), 5.43 (s, 1H), 5.29 (s, 1H), 5.25 (bs, 1H), 4.12 (t, J=4.0 Hz, 1H), 3.87 (m, 2H), 3.72 (d, J=13.2 Hz, 1H), 3.47 (d, J=15.6 Hz, 1H), 14.2 (d, J=14.8 Hz, 1H), 3.16-3.08 (m, 2H), 2.80 (ddd, J=10.4 Hz, 8.0 Hz, 6.8 Hz, 1H), 2.15 (m, 1H), 2.00 (ddd, J=11.6 Hz, 6.4 Hz, 5.2 Hz, 1H) ppm. $^{13}$C NMR (50 MHz. $CDCl_3$) δ: 169.3, 147.9, 138.7, 137.7, 131.7, 129.2, 129.0, 128.8, 128.3, 127.9, 127.85, 127.8, 122.6, 119.3, 108.7, 83.8, 79.0, 68.2, 62.7, 59.7, 55.7, 47.2, 39.9, 30.7 ppm. HRMS (ESI) [MH]+ calcd. for $C_{28}H_{28}N_3OS$ 454.1947 found 454.1944.

trans-(3-Phenylaziridin-2-yl)-methanol (3)

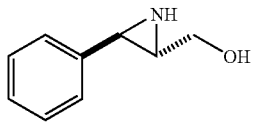

To a flame dried round bottom flask was added 2a (62.3 mg, 0.25 mmol) dissolved in a mixture of 1 ml of MeOH and 1 ml of THF. The reaction vessel was cooled to 0° C. and $NaBH_4$ (37.83 mg, 1 mmol) was added to the reaction. The reaction was stirred at 0° C. for 90 minutes when TLC showed completion of reaction, then water and ether were added and the organic layer was extracted three times. The combined organic phases were dried over $Na_2SO_4$, filtered and concentrated under reduced pressure to afford the title compound as a colourless oil in quantitative yield. The NMR spectra are in accordance with literature (Bartnik. R. Bull. Pol. Acad. Sci. Chem. 1986, 34, 27). $^1$H NMR (200 MHz. $CDCl_3$) (δ: 7.30-7.00 (m, 5H), 3.82 (dd, J=12.2 Hz, 3.2 Hz, 1H), 3.50 (dd, J=12.0 Hz, 5.4 Hz, 1H), 3.30-2.60 (bs, 2H), 2.81 (d, J=3.2 Hz, 1H), 2.31 (m, 1H) ppm. $^{13}$C NMR (50 MHz. $CDCl_3$) δ: 139.3, 128.7, 127.4, 125.9, 62.1, 42.0, 36.6 ppm.

Trans-Phenyl-(3-phenylaziridin-2-ylmethyl)-amine (4)

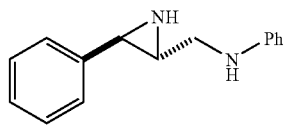

In a flamed-dried round bottom flask equipped with a rubber septum in order to maintain a nitrogen atmosphere was added 2a (58.8 mg, 0.2 mmol) and aniline (43.7 μl, 0.48 mmol) dissolved in 5 ml of anhydrous MeOH. The reaction was stirred for 10 minutes, then $NaCNBH_3$ (40.2 mg, 0.64 mmol) was added. The reaction was allowed to stir for 5 hours while maintaining pH 7 through addition of acetic acid when required. $NaHCO_3$ was then carefully added to the reaction mixture and stirred for 5 minutes. Water was added and the aqueous mixture was extracted 3 times with $Et_2O$. The collected organic phases were washed with water, then brine, and dried over $Na_2SO_4$ and concentrated under reduced pressure. The crude product was purified using flash column chromatography (silica gel; 5% MeOH in $CH_2Cl_2$) to afford the title compound as a white solid in 99% yield. Mp=96-97° C. $^1$H NMR (200 MHz. $CDCl_3$) δ:7.40-7.10 (m, 7H), 6.78-6.62 (m, 3H), 3.51 (dd, J=13.6 Hz, 4.2 Hz, 1H), 3.4 (very bs, 2H), 3.28 (dd, J=13.6 Hz, 7.5 Hz, 1H), 2.86 (d, J=2.8 Hz, 1H), 2.50-2.35 (m, 1H) ppm. $^{13}$C NMR (50 MHz. $CDCl_3$) δ: 148.3, 139.7, 129.5, 129.4, 128.8, 127.4, 125.8, 118.1, 115.3, 113.2, 46.4, 40.3, 38.0 ppm. $R_f$=0.14 (7:3 hexanes/EtOAc).

2-Phenylacrylic Acid Methyl Ester

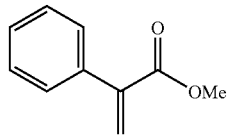

The compound was synthesized according to a literature method (Ames and Davey J. Chem. Soc. 1958, 1798). To a solution of phenylacetic acid methyl ester (13.58 ml, 100 mmol) in 35 ml of benzene was added diethyl glyoxalate (20.72 ml, 130 mmol). The solution was allowed to stir at room temperature for 1 hour at which point a solid mass was obtained. Suspending the mass in ether followed by filtration yielded a white powder. The white powder was then suspended in ether and acidified using 5% HCl. The aqueous layer was then removed and the ether layer was washed with saturated NaHCO$_3$, H$_2$O, and brine, dried over MgSO$_4$ and then concentrated under reduced pressure. The resulting yellow oil was charged with 45 ml of 37% formaldehyde solution (in water) and 100 ml of water at room temperature. 40 g K$_2$CO$_3$ in 50 ml of water was added via addition funnel to the reaction mixture over a period of 30 minutes. The reaction was then stirred for a further 2 hours at room temperature. The resulting mixture was extracted with ether three times, and the resulting ethereal solution was washed with water, brine, dried over MgSO$_4$, and subjected to Kugelrohr distillation (83° C., 0.5 mmHg) to afford the title compound as an oil (81% yield, 14.1 g). $^1$H NMR (CDCl$_3$, 300 MHz) δ:7.50-7.30 (m, 5H), 6.35 (d, J=1.2 Hz, 1H), 5.90 (d, J=1.2 Hz, 1H), 4.31 (q, J=7.2 Hz, 2H), 1.36 (t, J=7.2 Hz, 3H) ppm.

2-Phenyloxirane-2-carboxylic Acid Methyl Ester

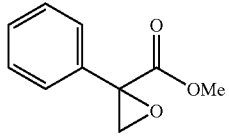

The title compound was synthesized according to a literature method (Whitman *Tetrahedron* 1985, 41, 1183). To a mixture of 2-phenylacrylic acid methyl ester (7.92 g, 45 mmol) in 60 ml of methylene chloride was added mCPBA (13.1 g, 58.5 mmol) and the reaction was stirred at 45° C. overnight. The reaction mixture was then filtered and the solid was washed with methylene chloride. The filtrate was washed three times with 50 ml of equal parts solution consisting of saturated Na$_2$S$_2$O$_3$ and saturated NaHCO$_3$. The organic layer was washed with water and brine, dried over MgSO$_4$, and concentrated under reduced pressure to afford the title compound in greater than 95% purity according to $^1$H NMR (85% yield). $^1$H NMR (CDCl$_3$, 300 MHz) δ: 7.50-7.30 (m, 5H), 4.22 (q, J=7.2 Hz, 2H), 3.40 (d, J,=7.1 Hz, 1H), 2.95 (d, J=7.1 Hz, 1H), 1.26 (t, J=7.2 Hz, 3H) ppm.

2-Phenylaziridine-2-carboxylic Acid Ethyl Ester (1b)

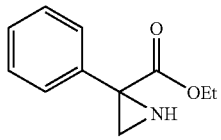

To a mixture of 2-phenyloxirane-2-carboxylic acid methyl ester (7 g, 36.5 mmol) and sodium azide (7.09 g, 109 mmol) in 90 ml of EtOH was added NH$_4$Cl (5.83 g, 109 mmol). The reaction mixture was stirred at 65° C. overnight, at which point it was concentrated under reduced pressure. The residue was dissolved in EtOAc and washed with water and brine, then dried over Na$_2$SO$_4$ and concentrated under reduced pressure to afford the azido alcohol as an oil. This material was then dissolved in 125 ml of acetonitrile and heated to 50° C. PPh$_3$ (10.6 g, 40.5 mmol) was added slowly (N$_2$ is evolved). Once all the PPh$_3$ was added, the reaction vessel was fitted with a reflux condenser and heated at 83° C. for 5 hrs or when the reaction was completed by TLC. The resulting mixture was filtered and the filtrate concentrated under reduced pressure. To the residue was added 5% EtOAc in pentane and the precipitate was filtered off. The filtrate was then subjected to silica gel column chromatography using 10% EtOAC in hexanes to afford the title compound as an oil in 75% yield (7.88 g) over two steps. The NMR spectra were in accordance with literature values (Li, H.; Wang, B.; Deng, L. *J. Am. Chem. Soc.* 2006, 128, 732). $^1$HNMR (CDCl$_3$, 300 MHz) δ: 7.60-7.20 (m, 5H),2.48 (m 1H), 1.98 (d, J=6.2 Hz, 2H) 1.21 (t, J=7.0 Hz, 3H) ppm. $^{13}$C NMR (CDCl$_3$, 50 MHz) δ: 172.8, 136.6, 129.0, 127.8, 127.5, 61.9, 60.0, 41.1, 35.2, 20.7, 14.0, 13.9 ppm. (ESI MS) M$^+$H=192.2.

5-Phenyl-2-(2-phenylaziridin-2-yl)-3-oxa-1-azabicyclo[3.1.0]hexan-4-ol (2b)

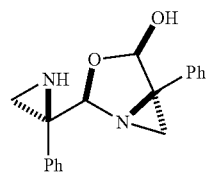

In a Hanle dried 100 ml Schlenk tube equipped with a magnetic stirring bar was placed 1b (2.1 g, 11 mmol) in 36 ml of toluene. The solution was cooled to −78° C. and a 1.5M solution of DIBAL in toluene (14.6 ml, 22 mmol) was added dropwise along the wall of the vessel. Once the addition was complete, the reaction was allowed to stir at −78° C. for another hour at which point ESI MS showed the disappearance of starting material. MeOH was slowly added along the wall of the vessel at −78° C. The reaction mixture was then allowed to stir for 30 minutes while warming to room temperature. Saturated Na$_2$SO$_4$ was then added and the solution was allowed to stir for another 15 minutes. The reaction was then filtered and water and ether was added. The organic later was extracted from the partition three times, washed with brine, dried over Na$_2$SO$_4$ and concentrated under reduced pressure. The resulting white solid may be crystallized from EtOAc or MeOH to afford the title compound in 81% yield as a white solid. Mp=53-55° C. $^1$H NMR (CDCl$_3$, 300 MHz) δ: 7.70 (d, J=11 Hz, 1H) 7.64-7.20 (m, 10H), 5.66 (d, J=11 Hz, 1H), 5.05 (s, 1H), 2.31 (d, J=5.2 Hz, 1H), 2.00 (d, J=8.2 Hz, 1H), 1.83 (s, 1H), 1.76 (s, 1H), 1.30-1.10 (bs, 1H) ppm. $^{13}$C NMR (CDCl$_3$, 50 MHz) δ: 139.09, 136.69, 129.04, 128.48, 128.16, 128.11, 128.05, 127.12, 97.95, 97.88, 54.53, 44.22, 37.13, 28.72 ppm. HRMS (ESI) [M+H]$^+$ calcd. For C$_{18}$H$_{19}$N$_2$O$_2$ 294.1441 found 294.1449.

Pentacycle Formation from 2b (Table 2, Entry 2)

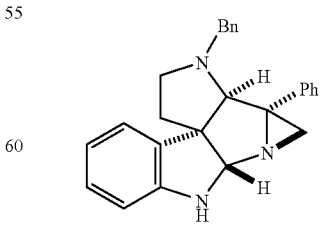

In a name-dried flask equipped with a Teflon-coated magnetic stirring rod and a rubber septum was placed N-benzyl tryptamine (629 mg, 2.52 mmol), which was fully dissolved in 4 ml of trifluoroethanol. 2b (370 mg, 1.26 mmol) was then added to the reaction, and the vessel was heated to 40° C. until completion of reaction (approximately 8 hours) as determined by TLC (80:20 hexanes/acetone, $R_f$=0.31 (syn isomer) and 0.25 (anti isomer). The crude material was subjected to flash column chromatography (silica gel; 80:20 hexanes/acetone) to afford the pure syn-diastereoisomer and a syn/anti mixture of diastereoisomers as pale yellow solids in 81% yield (2:1, syn/anti). Mp=54-56° C.

syn-pentacycle: $^1$H NMR (CDCl$_3$, 400 MHz) δ: 7.34-7.24 (m, 5H), 7.18-7.09 (m, 5H), 7.02-6.98 (m, 2H), 6.79 (td, J=7.6 Hz, 1.2 Hz, 1H), 6.68 (d, J=7.6 Hz, 1H), 4.56 (s, 1H), 4.11 (d, J=12.4 Hz, 1H), 3.69 (s, 1H), 3.33 (d, J=13.2 Hz, 1H), 3.19 (t, J=8 Hz, 1H), 3.00 (s, 1H), 2.70 (ddd, J=11.2 Hz, 9.6 Hz, 7.2 Hz, 1H), 2.46 (s, 1H), 2.19 (ddd, J=13.2 Hz, 11.2 Hz, 7.6 Hz, 1H), 1.90 (dd, J=12.8 Hz, 6 Hz, 1H), 1.72-1.58 (m, 1H) $^{13}$C NMR (CDCl$_3$, 100 MHz) δ: 148.7, 141.2, 139.2, 134.0, 128.9, 128.6, 128.6, 128.5, 127.8, 127.4, 127.3, 123.9, 119.5, 109.5, 93.6, 85.5, 77.6, 73.0, 58.7, 56.6, 39.1, 38.6 ppm. $R_f$=0.31 (8:2 hexanes/acetone).

anti-pentacycle: $^1$H NMR (CDCl$_3$, 400 MHz) δ: 7.34-7.24 (m, 5H), 7.18-7.09 (m, 5H), 6.95-6.91 (m, 2H), 6.77 (td, J=7.6 Hz, 1.2 Hz, 1H), 6.59 (d, J=7.6 Hz, 1H), 5.24 (s, 1H), 4.65 (bs, 1H), 3.80 (s, 1H), 3.50 (d, J=12.8 Hz, 1H), 3.17 (d, J=12.8 Hz, 1H), 3.04 (td, J=10.2 Hz, 7.2 Hz, 1H, 1H), 2.59 (m, 1H), 2.33 (d, J=8 Hz, 1H), 2.14 (m, 1H), 1.75-1.70 (m, 1H). ppm. $^{13}$C NMR (CDCl3, 100 MHz) δ: 148.6, 139.3, 134.8, 129.2, 128.9, 128.2, 128.0, 127.9, 127.3, 127.2, 126.8, 122.7, 118.9, 108.4, 89.3, 81.4, 68.2, 60.7, 55.0, 37.2, 28.8 ppm. HRMS (ESI) [M+H]$^+$ calcd. For C$_{26}$H$_{26}$N$_3$ 380.2121 found 380.2127. $R_f$=0.25 (8:2 hexanes/acetone).

trans-3-Thiophen-2-yl-oxirane-2-carboxylic acid ethyl ester

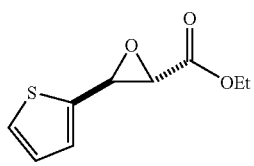

The title compound was synthesized using a literature method (Alcaide, B.; Biurrun, C.; Martinez, A.; Plumet, J. *Tetrahedron Lett.* 1995, 36, 5417). To a solution of thiophene-2-carboxaldehyde (6.33 ml, 69 mmol) and chloroethylacetate (7.35 ml, 69 mmol) in 130 ml of ether was added freshly made NaOEt (4.7 g, 69 mmol) over a period of one hour. The solution was allowed to stir overnight at room temperature. The reaction mixture was then filtered and the filtrate was partitioned between water and ether. The ether layer was extracted and washed with water, brine, dried over MgSO$_4$ and concentrated under reduced pressure. The residue was subjected to silica gel column chromatography (10% EtOAc in hexanes containing 1% NEt$_3$, $R_f$=0.55). The title compound was isolated as a red oil in 64% yield. $^1$H NMR (CDCl$_3$, 200 MHz) δ:7.30 (d, J=5.0 Hz, 1H), 7.17 (d, J=3.4 Hz, 1H), 6.99 (dd, J=5.0 Hz, 3.4 Hz, 1H), 4.33 (s, 1H), 4.28 (qd, J=7.0 Hz, 2.0 Hz, 2H), 3.68 (d, J=2.0 Hz, 1H), 1.33 (t, J=7.0 Hz, 3H) ppm. $^{13}$C NMR (CDCl$_3$, 100 MHz) δ: 168.0, 138.6, 127.5, 127.4, 126.3, 69.1, 57.5, 54.9, 14.3 ppm.

trans-3-Thiophen-2-yl-aziridine-2-carboxylic Acid Ethyl Ester (1c)

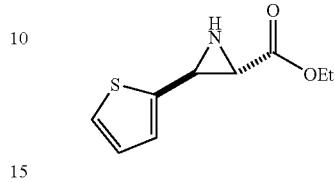

In a round bottom flask equipped with a magnetic stirring bar and a reflux condenser was added 3-thiophen-2-yl-oxirane-2-carboxylic acid ethyl ester (2.2 g, 11 mmol), and NaN$_3$ (2.15 g, 33 mmol) in 25 ml of MeOH. NH$_4$Cl (1.77 g, 33 mmol) was then added and the reaction mixture was heated to 65° C. and stirred for 4 hours. The reaction mixture was then concentrated under reduced pressure and the residue was dissolved in EtOAc and washed with water and brine, dried over Na$_2$SO$_4$ and concentrated under reduced pressure. The residue was then dissolved in 35 ml acetonitrile and heated to 50° C. in a round bottom equipped with a condenser. PPh$_3$ (3.18 g, 12.1 mmol) was added slowly (N$_2$ evolved) and then the flask was fitted with a condenser and heated to 83° C. for 2 hours. The resulting mixture was filtered and the filtrate concentrated under reduced pressure. To the residue was added 5% EtOAc in pentane and the precipitate was filtered off. The filtrate was then subjected to silica gel column chromatography using 10% EtOAC in hexanes to afford the title compound as a purple oil in 62% yield over two steps. The NMR spectra were in accordance with literature (Solladie-Cavallo, A.; Lupattelli, P.; Bonini, C; De Bonis, M. *Tetrahedron Lett.* 2003, 44, 5075). $^1$H NMR (CDCl3, 300 MHz) δ: 7.22 (d, J=5.0 Hz, 1H), 7.09 (d, J=3.4 Hz, 1H), 6.99 (dd, J=5.0 Hz, 3.4 Hz, 1H), 4.30 (qd, J=7.0 Hz, 1.6 Hz, 2H), 3.54 (d, J=7.0 Hz, 1H), 2.73 (d, J=6.2 Hz, 1H), 2.2-1.9 (bt, 1H), 1.37 (t, J=7.0 Hz, 3H) ppm. $^{13}$C NMR (CDCl3, 50 MHz) δ: 171.3, 142.6, 127.1, 125.3, 124.5, 61.7, 40.4, 37.0, 14.23 ppm. (ESI MS) [MH]$^+$=198.1

6-Thiophen-2-yl-2-(3-thiophen-2-yl-aziridin-2-yl)-3-oxa-1-azabicyclo[3.1.0]hexan-4-ol (2c)

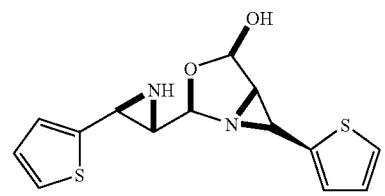

In a flame dried 100 ml Schlenk tube equipped with a magnetic stirring bar was placed 1c (0.6 g, 3.05 mmol) in 10 ml toluene. The solution was cooled to −78° C. and a 1.5M solution of DIBAL in toluene (4 ml, 6 mmol) was added dropwise along the wall of the vessel. Once the addition was complete, the reaction was allowed to stir at −78° C. for another hour at which point ESI MS showed the lack of starting material. MeOH was slowly added along the wall of the vessel at −78° C. The reaction mixture was then allowed to stir for 30 minutes while warming to room temperature. Saturated Na$_2$SO$_4$ was then added and the solution was allowed to stir for another 15 minutes. The reaction was then filtered and water and ether was added. The organic later was extracted from the partition three times, washed with brine, dried over Na$_2$SO$_4$ and concentrated under reduced pressure. The resulting white solid may be crystallized from EtOAc or MeOH to afford the title compound in 92% (428 mg) yield as a white solid. Silica column chromatography is not recommended. Mp=149-153° C. (decomp.) $^1$H NMR (CDCl$_3$, 200 MHz) (δ: 7.66 (d, J=11.6 Hz, 1H), 7.23-7.18 (m, 2H), 7.02-6.94 (m, 4H), 5.48 (d, J=11.6 Hz, 1H), 3.27 (dd, J=7.0 Hz, 3.4 Hz, 1H), 2.99 (dd, J=9.0 Hz, 3.4 Hz), 2.90 (d, J=2.6 Hz, 1H), 2.75 (d, J=2.6 Hz, 1H), 1.17 (t, J=6.6 Hz, 1H) ppm. $^{13}$C NMR (CDCl3, 75 MHz) δ: 141.5, 121.4, 127.7, 127.3, 125.9, 125.1, 124.8, 124.6, 96.9, 94.4, 54.0, 41.5, 37.5, 32.5 ppm. HRMS (EI) of aldehyde monomer: 152.9561

(S,S) Diethyl aziridine-2,3-dicarboxylate

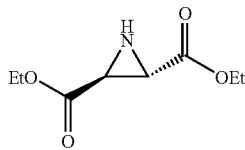

The title compound was prepared using a literature method (Bruening, A.; Vicik, R.; Schirmeister, T. *Tetrahedron: Asymmetry*, 2003, 14, 3301). In a round bottom flask equipped with a Teflon coated magnetic stirring bar and pressure equalizing addition funnel was placed L-diethyl-tartrate (17.73 g, 86 mmol). The reaction was cooled to 0° C. and then SOCl$_2$ (7.3 ml, 100 mmol) was added dropwise through the addition funnel over a period of 15 minutes. After the addition was complete, 20 drops of anhydrous DMF was added to the reaction mixture and the vessel was first allowed to warm to room temperature, and then it was heated at 50° C. for 30 minutes. The reaction was allowed to cool back to room temperature and N$_2$ was bubbled through for 1 hour in order to remove excess SOCl$_2$ and liberated acidic components. The mixture was then concentrated using rotary evaporator at 50° C. to remove residual SOCl$_2$, then further concentrated under high vacuum to afford the cyclic sulfite as a pale yellow oil. The cyclic sulfite (21.67 g, 86 mmol) was then dissolved in 50 ml of anhydrous DMF. NaN$_3$ (16.77 g, 258 mmol) was then added to the solution and the reaction was allowed to stir for 24 hours. 50 ml of CH$_2$Cl$_2$ and 60 ml of water were then added to the reaction, and stirred for 2 hours. The aqueous phase was extracted three times with CH$_2$Cl$_2$ and the collected organic phases were dried over Na$_2$SO$_4$ and concentrated under reduced pressure to afford the azido alcohol in 95% yield (18.87 g, 81.7 mmol) over two steps as a yellow oil, which was pure by NMR and carried over to the next step. The azido alcohol (18.87 g, 81.7 mmol) was dissolved into 400 ml of anhydrous DMF and cooled to 0° C. PPh$_3$ (22.5 g, 85.79 mmol) was added in portions over a period of 30 minutes. The reaction vessel was then allowed to warm to room temperature and stirred at this temperature of 90 minutes. The reaction vessel was then warmed to 85° C. and stirred until completed by TLC (3:1 Et$_2$O/hexanes, R$_f$=0.34). The reaction was then concentrated under reduced pressure and purified by flash column chromatography (silica gel; gradient 9:1-7:3 hexanes/EtOAc) to afford the title compound as a pale yellow oil in 79% yield (12.1 g). $^1$H NMR (CDCl$_3$, 400 MHz) 4.30 (m, 4H), 2.87 (dd, J=9.2 Hz, 3.2 Hz, 2H), 1.82 (bt, J=9.2 Hz, 1H), 1.31 (dt, J=10.4 Hz, 7.2 Hz, 6H) ppm. $^{13}$C NMR (CDCl$_3$, 50 MHz) δ: 170.6, 168.9, 62.4, 61.8, 36.3, 35.5, 14.2 ppm.

(S,S) 3-Hydroxymethylaziridine-2-carboxylic Acid Ethyl Ester

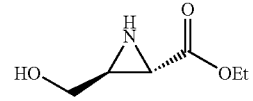

In a round bottom flask equipped with a magnetic stirring bar and a septum was placed (S,S) diethyl aziridine-2,3-dicarboxylate (1.87 g, 10 mmol) dissolved into 30 ml of EtOH. The vessel was cooled to 0° C. and NaBH$_4$ (302.6 mg, 8 mmol) was added slowly. The reaction mixture was allowed to stir at 0° C. until the reaction was complete according to TLC (EtOAc, R$_f$=0.66), which was approximately 2 hours. The reaction was quenched by the addition of pH 7 phosphate buffer, and extracted three times with CH$_2$Cl$_2$. The combined organic layers were dried over Na$_2$SO$_4$ and concentrated under reduced pressure. The residue was purified by flash column chromatography (silica gel; gradient 8:2 EtOAc/hexanes—100% EtOAc) to afford the title compound in 84% yield as a pale yellow oil. $^1$H NMR (CDCl$_3$, 200 MHz) δ: 4.22 (q, J=7.0 Hz, 2H), 3.82 (dd, J=12.4 Hz, 2.8 Hz, 1H), 3.48 (dd, J=12 Hz, 4.8 Hz, 1H), 2.46 (m, 2H), 1.50 (bs, 1H), 1.31 (t, J=7.0 Hz, 3H) ppm. $^{13}$C NMR (CDCl$_3$, 50 MHz) δ: 172.2, 62.0, 61.5, 39.8, 32.7, 14.3 ppm. HRMS (ESI) [M+H]$^+$ calcd. for C$_6$H$_{12}$NO$_3$ 146.0817, found 146.0820.

3-(tert-Butyldimethylsilanyloxymethyl)-aziridine-2-carboxylic Acid Ethyl Ester (1e)

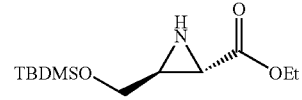

In a flame dried flask equipped with a magnetic stirring rod and a rubber septum with a N$_2$ inlet was added (S,S) 3-hydroxymethylaziridine-2-carboxylic acid ethyl ester (296 mg, 2.04 mmol) and 12 ml of CH$_2$Cl$_2$. The reaction vessel was cooled to 0° C. then TBDMSCl (377 mg, 2.50 mmol) and DMAP (623 mg, 5.1 mmol) was added. The reaction was allowed to stir for 1 hour at 0° C. then at room temperature until the reaction was completed according to TLC (R$_f$=0.65; 7:3 hexanes/EtOAc). The reaction was diluted with CH$_2$Cl$_2$ then water was added. The organic layer was extracted three times, and the combined organic layers were washed first with saturated NaHCO$_3$, then water, then brine and dried over solid Na$_2$SO$_4$. The mixture was filtered and dried under reduced pressure to afford a pale yellow oil, which was subjected to flash column chromatography (silica gel; 8:2 hexanes/EtOAc) to afford the title compound as a thick colourless oil in 99% yield. $^1$H NMR (CDCl$_3$, 400 MHz) δ: 4.21 (q, J=3.6 Hz, 2H), 3.66 (dd, J=11.2 Hz, 5.2 Hz, 1H), 3.56 (dd, 10.8 Hz, 4.8 Hz, 1H), 2.42 (m, 2H), 1.37 (bt, 1H), 1.29 (t, J=7.2 Hz, 3H) ppm. $^{13}$C NMR (CDCl$_3$, 100 MHz) δ: 172.6, 64.8, 61.7, 40.3, 33.7, 26.1, 18.5, 14.4, −5.1 ppm. HRMS (ESI) [M+H]⁺ calcd. for $C_{12}H_{25}NO_3Si$ 260.1676, found 260.1675.

6-(tert-Butyldimethylsilanyloxymethyl)-2-[3-(tert-butyldimethylsilanyloxymethyl)-aziridin-2-yl]-3-oxa-1-azabicyclo[3.1.0]hexan-4-ol (2e)

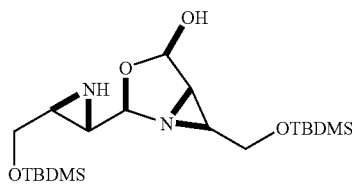

In a flame dried 100 ml Schlenk tube equipped with a magnetic stirring bar was placed 1e (400 mg, 1.54 mmol) in 6 ml of toluene. The solution was cooled to −78° C. and a 1.5M solution of DIBAL in toluene (2.2 ml, 3.3 mmol) was added dropwise along the wall of the vessel. Once the addition was complete, the reaction was allowed to stir at −78° C. for another hour at which point TLC showed the lack of starting material. MeOH was slowly added along the wall of the vessel at −78° C. The reaction mixture was then allowed to stir for 30 minutes while warming to room temperature. Saturated $Na_2SO_4$ was then added and the solution was allowed to stir for another 15 minutes. The reaction was then filtered and water and ether were added. The organic layer was extracted three times, washed with brine, dried over $Na_2SO_4$ and concentrated under reduced pressure. The resulting clear oil was pure by NMR analysis and was used in subsequent transformations. TLC (7:3, hexanes/EtOAc $R_f$=0-0.55 streaking. ¹H NMR (CDCl₃, 400 MHz) δ: 8.20-8.05 (bs, 1H) 5.29 (bs, 1H), 4.95 (s, 1H), 3.86-3.85 (m, 2H), 3.65 (dd, J=11.2 Hz, 6 Hz, 1H), 3.56 (dd, J=11.6 Hz, 5.6 Hz, 1H), 2.53 (d, J=2.8 Hz, 1H), 2.39 (bs, 1H), 2.13 (bs, 1H), 1.65 (sextet, J=2.8 Hz), 1.20 (bs, 1H), 0.89 (s, 9H), 0.87 (s, 9H), 0.07 (ds, 6H), 0.04 (ds, 6H) ppm ¹³C NMR (CDCl₃, 100 MHz) δ: 96.5, 94.7, 64.0, 58.4, 48.5, 40.3, 34.0, 33.5, 26.1, 26.0, 18.6, 18.5, −4.9, −5.0, −5.3, −5.4 ppm. HRMS (ESI) [MH]⁺ calcd. For $C_{20}H_{43}N_2O_4Si_2$ 431.2755, found 431.2749.

Pentacycle Formation from 2e (Table 2, Entry 4)

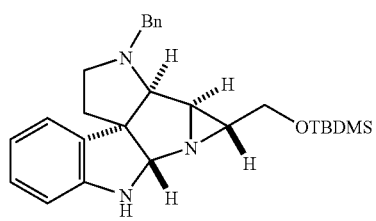

In a flame dried flask equipped with a rubber septum attached to a $N_2$ source and a magnetic stirring bar was added N-benzyl tryptamine (325 mg, 1.3 mmol) dissolved in 2 ml of trifluoroethanol. The reaction mixture was cooled to −20° C. and 2e (275 mg, 0.65 mmol) dissolved into 2 ml of trifluoroethanol was added to the reaction. The resulting mixture was stirred for 12 hours, at which point TLC analysis indicated consumption of amino aldehyde. The reaction mixture was concentrated under reduced pressure and subjected to flash column chromatography (silica gel; 8:2 hexanes/EtOAc for syn-isomer, then 5% MeOH in $CH_2Cl_2$ for anti-isomer) to yield the syn-diastereoisomer as a thick colourless oil and the anti-diastereoisomer as a thick pale orange oil.

syn-pentacycle: ¹H NMR (CDCl₃, 400 MHz) δ: 7.42-7.22 (m, 5H), 7.15 (d, J=7.6 Hz, 1H), 7.07 (td, J=7.6 Hz, 1.2 Hz, 1H), 6.77 (t, J=7.2 Hz, 1H), 6.58 (d, J=7.6 Hz, 1H), 4.63 (s, 1H), 4.52 (s, 1H), 3.81 (d, J=12.4 Hz, 1H), 3.56 (d, J=12.8 Hz, 1H), 3.49 (d, J=4.8 Hz, 1H), 3.46-3.36 (m, 2H), 3.25 (m, 1H), 2.86 (ddd, J=10.8 Hz, 9.2 Hz, 6.4 Hz, 1H), 2.66 (ddd, J=8 Hz, 5.6 Hz, 2.8 Hz, 1H), 2.16-2.06 (m, 2H), 1.91 (dd, J=12.8 Hz, 5.6 Hz, 1H), 0.95 (s, 9H), 0.12 (ds, 6H) ppm. ¹³C NMR (CDCl₃, 100 MHz) δ: 148.4, 139.2, 134.5, 129.3, 128.3, 128.3, 127.2, 123.5, 119.0, 109.0, 92.3, 80.0, 72.3, 65.5, 59.2, 57.8, 49.6, 44.2, 39.2, 26.1, 18.5, −4.9, −5.1 ppm. $R_f$=0.79 (7:3 hexanes/EtOAc).

anti-pentacycle: ¹H NMR (CDCl₃, 400 MHz) δ: 7.45 (d, J=7.2 Hz, 2H), 7.37 (t, J=7.6 Hz, 2H), 7.32-7.27 (m, 1H), 7.02-7.09 (m, 2H), 6.74 (td, J=7.6 Hz, 0.8 Hz, 1H), 6.58 (d, J=7.6 Hz, 1H), 5.03 (s, 1H), 4.58 (s, 1H), 4.09 (d, J=12.8 Hz, 1H), 3.65 (d, J=13.2 Hz, 1H), 3.52-3.47 (m, 2H), 3.42 (dd, J=11.2 Hz, 4.8 Hz, 1H), 3.12 (ddd, J=10 Hz, 6.8 Hz, 3.6 Hz, 1H), 2.70 (td, J=9.2 Hz, 6.8 Hz, 1H), 2.62 (d, J=3.2 Hz, 1H), 2.17 (ddd, J=12.8 Hz, 8.8 Hz, 7 Hz, 1H), 2.01 (ddd, J=12.4 Hz, 7 Hz, 3.8 Hz), 1.66 (td, J=5.6 Hz, 3.2 Hz, 1H), 0.88 (s, 9H), 0 (ds, 6H) ppm. ¹³C NMR (CDCl₃, 100 MHz) δ: 149.8, 139.1, 134.5, 129.1, 128.6, 128.6, 127.4, 123.2, 119.2, 108.7, 90.2, 78.3, 67.4, 65.4, 59.3, 55.5, 51.2, 41.5, 37.6, 26.2, 18.5, 18.5, −14.9, −5.0 ppm. HRMS (ESI) [M+H]⁺ calcd. For $C_{27}H_{38}N_3OSi$ 448.2778 found 448.2788. $R_f$=0.15 (7:3 hexanes/EtOAc).

2-Aziridin-2-yl-3-oxa-1-azabicyclo[3.1.0]hexan-4-ol (2d)

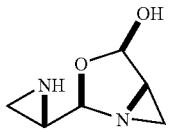

To a flame dried Schlenk tube equipped with a magnetic stirring bar, a rubber septum and a $N_2$ inlet was added aziridine-2-carboxylic acid methyl ester 1d (1.01 g, 10 mmol) dissolved into 25 ml of anhydrous toluene. The reaction flask was cooled to −78° C., at which point 13 ml of a 1.5M solution of DIBAL in toluene was added slowly via syringe to the reaction mixture over a period of 30 minutes. The reaction was allowed to stir for 5 hours or until completed by TLC. MeOH was added via syringe to the reaction mixture over a period of 15 minutes while maintaining a temperature of −78° C. After the addition of MeOH, the reaction mixture was allowed to warm to room temperature and stir for 30 minutes. A few drops of saturated aqueous $Na_2SO_4$ were used to cause precipitation of aluminum salts, which were filtered off after stirring for another 30 minutes. The filtrate was concentrated under reduced pressure to yield a thick clear oil, which was pure enough by NMR to use in subsequent transformations. An analytically pure sample can be obtained by subjecting the crude product to flash column chromatography (silica gel; 20% water in MeCN, $R_f$=0.32) to yield the title compound as a colourless oil in 76% yield. The compound is water soluble. ¹H NMR (CDCl₃ with D₂O present, 400 MHz) δ: 5.33 (s, 0.5H), 5.27 (s, 1H), 4.92 (s, 1H), 4.91 (s, 0.5H), 2.62 (dd, J=5.2 Hz, 3.2 Hz, 1H), 2.53 (dd, J=5.6 Hz, 3.6 Hz, 0.5H), 2.47-2.43 (m, 1H), 2.39 (quintet, J=3.2 Hz, 0.5H), 2.29 (d, J=3.6 Hz, 0.5H), 2.10 (d, J=6.4 Hz, 0.5H), 1.86 (d, J=6.4 Hz, 1H), 1.76 (d, J=5.2 Hz, 1H), 1.70 (dd, J=5.2 Hz, 3.6 Hz, 1.5H), 1.26 (d, J=3.2 Hz, 1H), 1.21 (d, J=3.2 Hz, 0.5H) ppm. $^{13}$C NMR (CDCl$_3$, 100 MHz) δ: 96.6 (major), 95.7 (minor), 95.6 (minor), 94.8 (major), 44.8 (minor), 44.0 (major), 31.9 (minor), 31.6 (major), 28.0 (major), 27.6 (minor), 21.3 ppm.

Pentacycle Formation from 2d (Table 2, Entry 3)

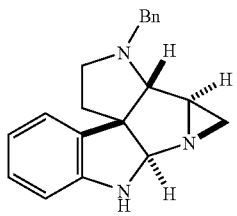

In a name dried flask equipped with a rubber septum attached to a N$_2$ source and a magnetic stirring bar was added N-benzyl tryptamine (325 mg, 1.3 mmol) dissolved into 2 ml of trifluoroethanol. The reaction mixture was cooled to 0° C. and 2d (92 mg, 0.65 mmol) dissolved in 2 ml of trifluoroethanol was added to the reaction. The resulting mixture was stirred for 3 hours, at which point TLC analysis exhibited consumption of the amino aldehyde. The reaction mixture was concentrated under reduced pressure and subjected to flash column chromatography (silica gel; 5% MeOH in CH$_2$Cl$_2$, R$_f$=0.18 and 0.16) to afford a 1.6:1 (syn/trans) mixture of diastereoisomers as a pale orange solid in 74% yield. Mp=51-53° C. $^1$H NMR (CDCl$_3$, 400 MHz) δ: 7.42-7.22 (m, 8H), 7.15 (d, 7.6 H, 1.6H), 7.64 (td, J=7.6 Hz, 1.2 Hz, 1.6H), 7.32 (td, J=7.6 Hz, 1.2 Hz, 1H), 7.09 (d, J=7.6 Hz, 1H), 6.76 (td, J=7.2 Hz, 0.8 Hz, 1.6H), 6.70 (td, J=7.2 Hz, 0.8 Hz, 1H), 6.59 (d, J=7.6 Hz, 1.6 H), 6.57 (d, J=7.6 Hz, 1H), 5.20 (d, J=1.2 Hz, 1.6H), 4.54 (s, 1.6H), 4.46 (s, 2.6 H), 4.05 (d, J=12.4 Hz, 1H), 3.80-3.60 (m, 4.6H), 3.49 (d, J=10.8 HZ, 1.6H), 3.46 (s, 1H), 3.26 (t, J=7.8 Hz, 1.6H), 3.11 (ddd, J=11.2 Hz, 6.8 Hz, 3.7 Hz, 1H), 3.00 (s, 1H), 2.87 (ddd, J=11.2 Hz, 9.6 Hz, 7.2 Hz, 1.6H), 2.70-2.62 (m, 1.6 H), 2.22-2.16 (m, 3.2H), 2.16-2.04 (m, 2.6H), 1.98 (ddd, J=13.2 Hz, 11.2 Hz, 7.6 Hz, 1H), 1.93 (ddd, J=12.3 Hz, 7.6 Hz, 4 Hz, 1.6H), 1.86 (d, J=6.8 Hz, 1.6H), 1.50 (dd, J=7.4 Hz, 1.2 Hz, 1H), 1.17 (d, J=5.4 Hz, 1H) ppm. $^{13}$C NMR (CDCl$_3$, 100 MHz) δ: 150.0, 148.3, 138.9, 134.7, 134.7, 129.0, 129.0, 128.4, 128.2, 128.2, 128.2, 127.2, 123.5, 122.8, 118.9, 108.8 (syn), 108.3 (anti), 92.2 (syn), 90.0 (anti), 80.1 (syn), 78.2 (anti), 71.5 (syn), 60.6 (anti), 50.4 (syn), 59.2 (anti), 58.0 (syn), 55.4 (anti), 46.5 (syn), 45.2 (anti), 41.4 (syn), 39.4 (anti), 32.0 (syn), 25.3 (anti) ppm. HRMS (ESI) [M+H]$^+$ calcd. For C$_{20}$H$_{21}$N$_3$ 304.1814, found 304.1818.

X-Ray Crystallographic Information

6-Phenyl-2-(3-phenylaziridin-2-yl)-3-oxa-1-azabicyclo[3.1.0]hexan-4-ol (2a)

TABLE 4

Crystal data and structure refinement for 6-Phenyl-2-(3-phenylaziridin-2-yl)-3-oxa-1-azabicyclo[3.1.0]hexan-4-ol.

| | |
|---|---|
| Empirical formula | C18H18N2O2 |
| Formula weight | 294.34 |
| Temperature | 150(1) K |
| Wavelength | 0.71073 Å |
| Crystal system | Monoclinic |

TABLE 4-continued

Crystal data and structure refinement for 6-Phenyl-2-(3-phenylaziridin-2-yl)-3-oxa-1-azabicyclo[3.1.0]hexan-4-ol.

| | |
|---|---|
| Space group | C 2 |
| Unit cell dimensions | a = 15.8979(14) Å  a = 90°. |
| | b = 5.7353(7) Å  b = 90.979(6)°. |
| | c = 15.8160(15) Å  g = 90°. |
| Volume | 1441.9(3) Å$^3$ |
| Z | 4 |
| Density (calculated) | 1.356 Mg/m$^3$ |
| Absorption coefficient | 0.089 mm$^{-1}$ |
| F(000) | 624 |
| Crystal size | 0.26 × 0.18 × 0.06 mm$^3$ |
| Theta range for data collection | 2.56 to 27.53°. |
| Index ranges | −20 <= h <= 20, −7 <= k <= 6, |
| | −17 <= l <= 20 |
| Reflections collected | 5337 |
| Independent reflections | 1809 [R(int) = 0.0755] |
| Completeness to theta = 27.53° | 99.8% |
| Absorption correction | Semi-empirical from equivalents |
| Max. and min. transmission | 1.010 and 0.796 |
| Refinement method | Full-matrix least-squares on F$^2$ |
| Data/restraints/parameters | 1809/1/208 |
| Goodness-of-fit on F$^2$ | 1.043 |
| Final R indices [I > 2sigma(I)] | R1 = 0.0465, wR2 = 0.0979 |
| R indices (all data) | R1 = 0.0848, wR2 = 0.1156 |
| Extinction coefficient | 0.020(3) |
| Largest diff. peak and hole | 0.201 and −0.185 e · Å$^{-3}$ |

TABLE 5

Atomic coordinates (×10$^4$) and equivalent isotropic displacement parameters (Å$^2$ × 10$^3$) for 6-Phenyl-2-(3-phenylaziridin-2-yl)-3-oxa-1-azabicyclo[3.1.0]hexan-4-ol. U(eq) is defined as one third of the trace of the orthogonalized U$^{ij}$ tensor.

| | x | y | z | U(eq) |
|---|---|---|---|---|
| O(1) | 8403(1) | 6659(4) | 2416(1) | 37(1) |
| O(2) | 9847(2) | 7505(5) | 2536(1) | 44(1) |
| N(1) | 8688(2) | 3502(5) | 1511(2) | 35(1) |
| N(2) | 9477(2) | 3334(7) | 3299(2) | 45(1) |
| C(1) | 8471(2) | 5035(6) | 776(2) | 33(1) |
| C(2) | 9241(2) | 5499(6) | 1306(2) | 36(1) |
| C(3) | 9146(2) | 7339(6) | 1982(2) | 36(1) |
| C(4) | 8274(2) | 4200(6) | 2284(2) | 36(1) |
| C(5) | 8622(2) | 2725(7) | 2996(2) | 37(1) |
| C(6) | 8751(2) | 3602(7) | 3867(2) | 35(1) |
| C(7) | 8664(2) | 2085(6) | 4625(2) | 34(1) |
| C(8) | 9003(2) | −133(6) | 4671(2) | 38(1) |
| C(9) | 8949(2) | −1445(7) | 5405(2) | 40(1) |
| C(10) | 8532(2) | −570(7) | 6094(2) | 40(1) |
| C(11) | 8163(2) | 1598(7) | 6054(2) | 41(1) |
| C(12) | 8225(2) | 2935(6) | 5321(2) | 37(1) |
| C(13) | 8542(2) | 3936(6) | −76(2) | 34(1) |
| C(14) | 8934(2) | 1794(6) | −189(2) | 37(1) |
| C(15) | 9054(2) | 902(6) | −991(2) | 41(1) |
| C(16) | 8780(2) | 2136(7) | −1693(2) | 41(1) |
| C(17) | 8365(2) | 4222(7) | −1587(2) | 44(1) |
| C(18) | 8246(2) | 5139(6) | −787(2) | 38(1) |

TABLE 6

Bond lengths [Å] and angles [°] for 6-Phenyl-2-(3-phenylaziridin-2-yl)-3-oxa-1-azabicyclo[3.1.0]hexan-4-ol.

| | |
|---|---|
| O(1)—C(3) | 1.429(4) |
| O(1)—C(4) | 1.440(4) |
| O(2)—C(3) | 1.410(4) |
| N(1)—C(4) | 1.455(4) |
| N(1)—C(2) | 1.483(4) |
| N(1)—C(1) | 1.493(4) |
| N(2)—C(5) | 1.476(4) |
| N(2)—C(6) | 1.483(4) |
| C(1)—C(13) | 1.493(4) |

TABLE 6-continued

Bond lengths [Å] and angles [°] for 6-Phenyl-2-(3-phenylaziridin-2-yl)-3-oxa-1-azabicyclo[3.1.0]hexan-4-ol.

| | |
|---|---|
| C(1)—C(2) | 1.496(4) |
| C(2)—C(3) | 1.512(5) |
| C(4)—C(5) | 1.507(4) |
| C(5)—C(6) | 1.477(4) |
| C(6)—C(7) | 1.490(4) |
| C(7)—C(8) | 1.383(5) |
| C(7)—C(12) | 1.401(4) |
| C(8)—C(9) | 1.388(4) |
| C(9)—C(10) | 1.378(5) |
| C(10)—C(11) | 1.376(5) |
| C(11)—C(12) | 1.395(5) |
| C(13)—C(14) | 1.391(5) |
| C(13)—C(18) | 1.394(5) |
| C(14)—C(15) | 1.384(4) |
| C(15)—C(16) | 1.381(5) |
| C(16)—C(17) | 1.378(5) |
| C(17)—C(18) | 1.386(4) |
| C(3)—O(1)—C(4) | 108.4(2) |
| C(4)—N(1)—C(2) | 104.5(3) |
| C(4)—N(1)—C(1) | 113.0(3) |
| C(2)—N(1)—C(1) | 60.3(2) |
| C(5)—N(2)—C(6) | 59.91(19) |
| C(13)—C(1)—N(1) | 115.7(3) |
| C(13)—C(1)—C(2) | 120.5(3) |
| N(1)—C(1)—C(2) | 59.5(2) |
| N(1)—C(2)—C(1) | 60.2(2) |
| N(1)—C(2)—C(3) | 108.5(2) |
| C(1)—C(2)—C(3) | 115.4(3) |
| O(2)—C(3)—O(1) | 111.8(2) |
| O(2)—C(3)—C(2) | 113.5(3) |
| O(1)—C(3)—C(2) | 104.0(3) |
| O(1)—C(4)—N(1) | 109.0(3) |
| O(1)—C(4)—C(5) | 113.0(3) |
| N(1)—C(4)—C(5) | 107.9(3) |
| N(2)—C(5)—C(6) | 60.3(2) |
| N(2)—C(5)—C(4) | 115.8(3) |
| C(6)—C(5)—C(4) | 123.3(3) |
| C(5)—C(6)—N(2) | 59.8(2) |
| C(5)—C(6)—C(7) | 122.6(3) |
| N(2)—C(6)—C(7) | 120.7(3) |
| C(8)—C(7)—C(12) | 118.5(3) |
| C(8)—C(7)—C(6) | 122.6(3) |
| C(12)—C(7)—C(6) | 118.9(3) |
| C(7)—C(8)—C(9) | 120.9(3) |
| C(10)—C(9)—C(8) | 120.1(3) |
| C(11)—C(10)—C(9) | 120.2(3) |
| C(10)—C(11)—C(12) | 119.9(3) |
| C(11)—C(12)—C(7) | 120.4(3) |
| C(14)—C(13)—C(18) | 118.6(3) |
| C(14)—C(13)—C(1) | 122.0(3) |
| C(18)—C(13)—C(1) | 119.3(3) |
| C(15)—C(14)—C(13) | 120.9(3) |
| C(16)—C(15)—C(14) | 120.1(3) |
| C(17)—C(16)—C(15) | 119.5(3) |
| C(16)—C(17)—C(18) | 120.9(4) |
| C(17)—C(18)—C(13) | 120.0(3) |

TABLE 7

Anisotropic displacement parameters (Å² × 10³) for 6-Phenyl-2-(3-phenylaziridin-2-yl)-3-oxa-1-azabicyclo[3.1.0]hexan-4-ol. The anisotropic displacement factor exponent takes the form: $-2p^2[h^2 a^{*2}U^{11} + \ldots + 2 h k a^* b^* U^{12}]$

| | $U^{11}$ | $U^{22}$ | $U^{33}$ | $U^{23}$ | $U^{13}$ | $U^{12}$ |
|---|---|---|---|---|---|---|
| O(1) | 44(1) | 33(1) | 32(1) | −1(1) | 5(1) | 2(1) |
| O(2) | 50(1) | 44(2) | 39(1) | −1(1) | −4(1) | −8(1) |
| N(1) | 41(2) | 35(2) | 30(1) | 2(1) | 2(1) | −3(1) |
| N(2) | 39(2) | 54(2) | 43(2) | 9(2) | 6(1) | 7(2) |
| C(1) | 36(2) | 34(2) | 29(2) | 1(2) | 0(1) | 2(2) |
| C(2) | 41(2) | 35(2) | 32(2) | −3(2) | 0(1) | 1(2) |
| C(3) | 38(2) | 39(2) | 31(2) | −1(2) | −2(1) | 0(2) |
| C(4) | 45(2) | 35(2) | 28(2) | −2(2) | 1(2) | 2(2) |
| C(5) | 45(2) | 35(2) | 33(2) | −1(2) | 5(2) | 0(2) |
| C(6) | 39(2) | 34(2) | 32(2) | −2(2) | 1(1) | 1(2) |
| C(7) | 34(2) | 36(2) | 30(2) | 0(2) | −3(1) | −2(2) |
| C(8) | 40(2) | 37(2) | 36(2) | −2(2) | −1(2) | −2(2) |
| C(9) | 41(2) | 38(2) | 42(2) | 5(2) | −2(2) | −2(2) |
| C(10) | 48(2) | 42(2) | 30(2) | 3(2) | −3(2) | −7(2) |
| C(11) | 44(2) | 45(2) | 34(2) | −3(2) | −1(2) | −2(2) |
| C(12) | 33(2) | 39(2) | 38(2) | 2(2) | −4(1) | −1(2) |
| C(13) | 34(2) | 41(2) | 28(2) | 1(2) | 0(1) | −4(2) |
| C(14) | 41(2) | 34(2) | 37(2) | 1(2) | 1(2) | 3(2) |
| C(15) | 43(2) | 42(2) | 38(2) | −4(2) | 1(2) | −1(2) |
| C(16) | 43(2) | 47(2) | 32(2) | −7(2) | −1(2) | −6(2) |
| C(17) | 50(2) | 49(2) | 31(2) | 3(2) | −6(2) | −3(2) |
| C(18) | 42(2) | 36(2) | 35(2) | 1(2) | −2(1) | −1(2) |

TABLE 8

Hydrogen coordinates (×10⁴) and isotropic displacement parameters (Å² × 10³) for 6-Phenyl-2-(3-phenylaziridin-2-yl)-3-oxa-1-azabicyclo[3.1.0]hexan-4-ol.

| | x | y | z | U(eq) |
|---|---|---|---|---|
| H(2O) | 9760(30) | 5840(110) | 2780(30) | 92(17) |
| H(2N) | 9750(30) | 2000(90) | 3370(20) | 65(14) |
| H(1A) | 7988 | 6129 | 852 | 40 |
| H(2A) | 9809 | 5198 | 1066 | 43 |
| H(3A) | 9047 | 8886 | 1706 | 43 |
| H(4A) | 7657 | 3895 | 2220 | 43 |
| H(5A) | 8504 | 1017 | 2948 | 45 |
| H(6A) | 8567 | 5251 | 3952 | 42 |
| H(8A) | 9277 | −767 | 4194 | 45 |
| H(9A) | 9200 | −2947 | 5434 | 48 |
| H(10A) | 8500 | −1468 | 6597 | 48 |
| H(11A) | 7867 | 2184 | 6526 | 49 |
| H(12A) | 7969 | 4430 | 5294 | 44 |
| H(14A) | 9122 | 931 | 291 | 45 |
| H(15A) | 9325 | −560 | −1059 | 49 |
| H(16A) | 8876 | 1550 | −2245 | 49 |
| H(17A) | 8158 | 5044 | −2069 | 52 |
| H(18B) | 7963 | 6586 | −723 | 45 |

TABLE 9

Hydrogen bonds for 6-Phenyl-2-(3-phenylaziridin-2-yl)-3-oxa-1-azabicyclo[3.1.0]hexan-4-ol [Å and °].

| D−H...A | d(D−H) | d(H...A) | d(D...A) | <(DHA) |
|---|---|---|---|---|
| O(2)—H(2O)...N(2) | 1.04(6) | 1.72(6) | 2.748(4) | 169(4) |

TABLE 10

Crystal data and structure refinement for 5b.

| | | |
|---|---|---|
| Empirical formula | C26H25N3 | |
| Formula weight | 379.49 | |
| Temperature | 150(2) K | |
| Wavelength | 0.71073 Å | |
| Crystal system | Triclinic | |
| Space group | P-1 | |
| Unit cell dimensions | a = 7.9853(9) Å | a = 90.291(6)°. |
| | b = 10.9831(14) Å | b = 98.770(6)°. |
| | c = 12.1590(13) Å | g = 102.687(6)°. |

TABLE 10-continued

Crystal data and structure refinement for 5b.

| | |
|---|---|
| Volume | 1027.4(2) Å$^3$ |
| Z | 2 |
| Density (calculated) | 1.227 Mg/m$^3$ |
| Absorption coefficient | 0.073 mm$^{-1}$ |
| F(000) | 404 |
| Crystal size | 0.35 × 0.15 × 0.14 mm$^3$ |
| Theta range for data collection | 2.60 to 25.14°. |
| Index ranges | −9 <= h <= 9, −13 <= k <= 13, −14 <= l <= 14 |
| Reflections collected | 7211 |
| Independent reflections | 3611 [R(int) = 0.0874] |
| Completeness to theta = 25.14° | 98.1% |
| Absorption correction | None |
| Refinement method | Full-matrix least-squares on F$^2$ |
| Data/restraints/parameters | 3611/0/267 |
| Goodness-of-fit on F$^2$ | 1.002 |
| Final R indices [I > 2sigma(I)] | R1 = 0.0614, wR2 = 0.1483 |
| R indices (all data) | R1 = 0.1085, wR2 = 0.1780 |
| Extinction coefficient | 0.054(8) |
| Largest diff. peak and hole | 0.243 and −0.296 e · Å$^{-3}$ |

TABLE 11

Atomic coordinates (×10$^4$) and equivalent isotropic displacement parameters (Å$^2$ × 10$^3$) for 5b. U(eq) is defined as one third of the trace of the orthogonalized U$^{ij}$ tensor.

| | x | y | z | U(eq) |
|---|---|---|---|---|
| N(1) | 5517(3) | 3528(2) | 4575(2) | 39(1) |
| N(2) | 508(3) | 2539(2) | 1985(2) | 32(1) |
| N(3) | 2589(3) | 3907(2) | 4478(2) | 33(1) |
| C(1) | 3373(3) | 2659(2) | 2997(2) | 32(1) |
| C(2) | 4519(3) | 1777(2) | 3414(2) | 32(1) |
| C(3) | 4486(3) | 578(2) | 3054(2) | 35(1) |
| C(4) | 5723(3) | −37(2) | 3571(2) | 36(1) |
| C(5) | 6968(3) | 558(2) | 4446(2) | 37(1) |
| C(6) | 7003(3) | 1752(2) | 4828(2) | 35(1) |
| C(7) | 5774(3) | 2357(2) | 4301(2) | 31(1) |
| C(8) | 4033(3) | 3790(2) | 3856(2) | 35(1) |
| C(9) | 1054(3) | 2908(2) | 4018(2) | 31(1) |
| C(10) | 1403(3) | 2200(2) | 3044(2) | 31(1) |
| C(11) | 1613(3) | 2390(3) | 1163(2) | 38(1) |
| C(12) | 3422(3) | 2987(3) | 1756(2) | 41(1) |
| C(13) | 2046(3) | 2790(2) | 5131(2) | 32(1) |
| C(14) | 1299(3) | 2961(2) | 6164(2) | 32(1) |
| C(15) | 648(3) | 4006(3) | 6343(2) | 37(1) |
| C(16) | −233(4) | 4078(3) | 7231(2) | 40(1) |
| C(17) | −457(4) | 3114(3) | 7958(2) | 44(1) |
| C(18) | 216(4) | 2076(3) | 7801(2) | 43(1) |
| C(19) | 1074(3) | 1997(2) | 6901(2) | 36(1) |
| C(20) | −1284(3) | 1814(2) | 1712(2) | 37(1) |
| C(21) | −2353(3) | 2313(2) | 770(2) | 33(1) |
| C(22) | −2288(4) | 3582(3) | 705(2) | 40(1) |
| C(23) | −3385(4) | 4031(3) | −109(2) | 43(1) |
| C(24) | −4570(4) | 3216(3) | −875(2) | 47(1) |
| C(25) | −4637(4) | 1955(3) | −826(2) | 48(1) |
| C(26) | −3521(4) | 1507(3) | −19(2) | 41(1) |

TABLE 12

Bond lengths [Å] and angles [°] for 5b.

| | |
|---|---|
| N(1)—C(7) | 1.392(3) |
| N(1)—C(8) | 1.445(3) |
| N(2)—C(11) | 1.462(3) |
| N(2)—C(20) | 1.464(3) |
| N(2)—C(10) | 1.465(3) |
| N(3)—C(13) | 1.485(3) |
| N(3)—C(9) | 1.487(3) |
| N(3)—C(8) | 1.499(3) |
| C(1)—C(2) | 1.512(3) |
| C(1)—C(10) | 1.553(3) |
| C(1)—C(12) | 1.558(4) |
| C(1)—C(8) | 1.563(4) |
| C(2)—C(3) | 1.379(4) |
| C(2)—C(7) | 1.399(4) |
| C(3)—C(4) | 1.391(4) |
| C(4)—C(5) | 1.390(4) |
| C(5)—C(6) | 1.382(4) |
| C(6)—C(7) | 1.384(4) |
| C(9)—C(13) | 1.481(3) |
| C(9)—C(10) | 1.508(4) |
| C(11)—C(12) | 1.516(4) |
| C(13)—C(14) | 1.498(4) |
| C(14)—C(15) | 1.389(4) |
| C(14)—C(19) | 1.390(4) |
| C(15)—C(16) | 1.386(4) |
| C(16)—C(17) | 1.381(4) |
| C(17)—C(18) | 1.387(4) |
| C(18)—C(19) | 1.388(4) |
| C(20)—C(21) | 1.502(4) |
| C(21)—C(22) | 1.387(4) |
| C(21)—C(26) | 1.389(4) |
| C(22)—C(23) | 1.385(4) |
| C(23)—C(24) | 1.384(4) |
| C(24)—C(25) | 1.376(4) |
| C(25)—C(26) | 1.389(4) |
| C(7)—N(1)—C(8) | 110.6(2) |
| C(11)—N(2)—C(20) | 114.2(2) |
| C(11)—N(2)—C(10) | 105.25(19) |
| C(20)—N(2)—C(10) | 112.59(19) |
| C(13)—N(3)—C(9) | 59.81(15) |
| C(13)—N(3)—C(8) | 112.12(19) |
| C(9)—N(3)—C(8) | 107.1(2) |
| C(2)—C(1)—C(10) | 116.3(2) |
| C(2)—C(1)—C(12) | 113.6(2) |
| C(10)—C(1)—C(12) | 103.5(2) |
| C(2)—C(1)—C(8) | 102.6(2) |
| C(10)—C(1)—C(8) | 105.8(2) |
| C(12)—C(1)—C(8) | 115.2(2) |
| C(3)—C(2)—C(7) | 120.0(2) |
| C(3)—C(2)—C(1) | 130.5(2) |
| C(7)—C(2)—C(1) | 109.5(2) |
| C(2)—C(3)—C(4) | 119.4(2) |
| C(5)—C(4)—C(3) | 119.8(2) |
| C(6)—C(5)—C(4) | 121.5(2) |
| C(5)—C(6)—C(7) | 118.1(3) |
| C(6)—C(7)—N(1) | 127.9(3) |
| C(6)—C(7)—C(2) | 121.2(2) |
| N(1)—C(7)—C(2) | 110.9(2) |
| N(1)—C(8)—N(3) | 112.5(2) |
| N(1)—C(8)—C(1) | 106.1(2) |
| N(3)—C(8)—C(1) | 108.9(2) |
| C(13)—C(9)—N(3) | 60.02(16) |
| C(13)—C(9)—C(10) | 118.0(2) |
| N(3)—C(9)—C(10) | 111.6(2) |
| N(2)—C(10)—C(9) | 111.7(2) |
| N(2)—C(10)—C(1) | 105.49(19) |
| C(9)—C(10)—C(1) | 105.9(2) |
| N(2)—C(11)—C(12) | 103.0(2) |
| C(11)—C(12)—C(1) | 104.3(2) |
| C(9)—C(13)—N(3) | 60.17(16) |
| C(9)—C(13)—C(14) | 120.4(2) |
| N(3)—C(13)—C(14) | 118.0(2) |
| C(15)—C(14)—C(19) | 118.8(2) |
| C(15)—C(14)—C(13) | 121.4(2) |
| C(19)—C(14)—C(13) | 119.5(2) |
| C(16)—C(15)—C(14) | 120.6(3) |
| C(17)—C(16)—C(15) | 120.3(3) |
| C(16)—C(17)—C(18) | 119.7(3) |
| C(17)—C(18)—C(19) | 120.0(3) |
| C(18)—C(19)—C(14) | 120.6(2) |
| N(2)—C(20)—C(21) | 113.9(2) |
| C(22)—C(21)—C(26) | 118.2(3) |
| C(22)—C(21)—C(20) | 121.0(2) |
| C(26)—C(21)—C(20) | 120.7(2) |
| C(23)—C(22)—C(21) | 120.9(3) |
| C(24)—C(23)—C(22) | 120.4(3) |
| C(25)—C(24)—C(23) | 119.3(3) |

TABLE 12-continued

Bond lengths [Å] and angles [°] for 5b.

| | |
|---|---|
| C(24)—C(25)—C(26) | 120.3(3) |
| C(25)—C(26)—C(21) | 120.9(3) |

Symmetry Transformations Used to Generate Equivalent Atoms:

TABLE 13

Anisotropic displacement parameters (Å$^2$ × 10$^3$) for 5b.
The anisotropic displacement factor exponent takes the form:
$-2p^2[h^2 a^{*2} U^{11} + \ldots + 2 h k a^* b^* U^{12}]$

| | U$^{11}$ | U$^{22}$ | U$^{33}$ | U$^{23}$ | U$^{13}$ | U$^{12}$ |
|---|---|---|---|---|---|---|
| N(1) | 33(1) | 29(1) | 53(2) | −4(1) | 5(1) | 2(1) |
| N(2) | 32(1) | 33(1) | 29(1) | 3(1) | 7(1) | 3(1) |
| N(3) | 31(1) | 26(1) | 40(1) | 4(1) | 11(1) | 1(1) |
| C(1) | 32(1) | 29(2) | 36(2) | 5(1) | 10(1) | 4(1) |
| C(2) | 29(1) | 29(2) | 37(2) | 2(1) | 9(1) | 3(1) |
| C(3) | 35(2) | 33(2) | 35(2) | −2(1) | 8(1) | 4(1) |
| C(4) | 38(2) | 30(2) | 43(2) | 1(1) | 12(1) | 8(1) |
| C(5) | 32(2) | 38(2) | 43(2) | 6(1) | 10(1) | 8(1) |
| C(6) | 30(1) | 35(2) | 37(2) | 3(1) | 7(1) | 3(1) |
| C(7) | 31(1) | 26(1) | 37(2) | 4(1) | 12(1) | 2(1) |
| C(8) | 34(2) | 27(2) | 44(2) | 5(1) | 11(1) | 6(1) |
| C(9) | 34(1) | 25(1) | 33(2) | 1(1) | 8(1) | 2(1) |
| C(10) | 32(1) | 29(1) | 31(2) | 5(1) | 5(1) | 2(1) |
| C(11) | 40(2) | 39(2) | 36(2) | 5(1) | 13(1) | 7(1) |
| C(12) | 35(2) | 48(2) | 41(2) | 10(1) | 13(1) | 9(1) |
| C(13) | 32(1) | 27(1) | 35(2) | 3(1) | 7(1) | 3(1) |
| C(14) | 29(1) | 28(2) | 34(2) | −4(1) | 3(1) | 1(1) |
| C(15) | 42(2) | 30(2) | 37(2) | −2(1) | 6(1) | 5(1) |
| C(16) | 43(2) | 37(2) | 41(2) | −6(1) | 6(1) | 11(1) |
| C(17) | 47(2) | 46(2) | 40(2) | −4(1) | 12(1) | 7(1) |
| C(18) | 49(2) | 46(2) | 36(2) | 6(1) | 12(1) | 11(1) |
| C(19) | 37(2) | 34(2) | 38(2) | 4(1) | 8(1) | 9(1) |
| C(20) | 34(2) | 33(2) | 39(2) | 1(1) | 5(1) | 1(1) |
| C(21) | 31(1) | 36(2) | 31(2) | 1(1) | 9(1) | 4(1) |
| C(22) | 41(2) | 35(2) | 41(2) | −1(1) | 8(1) | 3(1) |
| C(23) | 44(2) | 43(2) | 43(2) | 9(1) | 7(1) | 11(1) |
| C(24) | 45(2) | 61(2) | 36(2) | 9(2) | 6(1) | 15(2) |
| C(25) | 41(2) | 55(2) | 41(2) | −2(1) | −1(1) | 1(2) |
| C(26) | 43(2) | 35(2) | 42(2) | −1(1) | 3(1) | 2(1) |

TABLE 14

Hydrogen coordinates (×10$^4$) and isotropic
displacement parameters (Å$^2$ × 10$^3$) for 5b.

| | x | y | z | U(eq) |
|---|---|---|---|---|
| H(3A) | 3626 | 175 | 2459 | 42 |
| H(4A) | 5716 | −861 | 3327 | 44 |
| H(5A) | 7815 | 134 | 4789 | 45 |
| H(6A) | 7847 | 2146 | 5434 | 42 |
| H(8A) | 4399 | 4574 | 3456 | 42 |
| H(9A) | −126 | 3091 | 3983 | 37 |
| H(10A) | 1091 | 1278 | 3139 | 38 |
| H(11A) | 1312 | 2826 | 475 | 46 |
| H(11B) | 1511 | 1497 | 971 | 46 |
| H(12A) | 3683 | 3903 | 1675 | 49 |
| H(12B) | 4311 | 2638 | 1456 | 49 |
| H(13A) | 2801 | 2170 | 5170 | 38 |
| H(15A) | 808 | 4678 | 5853 | 44 |
| H(16A) | −684 | 4793 | 7341 | 48 |
| H(17A) | −1070 | 3162 | 8562 | 53 |
| H(18A) | 91 | 1420 | 8308 | 51 |
| H(19A) | 1512 | 1276 | 6788 | 43 |
| H(20A) | −1854 | 1799 | 2382 | 44 |
| H(20B) | −1264 | 942 | 1515 | 4 |
| H(22A) | −1481 | 4152 | 1226 | 48 |
| H(23A) | −3324 | 4903 | −141 | 52 |
| H(24A) | −5328 | 3523 | −1429 | 57 |
| H(25A) | −5450 | 1389 | −1346 | 57 |

TABLE 14-continued

Hydrogen coordinates (×10$^4$) and isotropic
displacement parameters (Å$^2$ × 10$^3$) for 5b.

| | x | y | z | U(eq) |
|---|---|---|---|---|
| H(26A) | −3557 | 637 | −7 | 50 |
| H(1N) | 6410(40) | 4100(30) | 4860(20) | 52(9) |

TABLE 15

Hydrogen bonds for 5b [Å and °].

| D-H...A | d(D-H) | d(H...A) | d(D...A) | <(DHA) |
|---|---|---|---|---|
| N(1)—H(1N)...N(3)#1 | 0.87(3) | 2.25(3) | 3.020(3) | 147(3) |

Symmetry transformations used to generate equivalent atoms:
1 −x+1, −y+1, −z+1

Representative Synthesis of Siderophore Derivatives

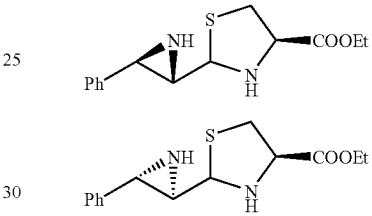

In a vial equipped with a rubber septum and a nitrogen line was dissolved aziridine aldehyde 2a (29.4 mg, 0.1 mmol) in 250 ul of TFE under an atmosphere of nitrogen. The solution was cooled to 0° C. and then (L)-cysteine ethyl ester free-base (29.8 mg, 0.2 mmol) dissolved in 250 ul of TFE was added via syringe. The reaction was allowed to warm to room temperature over 1 hour and then stirred at room temperature for another 8 hours and then concentrated under reduced pressure. The crude product was then subjected to flash column chromatography (eluent: 50% EtOAc in hexanes to 100% EtOAc) to afford the two diastereomers as a 1:1 mixture in 84% yield.

1 ($R_f$=0.45, EtOAC) $^1$H NMR (200 MHz,CDCl$_3$) δ: 7.50-7.20 (m, 5H), 4.87 (bs, 1H), 4.31 (q, J=7 Hz, 2H), 3.92 (dd, J=6.2 Hz, 9.2 Hz, 1H), 3.82 (dd, J=6.6 Hz, 10.2 Hz, 1H), 2.97 (d, J=2.8 Hz, 1H), 2.89 (t, J=9.8 Hz, 1H), 2.62 (t, J=3 Hz, 1H), 1.37 (t, J=7 Hz, 3H) ppm. $^{13}$C NMR (200 MHz, CDCl$_3$) δ: 170.5, 138.8, 128.4, 127.3, 125.7, 72.1, 65.6, 61.6, 42.1, 37.5, 14.0 ppm.

2 ($R_f$=0.3, EtOAc) $^1$H NMR (200 MHz,CDCl$_3$) δ: 7.41-7.18 (m, 5H), 5.06 (bs, 1H), 4.25 (q, J=7.4 Hz, 2H), 4.10 (t, J=6.2 Hz, 1H), 3.32 (dd, J=6.2 Hz, 10.2 Hz, 1H), 2.97 (dd, J=7.4 Hz, 10.6 Hz, 1H), 2.77 (m, 1H), 2.37 (d, J=3.4 Hz, 1H), 1.31 (t, J=7.4 Hz, 3H) ppm. $^{13}$C NMR (200 MHz, CDCl$_3$) δ: 171.5, 139.5, 128.7, 127.4, 126.2, 70.5, 65.1, 62.0, 45.2, 38.0, 14.4 ppm.

To the thiazolidine (0.05 mmol) dissolved in EtOH (1 ml) was added thiobenzoic acid and the reaction was stirred for 1 hour. The reaction was then concentrated and redissolved into benzene and the mixture was then cooled to 0 degrees (C.). 3 drops of conc. HCl or preferably 3 drops of TFA was then added. The reaction was allowed to warm to room temperature and stirred for 12 hours. The mixture was then quenched with sat. sodium bicarbonate and extracted with EtOAc three times. The collected organic layers were concentrated under reduced pressure to afford thiazoline. ESI MS analysis: [MH+]=417.1

Synthesis of Aziridine-Conjugated Amino Acid Derivatives

The aziridine aldehydes i-a, i-b were synthesized as described previously (see compounds 1a and 1e of Table 1). The amino acid derivatives ii-b, ii-c, ii-d, ii-e and ii-f were synthesized using literature methods (Hill, R. R.; Birch, D.; Jeffs, G. E.; North, M. *Organic & Biomolecular Chemistry* 2003, 1, 965-972; Katritzky, A. R.; Xu, Y.-J.; He, H.-Y.; Steel, P. J. J. Chem. Soc., *Perkin Trans.* 1 2001, 1767-1770; Kyburz, E.; Els, H.; Majnoni, S.; Englert, G.; Planta, C. v.; Fuerst, A.; Plattner, P. A. *Hel. Chim. Acta* 1966, 49, 359-69; Pangbom, A. B.; Giardello, M. A.; Grubbs, R. H.; Rosen, R. K.; Timmers, F. J. *Organometallics* 1996, 15, 1518-20; Pelagatti, P.; Carcelli, M.; Calbiani, F.; Cassi, C.; Elviri, L.; Pelizzi, C.; Rizzotti, U.; Rogolino, D. *Organometallics* 2005, 24, 5836-5844).

tert-butyl (S)-4-methyl-1-(2-methylbutylamino)-1-oxopentan-2-ylcarbamate

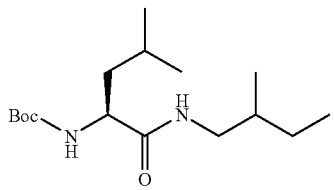

To a mixture of Boc-Leu-OH (61.3 mg, 0.26 mmol), 2-methylbutylamine (0.046 ml, 0.40 mmol) and 3 ml of MeCN in a round bottom flask equipped with a magnetic stirring bar was added DIEA (0.092 ml, 0.53 mmol) followed by HBTU (120 mg, 0.32 mmol). The reaction mixture was stirred at room temperature for 16 hours at which point TLC analysis showed that the reaction was complete. The mixture was concentrated under reduced pressure. 10 ml of DCM was added and this mixture was washed with water (×3), citric acid (1M, ×3), and brine (×1), dried over $Na_2SO_4$ and concentrated under reduced pressure. The crude $^1H$ NMR showed that the product was pure enough to carry over to the next step. $^1H$ NMR (CDCl3, 300 MHz): δ 6.75 (b, 1H), 5.21 (b, 1H), 4.18 (b, 1H), 3.17 (m, 2H), 1.77-1.07 (m, 16H), 0.98 (m, 12H) ppm; $^{13}C$ NMR (CDCl3, 75 MHz): δ 172.9, 156.0, 53.3, 45.1, 41.4, 35.0, 28.4, 27.1, 27.1, 27.0, 24.9, 23.0, 22.3, 17.2, 17.1, 11.4, 11.3 ppm. HRMS (ESI+) [M+H]+ calcd. for C16H33N2O3 301.2485, found 301.2489.

(2S)-2-amino-4-methyl-N-(2-methylbutyl)pentanamide (ii-a)

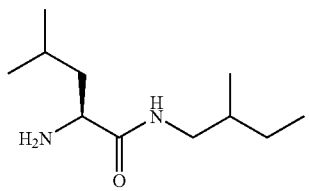

In a round bottom flask equipped with a magnetic stirring bar was added the product from above (79.2 mg, 0.26 mmol) dissolved in 1 ml of DCM. The reaction mixture was cooled to 0° C., at which point TFA (0.1 ml) was added slowly. The reaction was then brought to room temperature and stirred for 24 hours. To the reaction mixture was added sodium bicarbonate until neutral. The mixture was filtered through Celite and concentrated under reduced pressure to yield pale yellow oil (yield 90% over three steps). $^1H$ NMR (CDCl3, 400 MHz): δ δ 7.36 (b, 1H), 3.41 (d, J=7.6 Hz, 1H), 3.19 (dt, J=5.6, 6.7 Hz, 1H), 3.07 (dt, J=5.6, 6.7 Hz, 1H), 1.73 (M, 2H), 1.59 (m, 3H), 1.43 (m, 2H), 1.26 (m, 1H), 0.91 (m, 12H) ppm; $^{13}C$ NMR (CDCl3, 100 MHz): δ 175.6, 53.8, 44.7, 44.6, 44.3, 35.1, 35.0, 27.2, 27.1, 25.1, 23.6, 21.5, 17.3, 11.5 ppm. HRMS (ESI+) [M+H]+ calcd. for C11H25N2O 201.1961, found 201.1955.

(R)-propyl aziridine-2-carboxylate

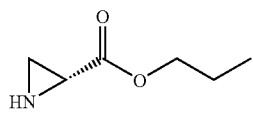

To a mixture of D-serine (10 g, 95 mmol) and 250 ml of 20% $SOCl_2$ in n-PrOH in a round bottom flask equipped with a water condenser and magnetic stirring bar was added water (100 ml). The reaction mixture was brought to 65° C. and stirred for 48 hours at which point ESI MS analysis showed that the reaction was complete. The mixture was concentrated under reduced pressure. The colorless oil was suspended in 300 ml of DCM. To this stirred mixture 20 ml of 30% ammonium hydroxide was added slowly. After stirring for 30 minutes the organic layer separated and the aqueous layer was washed with DCM (×3). The combined organic portions were dried over sodium sulfate and concentrated under reduced pressure at room temperature to afford the corresponding propyl ester. In a round bottom flask equipped with a magnetic stirring bar was added the ester from above (4.5 g, 165 mmol) dissolved in 200 ml DCM. The reaction mixture was cooled to 0° C., at which point $PPh_3$ (7 g, 26 mmol) was added followed by DIAD (95%, 5.25 ml, 26 mmol) drop wise. The reaction was then brought to room temperature and stirred for 16 hours. The reaction mixture was then concentrated at 60° C. without applying of vacuum. The crude mixture was then dissolved in diethyl ether and placed in the freezer overnight (−15° C.). Any resulting precipitate that formed was filtered off and the filtrate was concentrated and subjected to silica gel column chromatography (gradient 50% to 100% $Et_2O$ in hexanes) to yield a pale yellow oil (yield 41% over three steps). $^1H$ NMR (CDCl3, 200 MHz): δ δ 4.16-4.09 (m, 2H), 2.51 (dd, J=5.6, 2.8 Hz, 1H), 2.01 (m, 1H), 1.85 (d, J=5.6 Hz, 1H), 1.69 (dt, J=2.7, 6.7 Hz, 2H), 0.97 (t, J=6.7 Hz, 3H) ppm; $^{13}C$ NMR (CDCl3, 100 MHz): δ 173.4, 67.4, 29.2, 27.5, 22.1, 10.5 ppm. HRMS (ESI+) [M+H]+ calcd. for C6H12N1O2 130.0867, found 130.0871.

2-Aziridin-2-yl-3-oxa-1-aza-bicyclo[3.1.0]hexan-4-ol (i-d)

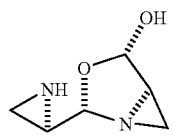

A similar procedure was followed as described previously. In a flame dried 100 ml round bottom flask equipped with a magnetic stirring bar was placed the compound from above (0.9 g, 7 mmol) in 18 ml of toluene. The solution was stirred at −78° C. for 30 min then a 1.5M solution of DIBAL in toluene (9 ml, 13.5 mmol) was added dropwise. Once the addition was complete, the reaction was allowed to stir at −78° C. for another 2 hours at which point ESI MS showed the disappearance of starting material. MeOH was slowly added at −78° C. The reaction mixture was then allowed to stir for 30 minutes while warming to room temperature. A few drops of saturated aqueous $Na_2SO_4$ were used to cause precipitation of aluminum salts, which were filtered off after stirring for another 30 minutes. The filtrate was concentrated under reduced pressure to yield a thick clear oil, which was pure enough by NMR to use in subsequent transformations. An analytically pure sample can be obtained by subjecting the crude product to flash column chromatography (silica gel; 10% methanol in DCM) to yield the title compound as a colourless oil in 57% yield. $^1$H NMR (CDCl3/Methanol-$d_4$, 90/10, 400 MHz) δ: 5.27 (s, 1H), 4.90 (s, 1H), 2.65 (m, 1H), 2.39 (m, 1H), 1.84 (m, 2H), 1.64 (d, J=5.2 Hz, 1H), 1.32 (d, J=4 Hz, 1H), 1.26 (d, J=2.8 Hz, 1H) ppm. $^{13}$CNMR (CDCl3/Methanol-$d_4$, 90/10, 100 MHz) δ: 95.9, 95.8, 94.7, 43.6, 43.5, 31.0, 27.6, 20.9, 20.8 ppm.

(2R,3S)-propyl 3-methylaziridine-2-carboxylate

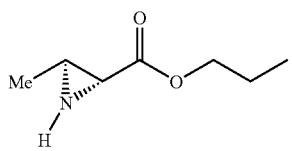

To a mixture of D-threonine (10 g, 84 mmol) and 200 ml of 20% $SOCl_2$ in n-PrOH in a round bottom flask equipped with a water condenser and magnetic stirring bar was added water (50 ml). The reaction mixture was brought to 65° C. and stirred for 24 hours at which point ESI MS analysis showed that the reaction was complete. The mixture was concentrated under reduced pressure. The colorless oil was suspended in 300 ml of DCM. To this stirring mixture 20 ml of 23% ammonium hydroxide was added slowly. After stirring for 30 minutes, the organic layer separated and the aqueous layer was washed with DCM (×3). The combined organic portions were dried over sodium sulfate and concentrated to afford the corresponding propyl ester. In a round bottom flask equipped with a magnetic stirring bar was added the ester from above (12 g, 74.5 mmol) dissolved in 200 ml of DCM. The reaction mixture was cooled to 0° C., at which point $PPh_3$ (19.5 g, 74.5 mmol) was added followed by DIAD (95%, 14.7 ml, 74.5 mmol) drop wise. The reaction was then brought to room temperature and stirred for 16 hours. The reaction mixture was concentrated at 60° C. without applying of vacuum. The crude mixture was then dissolved in diethyl ether and filtered. The filtrate was concentrated and subsequently dissolved in pentane and placed in the freezer overnight (−15° C.). Any resulting precipitate that formed was filtered off and the filtrate was concentrated and subjected to silica gel column chromatography (gradient 50% to 100% $Et_2O$ in hexanes) to yield a pale yellow oil (yield 36% over three steps). $^1$H NMR (CDCl$_3$, 400 MHz) δ: 4.05 (t, J=9.2 Hz, 2H), 2.56 (d, J=8 Hz, 1H), 2.22 (t, J=7.7 Hz, 1H), 1.60 (dt, 9.2, 10 Hz, 2H), 1.22 (d, 7.7 Hz, 3H), 0.88 (t, J=10 Hz, 3H) ppm. $^{13}$C NMR (Methanol-$d_4$, 100 MHz) δ: 171.0, 66.9, 35.0, 33.7, 22.1, 13.1, 10.3 ppm. HRMS (ESI) [M]$^+$ calcd. For C7H13NO2 144.1019, found 144.1022.

6-Methyl-2-(3-methyl-aziridin-2-yl)-3-oxa-1-aza-bicyclo[3.1.0]hexan-4-ol (i-c)

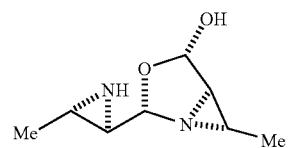

A similar procedure was followed as described previously. In a flame dried 100 ml round bottom flask equipped with a magnetic stirring bar was placed the compound from above (0.42 g, 2.9 mmol) in 4 ml toluene. The solution was stirred at −78° C. for 30 minutes then a 1.5M solution of DIBAL in toluene (3.8 ml, 5.7 mmol) was added dropwise. Once the addition was complete, the reaction was allowed to stir at −78° C. for another 2 hours at which point ESI MS showed disappearance of starting material. MeOH was slowly added at −78° C. The reaction mixture was then allowed to stir for 30 minutes while warming to room temperature. A few drops of saturated aqueous $Na_2SO_4$ were used to cause precipitation of aluminum salts, which were filtered off after stirring for another 30 minutes. The filtrate was concentrated under reduced pressure to yield a thick clear oil, which was pure enough by NMR for use in subsequent transformations. An analytically pure sample was obtained by subjecting the crude product to flash column chromatography (silica gel; 10% MeOH in DCM) to yield the title compound as a colourless oil in 51% yield. $^1$HNMR (CDCl$_3$, 400 MHz) δ: 5.19 (s, 1H), 4.89 (s, 1H), 2.69 (d, J=5.4 Hz, 1H), 2.37-2.27 (m, 2H), 2.10 (m, 1H), 1.37 (d, J=5.5 Hz, 3H), 1.19 (d, J=6.4 Hz, 3H) ppm. $^{13}$CNMR (CDCl$_3$, 100 MHz) δ: 95.8, 95.7, 91.4, 91.3, 47.7, 47.6, 37.2, 33.7, 30.9, 12.4, 7.0 ppm.

TABLE 16

Condition screening.

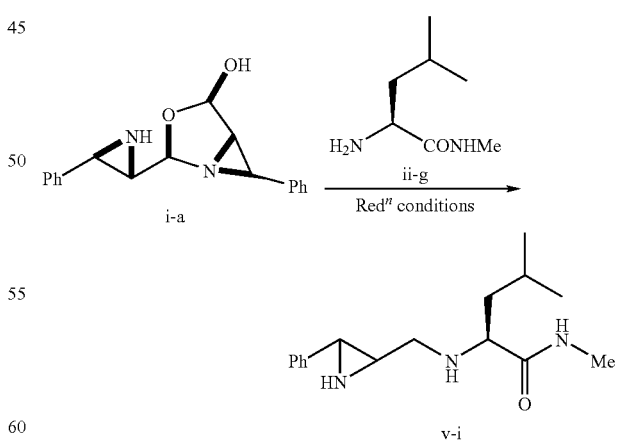

| Entry | Reduction conditions | Yield (%) |
|---|---|---|
| 1 | NaCNBH$_3$, MeOH, HAOc (1% in MeOH) | 7% |
| 2 | NaCNBH$_3$, MeOH | 3% |
| 3 | NaHB(OAc)$_3$, MeOH | no rxn |
| 4 | NaCNBH$_3$, TFE | —$^b$ |

TABLE 16-continued

Condition screening.

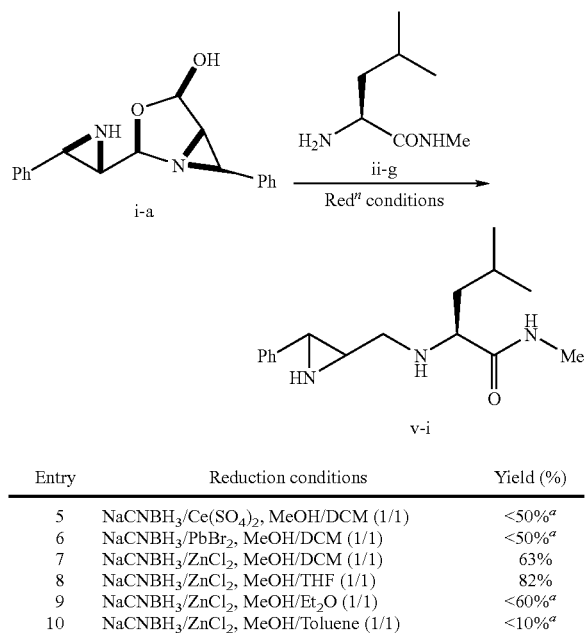

| Entry | Reduction conditions | Yield (%) |
|---|---|---|
| 5 | NaCNBH$_3$/Ce(SO$_4$)$_2$, MeOH/DCM (1/1) | <50%[a] |
| 6 | NaCNBH$_3$/PbBr$_2$, MeOH/DCM (1/1) | <50%[a] |
| 7 | NaCNBH$_3$/ZnCl$_2$, MeOH/DCM (1/1) | 63% |
| 8 | NaCNBH$_3$/ZnCl$_2$, MeOH/THF (1/1) | 82% |
| 9 | NaCNBH$_3$/ZnCl$_2$, MeOH/Et$_2$O (1/1) | <60%[a] |
| 10 | NaCNBH$_3$/ZnCl$_2$, MeOH/Toluene (1/1) | <10%[a] |

[a]Determined by NMR analysis;
[b]Aldehyde reduction product was obtained.

General Procedure for Condition Screening:

In a flame dried 10 ml round bottom flask equipped with a magnetic stirring bar was placed i-a (15 mg, 0.05 mmol) and ii-g (17 mg, 0.12 mmol) in 1 ml of solvent combination. The solution was stirred at room temperature and ZnCl$_2$ (14 mg, 0.10 mmol) was added. The mixture was stirred for 1 minute at which point NaCNBH$_3$ (10 mg, 0.15 mmol) was added. The reaction was allowed to stir at room temperature overnight at which point ESI MS showed the reaction was complete. The reaction mixture was then filtered through Celite. The filtrate was concentrated under reduced pressure and NMR analysis for the crude product was performed. For Entry 1, 2, 4, 7, 8, the crude product was purified by silica gel column chromatography (DCM/MeOH, 90/10). All operations should be done in the fume hood to avoid evolution of highly toxic HCN.

(2S)—N,4-dimethyl-24(3-phenylaziridin-2-yl)methylamino)pentanamide (v-i)

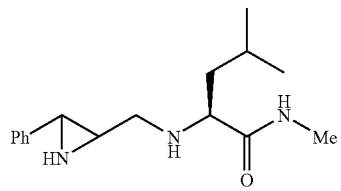

$^1$H NMR (CDCl3, 400 MHz): δ 7.32-7.14 ppm (m, 5H), 3.18-3.17 (dt, J=8.6, 4.5 Hz, 1H), 2.83-2.57 (m, 6H), 2.31 (b, 1H), 1.73-1.67 (m, 1H), 1.62-1.38 (m, 1H), 1.36-1.30 (m, 1H), 1.27 (b, 1H), 0.92 (m, 6H) ppm; $^{13}$C NMR (CDCl3, 100 MHz): δ 175.6, 175.5, 139.7, 139.6, 129.0, 128.8, 127.6, 127.5, 125.7, 125.6, 61.9, 61.4, 52.2, 51.5, 43.3, 43.2, 41.0, 40.9, 38.6, 38.2, 26.0, 25.3, 23.5, 23.4, 22.2, 22.1 ppm. HRMS (ESI) [M+H]+ calcd. for C16H26N3O 276.2027, found 276.2059.

(2S)-4-methyl-N-(2-methylbutyl)-2-((3-phenylaziridin-2-yl)methylamino)pentanamide (v-a)

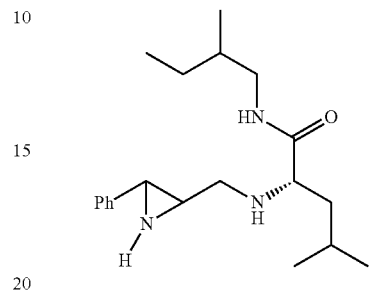

In a flame dried 10 ml round bottom flask equipped with a magnetic stirring bar was placed racemic i-a (30 mg, 0.10 mmol) and racemic ii-a (60 mg, 0.30 mmol) in 1 ml of THF and 1 ml of MeOH. The solution was stirred at room temperature and ZnCl$_2$ (27 mg, 0.20 mmol) was added. The mixture was stirred for 1 minute at which point NaCNBH$_3$ (13 mg, 0.3 mmol) was added. The reaction was allowed to stir at room temperature overnight at which point ESI MS showed the reaction was complete. The reaction mixture was then filtered through Celite. The filtrate was concentrated under reduced pressure and subjected to silica gel column chromatography (DCM/MeOH/TEA 95/4/1) to yield a colorless oil. The combined yield was 85% (1:1 mixture of diastereomers). All operations should be done in the fume hood to avoid evolution of highly toxic HCN. $^1$H NMR (CDCl$_3$, 400 MHz) δ: 7.34-7.16 (m, 5H), 3.03-2.98 (m, 3H), 2.87-2.76 (m, 3H), 2.34 (b, 1H), 1.76-1.35 (m, 6H), 1.17 (m, 2H), 0.92 (m, 12H) ppm. $^{13}$C NMR (CDCl$_3$, 100 MHz) δ: 174.7, 139.7, 129.0, 128.8, 127.6, 61.9, 61.4, 44.7, 43.5, 43.4, 35.2, 27.3, 27.2, 25.4, 23.4, 23.3, 22.3, 22.1, 17.5, 11.5 ppm. HRMS (ESI) [M+H]+ calcd. for C20H34N3O 332.2696, found 332.2700.

(2S)—N,N-dimethyl-3-phenyl-2-(3-phenylaziridin-2-yl)methylamino)propanamide (v-b)

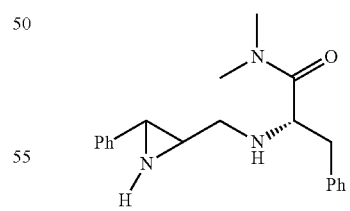

In a flame dried 10 ml round bottom flask equipped with a magnetic stirring bar was placed racemic i-a (66 mg, 0.22 mmol) and ii-b (103 mg, 0.54 mmol) in 1.5 ml of THF and 1.5 ml of MeOH. The solution was stirred at room temperature and ZnCl$_2$ (61 mg, 0.45 mmol) was added. The mixture was stirred for 1 minute at which point NaCNBH$_3$ (43 mg, 0.70 mmol) was added. The reaction was allowed to stir at room temperature overnight at which point ESI MS showed the reaction was complete. The reaction mixture was then filtered through Celite. The filtrate was concentrated under reduced pressure and subjected to silica gel column chromatography (Gradient: Ethyl acetate/MeOH, 95/5-90-10) to yield colorless oil (1:1 mixture of diastereomers) in 75% yield. All operations should be done in the fume hood to avoid evolution of highly toxic HCN. $^1$H NMR (CDCl3, 200 MHz): δ 7.32-7.19 ppm (m, 10H), 3.82 (t, J=14.4 Hz, 1H), 2.98-2.85 (m, 2H), 2.89 (s, 3H), 2.79-2.56 (m, 2H), 2.56 (s, 3H), 2.24 (b, 1H), 1.58 (b, 2H) ppm; $^{13}$C NMR (CDCl3, 100 MHz): δ 174.3, 138.1, 129.5, 129.4, 128.7, 128.6, 127.3, 126.9, 125.9, 60.3, 50.6, 40.9, 36.7, 35.8 ppm. HRMS (EI+) [M]+ calcd. for C20H25N3O 323.1998, found 323.1993.

(2S)-methyl 5-(2-nitroguanidino)-2-((3-phenylaziridin-2-yl)methylamino)pentanoate (v-c)

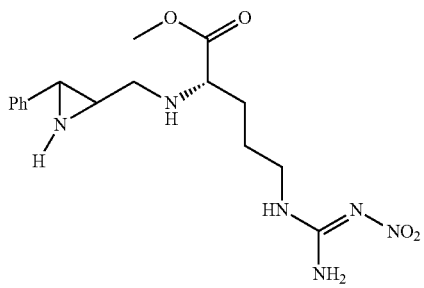

In a flame dried 10 ml round bottom flask equipped with a magnetic stirring bar was placed racemic i-a (80 mg, 0.27 mmol) and ii-c (276 mg, 1.2 mmol) in 1.5 ml of THF and 1.5 ml of MeOH. The solution was stirred at room temperature and ZnCl$_2$ (82 mg, 0.6 mmol) was added. The mixture was stirred for 1 minute at which point NaCNBH$_3$ (60 mg, 0.9 mmol) was added. The reaction was allowed to stir at room temperature overnight at which point ESI MS showed the reaction was complete. The reaction mixture was then filtered through Celite. The filtrate was concentrated under reduced pressure and subjected to silica gel column chromatography (gradient DCM/MeOH 95/5 to 80/20) to yield colorless oil (1:1 mixture of diastereomers). The combined yield was 86%. All operations should be done in the fume hood to avoid evolution of highly toxic HCN. $^1$H NMR (CDCl3, 400 MHz): δ 8.80 (b, 2H), 7.95 (b, 3H), 7.32-7.19 ppm (m, 5H), 3.74 (s, 3H), 3.47 (m, 3H), 2.84 (m, 2H), 2.41 (m, 2H), 1.84-1.75 (m, 6H) ppm; $^{13}$C NMR (CDCl3, 100 MHz): δ 175.3, 175.2, 159.6, 129.0, 128.9, 127.7, 125.8, 125.7, 61.1, 60.9, 52.4, 52.3, 51.3, 50.9, 41.3, 41.0, 40.4, 38.4, 25.6 ppm. HRMS (EI+) [M]+ calcd. for C16H24N6O4 365.1931, found 365.1984.

(2S)-3-methyl-N-phenyl-2-((3-phenylaziridin-2-yl)methylamino)butanamide (v-d)

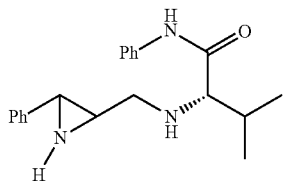

In a flame dried 10 ml round bottom flask equipped with a magnetic stirring bar was placed racemic i-a (22.5 mg, 0.08 mmol) and ii-d (32.3 mg, 0.17 mmol) in 0.7 ml of THF and 0.7 ml of MeOH. The solution was stirred at room temperature and ZnCl$_2$ (20.8 mg, 0.15 mmol) was added. The mixture was stirred for 1 minute at which point NaCNBH$_3$ (14.5 mg, 0.23 mmol) was added. The reaction was allowed to stir at room temperature for overnight at which point ESI MS showed the reaction was complete. The reaction mixture was then filtered through Celite. The filtrate was concentrated under reduced pressure and subjected to silica gel column chromatography (DCM/MeOH 95/5) to yield colorless oil (1:1 mixture of diastereomers). The combined yield was 81%. All operations should be done in the fume hood to avoid evolution of highly toxic HCN. $^1$H NMR (CDCl$_3$, 400 MHz) δ: 9.47 (s, 0.5H), 9.22 (s, 0.5H), 7.61 (m, 2H), 7.33-7.06 (m, 6H), 3.11 (d, J=4.5 Hz, 0.5H), 3.07 (d, J=4.5 Hz, 0.5H), 3.07-2.72 (m, 3H), 2.40 (m, 1H), 2.24 (m, 1H), 1.07 (b, 2H), 1.00 (d, J=7.6 Hz, 2H), 0.96 (d, J=7.6 Hz, 2H) ppm. $^{13}$C NMR (CDCl$_3$, 100 MHz) δ: 172.2, 173.1, 139.5, 139.4, 138.0, 137.9, 129.2, 128.9, 127.7, 125.7, 124.3, 124.2, 119.8, 69.4, 69.3, 68.8, 68.2, 52.8, 52.3, 39.0, 38.5, 31.9, 19.9, 19.8, 18.1 ppm. HRMS (ESI) [M]$^+$ calcd. For C20H26N3O 324.2072, found 324.2081.

(S)-2-(((2R,3S)-3-((tert-butyldimethylsilyloxy)methyl)aziridin-2-yl)methylamino)-3-methyl-N-phenylbutanamide (v-e L)

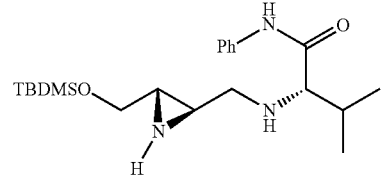

In a flame dried 10 ml round bottom flask equipped with a magnetic stirring bar was placed enantiomerically pure i-b (91 mg, 0.21 mmol) and ii-d (97 mg, 0.5 mmol) in 2.5 ml of THF, DCM 1 ml and 2.5 ml of MeOH. The solution was stirred at room temperature and ZnCl$_2$ (57 mg, 0.42 mmol) was added. The mixture was stirred for 1 minute at which point NaCNBH$_3$ (40 mg, 0.6 mmol) was added. The reaction was allowed to stir at room temperature overnight at which point ESI MS showed the reaction was complete. The reaction mixture was then filtered through Celite. The filtrate was concentrated under reduced pressure and subjected to silica gel column chromatography (Ethyl acetate/MeOH: 95/5) to yield colorless oil. The combined yield was in 92%. All operations should be done in the fume hood to avoid evolution of highly toxic HCN. $^1$H NMR (CDCl3, 400 MHz): δ 7.65 (d, J=7.6 Hz, 2H), 7.34 (t, J=8.0 Hz, 2H), 7.09 (d, J=7.6 Hz 1H), 3.79 (m, 2H), 3.01 (d, J=4.4 Hz, 1H), 2.78 (dd, J=4.4, 12.6 Hz, 1H), 2.59 (dd, J=6.6, 13 Hz, 1H), 2.19 (m, 1H), 2.06 (m, 1H), 1.91 (m, 1H), 1.60 (b, 2H), 1.03 (d, J=6.7 Hz, 3H), 0.96 (d, J=6.7 Hz, 3H), 0.87 (s, 9H), 0.03 (d, J=3.2 Hz, 6H) ppm; $^{13}$C NMR (CDCl3, 100 MHz): δ 172.4, 138.1, 129.1, 124.1, 119.6, 69.3, 60.6, 52.1, 36.6, 32.6, 31.8, 26.1, 26.0, 19.8, 18.4, 18.0, −5.2, −5.3 ppm. HRMS (ESI+) [M+H]+ calcd. for C21H38N3O2Si 392.2727, found 392.2746.

(R)-2-(((2R,3S)-3-((tert-butyldimethylsilyloxy)methyl)aziridin-2-yl)methylamino)-3-methyl-N-phenylbutanamide (v-e D)

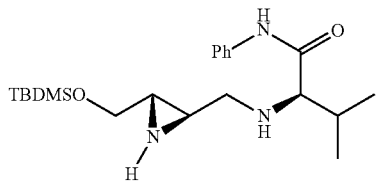

The same procedure was used as that for v-e L with the exception that ii-e was used instead of ii-d. $^1$H NMR (CDCl3, 400 MHz): δ 7.60 (d, J=7.6 Hz, 2H), 7.30 (t, J=8.0 Hz, 2H), 7.07 (d, J=7.6 Hz 1H), 3.79 (m, 2H), 3.03 (d, J=4.4 Hz, 1H), 2.76 (dd, J=4.3, 12.6 Hz, 1H), 2.50 (dd, J=6.6, 12.6 Hz, 1H), 2.19 (m, 1H), 2.06 (m, 1H), 1.91 (m, 1H), 1.40 (b, 2H), 1.01 (d, J=6.8 Hz, 3H), 0.89 (d, J=6.8 Hz, 3H), 0.80 (s, 9H), 0.01 (d, J=3.2 Hz, 6H) ppm; $^{13}$C NMR (CDCl3, 100 MHz): δ 172.3, 138.0, 129.1, 124.1, 119.6, 68.3, 60.6, 51.2, 37.0, 32.2, 31.7, 26.0, 25.9, 19.9, 18.4, 17.7, −5.2, −5.3 ppm. HRMS (ESI+) [M+H]+ calcd. for C21H38N3O2Si 392.2727, found 392.2735.

(S)-2-(((2R,3S)-3-((tert-butyldimethylsilyloxy)methyl)aziridin-2-yl)methylamino)-4-methyl-N-phenylpentanamide (v-f)

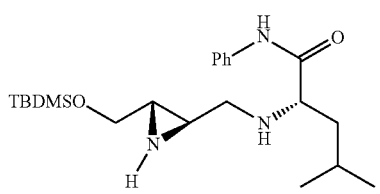

In a flame dried 10 ml round bottom flask equipped with a magnetic stirring bar was placed enantiomerically pure i-b (38 mg, 0.09 mmol) and ii-f (43.7 mg, 0.21 mmol) in 0.8 ml of THF, DCM 0.4 ml and 0.8 ml of MeOH. The solution was stirred at room temperature and ZnCl$_2$ (24.1 mg, 0.18 mmol) was added. The mixture was stirred for 1 minute at which point NaCNBH$_3$ (16.7 mg, 0.27 mmol) was added. The reaction was allowed to stir at room temperature overnight at which point ESI MS showed the reaction was complete. The reaction mixture was then filtered through Celite. The filtrate was concentrated under reduced pressure and subjected to silica gel column chromatography (Ethyl acetate/MeOH: 95/5) to yield colorless oil in 84% yield. All operations should be done in the fume hood to avoid evolution of highly toxic HCN. $^1$H NMR (CDCl$_3$, 400 MHz) δ: 7.62 (d, J=7.9 Hz, 2H), 7.32 (t, J=7.1 Hz, 2H), 7.09 (t, J=7.1 Hz, 1H), 3.77 (dd, J=8, 2.8 Hz, 2H), 3.20 (d, J=4.8 Hz, 1H), 2.78 (d, J=2.6 Hz, 1H), 2.68-2.58 (m, 2H), 2.11 (m, 1H), 1.97 (m, 1H), 1.91 (m, 3H), 1.67 (m, 1H), 0.94 (m, 6H), 0.85 (s, 9H), 0.02 (d, J=6.5 Hz, 6H), ppm. $^{13}$C NMR (CDCl$_3$, 100 MHz) δ: 173.5, 138.4, 129.2, 124.1, 119.6, 62.2, 62.1, 60.5, 51.3, 43.2, 43.1, 36.5, 32.5, 26.1, 25.5, 25.4, 23.4, 22.3, 18.5, −5.3 ppm. HRMS (ESI) [M+H]$^+$ calcd. For C22H40N3O2Si 406.2884, found 406.2903.

(S)-3-methyl-2-(((2S,3S)-3-methylaziridin-2-yl)methylamino)-N-phenylbutanamide (v-g)

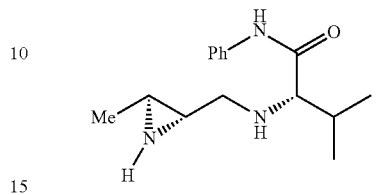

In a flame dried 10 ml round bottom flask equipped with a magnetic stirring bar was placed enantiomerically pure i-c (29 mg, 0.15 mmol) and ii-d (72 mg, 0.37 mmol) in 1 ml of THF 1 ml of MeOH. The solution was stirred at room temperature and ZnCl$_2$ (47 mg, 0.3 mmol) was added. The mixture was stirred for 1 minute at which point NaCNBH$_3$ (32 mg, 0.45 mmol) was added. The reaction was allowed to stir at room temperature overnight at which point ESI MS showed the reaction was complete. The reaction mixture was then filtered through Celite. The filtrate was concentrated under reduced pressure and subjected to silica gel column chromatography (gradient Ethyl acetate/MeOH: 95/5-90/10) to yield colorless oil in 60% yield. All operations should be done in the fume hood to avoid evolution of highly toxic HCN. $^1$H NMR (CDCl$_3$, 400 MHz) δ: 7.62 (dd, J=1.1, 7.9 Hz, 2H), 7.32 (t, J=7.1 Hz, 2H), 7.09 (t, J=7.1 Hz, 1H), 3.10 (d, J=4.0 Hz, 1H), 2.70 (m, 2H), 2.22-2.19 (m, 3H), 1.27 (b, 2H), 1.26 (d, J=4.5 Hz, 2H), 1.17 (d, J=5.6 Hz, 3H), 1.07 (d, J=7.2 Hz, 3H), 0.94 (d, J=7.2 Hz, 3H) ppm. $^{13}$C NMR (CDCl$_3$, 100 MHz) δ: 172.3, 138.0, 129.2, 124.2, 119.7, 68.6, 68.5, 48.4, 34.0, 31.7, 29.9, 20.0, 17.7, 14.1 ppm. HRMS (EI) [M]$^+$ calcd. For C15H23N3O 261.1844, found 261.1844.

(S)-2-((R)-aziridin-2-ylmethylamino)-3-methyl-N-phenylbutanamide (v-h)

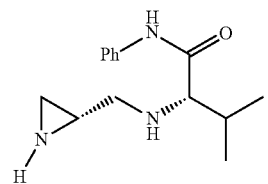

In a flame dried 10 ml round bottom flask equipped with a magnetic stirring bar was placed enantiomerically pure i-d (24 mg, 0.17 mmol) and ii-d (77 mg, 0.4 mmol) in 1.5 ml of THF, 1 ml of DCM and 1.5 ml of MeOH. The solution was stirred at room temperature and ZnCl$_2$ (50 mg, 0.37 mmol) was added. The mixture was stirred for 1 minute at which point NaCNBH$_3$ (35 mg, 0.56 mmol) was added. The reaction was allowed to stir at room temperature overnight at which point ESI MS showed the reaction was complete. The reaction mixture was then filtered through Celite. The filtrate was concentrated under reduced pressure and subjected to silica gel column chromatography (gradient Et20/MeOH: 90/0-80/20) to yield colorless oil in 51% yield. All operations should be done in the fume hood to avoid evolution of highly toxic HCN. $^1$H NMR (CDCl3/Methanol-d$_4$, 97/3, 400 MHz) δ: 7.60-7.09 (m, 5H), 3.33 (d, J=6.4 Hz, 2H), 2.78 (m, 1H), 2.69 (m, 1H), 2.41 (d, J=5.6 Hz, 1H),2.23 (m, 1H), 2.03 (d, J=3.8 Hz, 1H), 1.22 (d, J=5.6 Hz, 3H), 1.00 (d, J=5.6 Hz, 3H) ppm. $^{13}$C NMR (Methanol-d$_4$, 100 MHz) δ: 174.3, 137.0, 128.9, 125.2, 120.4, 66.3, 49.2, 32.9, 29.5, 18.4, 16.3 ppm. HRMS (ESI) [M+H]$^+$ calcd. For C14H22N3O 248.1759, found 248.1761.

S—(S)-2-benzamido-3-((S)-3-methyl-1-oxo-1-(phenylamino)butan-2-ylamino)propyl benzothioate (vi)

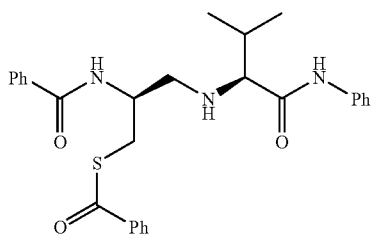

In a flame dried 10 ml round bottom flask equipped with a magnetic stirring bar was placed v-h (16 mg, 0.07 mmol) in 15 ml of MeOH and 0.5 ml of DCM. The solution was cooled down to 0° C. at which point thiobenzoic acid (94%, 21 mg, 0.14 mmol) was added. The mixture was stirred at 0° C. for 6 hours then brought to room temperature and stirred for 18 hours. The reaction mixture was concentrated under reduced pressure and subjected to silica gel column chromatography (40% ethyl acetate in hexanes) to yield a white solid in 82% yield. $^1$H NMR (CDCl$_3$, 400 MHz) δ: 8.09-7.03 (m, 15H), 4.59 (m, 1H), 3.51 (m, 1H), 3.35 (d, J=4.3 Hz, 1H), 3.10 (d, J=8.3 Hz, 2H), 2.91 (m, 1H), 2.21 (m, 1H), 1.04 (d, J=6.4 Hz, 3H), 0.95 (d, J=6.4 Hz, 3H) ppm. $^{13}$C NMR (CDCl$_3$, 100 MHz) δ: 193.2, 172.1, 168.1, 137.6, 136.5, 134.1, 133.9, 132.0, 130.3, 129.1, 128.9, 128.7, 127.6, 124.4, 119.8, 69.3, 52.8, 50.7, 31.9, 31.4, 19.8, 18.3 ppm. HRMS (ESI) [M+H]$^+$ calcd. For C28H32N3O3S 490.2158, found 490.2179.

Synthesis of Aziridine-Conjugated Nucleosides

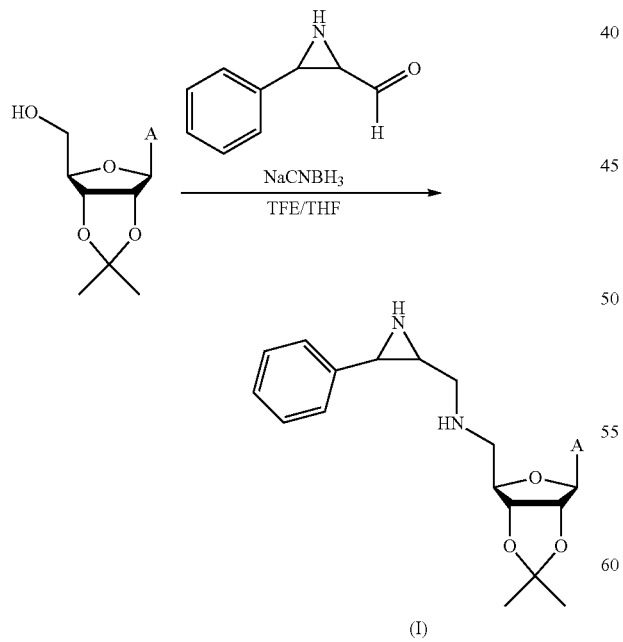

The aziridine aldehyde (4.2 mg, 0.0288 mmol) and the sugar (18.7 mg, 0.061 mmol) were mixed in dry TFE. The mixture was allowed to stir for 20 minutes before NaCNBH$_3$ (92 μl, 0.092 mmol, 1 M solution in THF). The reaction was stirred over night and 4-5 drops of NaHCO$_3$ was added carefully the next day to quench the reaction. 2 ml of water was added and the aqueous layer was extracted with 3×1 ml CHCl$_3$. The combined organic phases were dried with Na$_2$SO$_4$ and evaporated before purification with silica column (CH$_2$Cl$_2$:MeOH:NH$_4$O 90:10:1). Product was isolated as a white solid (6.1 mg, 0.014 mmol). (conversion/selectivity/yield=100%/48%/48%). $^1$H-NMR (300 MHz, CDCl$_3$) δ 8.36 (d, 1H), 8.34 (s, 1H), 7.33-7.11 (m, 5H), 6.01 (t, 1H), 5.62 (br s, 2H), 5.48 (m, 1H), 5.05 (m, 1H), 3.05-2.90 (m, 4H), 2.77 (br s, 1H), 1.62 (s, 3H), 1.39 (s, 3H).

Every reference cited herein is hereby incorporated by reference in its entirety.

What is claimed is:

1. A compound of formula (Ia):

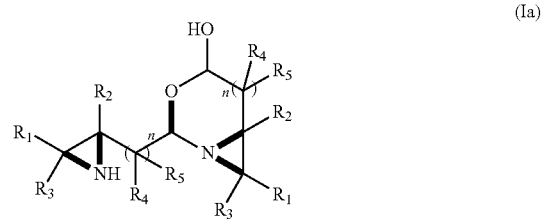

wherein n=0 or 1, and R$_1$, R$_2$, R$_3$, R$_4$ and R$_5$ are independently selected from H; lower alkyl; aryl; heteroaryl; alkenyl; cycloalkyl; heterocycle; esters of the formula —C(O)OR* wherein R* is selected from alkyl and aryl; amides of the formula —C(O)NRR*, wherein R and R* are independently selected from alkyl and aryl; —CH$_2$C(O)R, wherein R is selected from —OH, lower alkyl, aryl, -loweralkyl-aryl, or —NR$_a$R$_b$, where R$_a$ and R$_b$ are independently selected from H, lower alkyl, aryl or -loweralkyl-aryl; —C(O)R$_c$, wherein R$_c$ is selected from lower alkyl, aryl or -loweralkyl-aryl; or -lower alkyl-OR$_d$, wherein R$_d$ is a suitable protecting group;

all of which are optionally substituted at one or more substitutable positions with one or more suitable substituents, with the proviso that when R$_2$ is phenyl, R$_3$ is methyl, and n=0 then R$_1$ cannot be —C(O)NEt$_2$.

2. A compound as claimed in claim 1 wherein n=0, R$_1$ and R$_3$ are independently selected from H; aryl; heteroaryl; and -lower alkyl-OR$_d$, wherein R$_d$ is a suitable protecting group, and R$_2$ is selected from H and aryl.

3. A compound as claimed in claim 1 selected from the group consisting of:

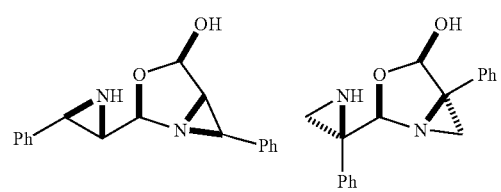

-continued

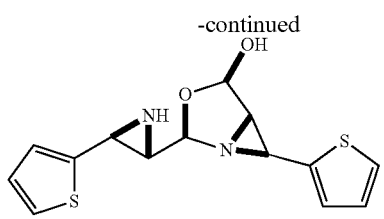

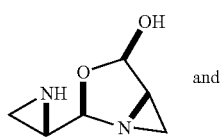 and

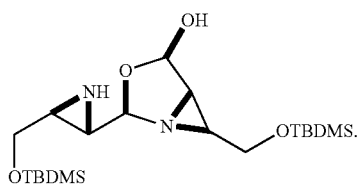

4. A process for producing a compound of formula (Ia) and/or (Ib) as defined in claim 1 wherein the process is selected from any one of the following processes on the basis of compatibility of groups $R_1$, $R_2$, $R_3$, $R_4$, and $R_5$ with said process:

(a) reacting a compound of the formula (IIa)

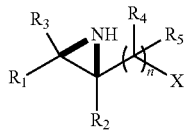

(IIa)

wherein n, $R_1$, $R_2$, $R_3$, $R_4$, and $R_5$ are as defined in claim 1 and X is selected from

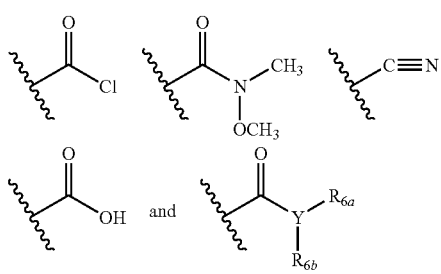

wherein Y is oxygen or nitrogen, and
  when Y is oxygen, $R_{6b}$ is absent, and $R_{6a}$ is selected from lower alkyl; aryl;
  and -loweralkyl-aryl, and
  when Y is nitrogen, $R_{6a}$ and $R_{6b}$ are independently selected from hydrogen, lower alkyl; alkoxy; aryl; and -loweralkyl-aryl;
with a hydride transfer reagent to form the compound of formula (Ia) and/or (Ib) as defined in claim 1;

(b) reducing a compound of formula (IIb)

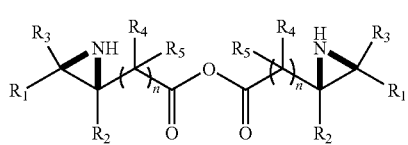

(IIb)

wherein n, $R_1$, $R_2$, $R_3$, $R_4$, and $R_5$ are as defined in claim 1 to produce the compound of formula (Ia) and/or (Ib) as defined in claim 1;

(c) Fukuyama reduction of a compound of formula (IIc)

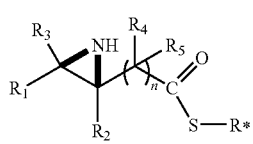

(IIc)

wherein n, $R_1$, $R_2$, $R_3$, $R_4$, and $R_5$ are as defined in claim 1 and

R* is selected from aryl; alkyl; heteroaryl; and heteroalkyl;

to produce the compound of formula (Ia) and/or (Ib) as defined in claim 1;

(d) oxidative cleavage of a compound of formula (IId)

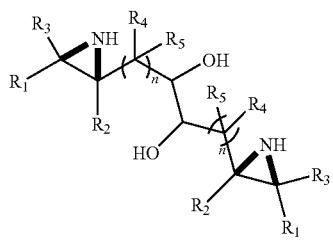

(IId)

wherein n, $R_1$, $R_2$, $R_3$, $R_4$, and $R_5$ are as defined in claim 1 to produce the compound of formula (Ia) and/or (Ib) as defined in claim 1;

(e) oxidation of a compound of formula (IIe)

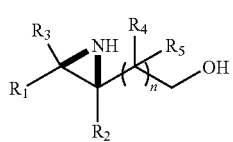

(IIe)

wherein n, $R_1$, $R_2$, $R_3$, $R_4$, and $R_5$ are as defined in claim 1 to produce the compound of formula (Ia) and/or (Ib) as defined in claim 1; and (f) oxidative cleavage of a compound of formula (IIf)

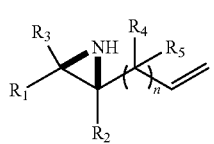

(IIf)

wherein n, $R_1$, $R_2$, $R_3$, $R_4$, and $R_5$ are as defined in claim 1 to produce the compound of formula (Ia) and/or (Ib) as defined in claim 1.

5. The process of claim 4 wherein process (a) is selected and X is

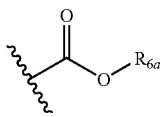

wherein $R_{6a}$ is selected from lower alkyl; aryl; and -loweralkyl-aryl.

6. The process of claim 5 wherein the hydride transfer reagent used in said process is diisobutylaluminum hydride.

7. A method for preparing an aziridine-conjugated bioactive molecule selected from an amino acid and peptide comprising coupling a suitably protected amino acid or peptide having a free amino group to a compound of formula (Ia) as defined in claim 1 via reductive amination to form the aziridine-conjugated amino acid or peptide.

8. The process of claim 7 wherein the reductive amination conditions are selected from the following based on the solubility and stability of the bioactive molecule under said conditions:

$NaCNBH_3$, methanol, acetic acid (1% in methanol);
$NaCNBH_3$, methanol;
$NaCNBH_3/Ce(SO_4)_2$, methanol/dichloromethane (1/1);
$NaCNBH_3/PbBr_2$, methanol/dichloromethane (1/1);
$NaCNBH_3/ZnCl_2$, methanol/dichloromethane (1/1);
$NaCNBH_3/ZnCl_2$, methanol/tetrahydrofuran (1/1);
$NaCNBH_3/ZnCl_2$, methanol/diethyl ether (1/1); and
$NaCNBH_3/ZnCl_2$, methanol/toluene (1/1).

9. The process of claim 7 wherein the bioactive molecule is a suitably protected amino acid and the reductive amination conditions are $NaCNBH_3/ZnCl_2$, methanol/tetrahydrofuran (1/1).

10. An aziridine-conjugated amino acid or peptide prepared by the process of claim 7.

11. A compound as claimed in claim 1, wherein $R_1$ is selected from lower alkyl; aryl; heteroaryl; alkenyl; cycloalkyl; heterocycle; esters of the formula —C(O)OR* wherein R* is selected from alkyl and aryl; amides of the formula —C(O)NRR*, wherein R and R* are independently selected from alkyl and aryl; —$CH_2C(O)R$, wherein R is selected from —OH, lower alkyl, aryl, -loweralkyl-aryl, or —$NR_aR_b$, where $R_a$ and $R_b$ are independently selected from H, lower alkyl, aryl or -loweralkyl-aryl; —C(O)$R_c$, wherein $R_c$ is selected from lower alkyl, aryl or -loweralkyl-aryl; or -lower alkyl-$OR_d$, wherein $R_d$ is a suitable protecting group; all of which are optionally substituted at one or more substitutable positions with one or more suitable substituents.

12. A compound as claimed in claim 1, wherein $R_2$ is selected from lower alkyl; aryl; heteroaryl; alkenyl; cycloalkyl; heterocycle; esters of the formula —C(O)OR* wherein R* is selected from alkyl and aryl; amides of the formula —C(O)NRR*, wherein R and R* are independently selected from alkyl and aryl; —$CH_2C(O)R$, wherein R is selected from —OH, lower alkyl, aryl, -loweralkyl-aryl, or $NR_aR_b$, where $R_a$ and $R_b$ are independently selected from H, lower alkyl, aryl or -loweralkyl-aryl; —C(O)$R_c$, wherein $R_c$ is selected from lower alkyl, aryl or -loweralkyl-aryl; or -lower alkyl-$OR_d$, wherein $R_d$ is a suitable protecting group;

all of which are optionally substituted at one or more substitutable positions with one or more suitable substituents.

13. A compound as claimed in claim 1, wherein $R_3$ is selected from lower alkyl; aryl; heteroaryl; alkenyl; cycloalkyl; heterocycle; esters of the formula —C(O)OR* wherein R* is selected from alkyl and aryl; amides of the formula —C(O)NRR*, wherein R and R* are independently selected from alkyl and aryl; —$CH_2C(O)R$, wherein R is selected from —OH, lower alkyl, aryl, -loweralkyl-aryl, or $NR_aR_b$, where $R_a$ and $R_b$ are independently selected from H, lower alkyl, aryl or -loweralkyl-aryl; —C(O)$R_c$, wherein $R_c$ is selected from lower alkyl, aryl or -loweralkyl-aryl; or -lower alkyl-$OR_d$, wherein $R_d$ is a suitable protecting group;

all of which are optionally substituted at one or more substitutable positions with one or more suitable substituents.

* * * * *